US012654008B2

(12) United States Patent
Martinot

(10) Patent No.: US 12,654,008 B2
(45) Date of Patent: Jun. 16, 2026

(54) SYSTEMS AND METHODS FOR A WEARABLE DEVICE FOR IMPROVING SLEEP

(71) Applicant: Sunrise SA, Namur (BE)

(72) Inventor: Pierre Martinot, Namur (BE)

(73) Assignee: Sunrise SA, Namur (BE)

( * ) Notice: Subject to any disclaimer, the term of this patent is extended or adjusted under 35 U.S.C. 154(b) by 284 days.

(21) Appl. No.: 18/462,298

(22) Filed: Sep. 6, 2023

(65) Prior Publication Data

US 2023/0414940 A1 Dec. 28, 2023

Related U.S. Application Data

(63) Continuation-in-part of application No. 17/821,447, filed on Aug. 22, 2022, now Pat. No. 11,752,327, (Continued)

(30) Foreign Application Priority Data

Oct. 1, 2020 (EP) ...................................... 20199684

(51) Int. Cl.
*A61N 1/36* (2006.01)
*A61N 1/04* (2006.01)

(52) U.S. Cl.
CPC ......... *A61N 1/3601* (2013.01); *A61N 1/0452* (2013.01); *A61N 1/0476* (2013.01); *A61N 1/0492* (2013.01); *A61N 1/36034* (2017.08)

(58) Field of Classification Search
CPC ................ A61N 1/0452; A61N 1/0496; A61N 1/36031; A61N 1/0484; A61N 1/0492;
(Continued)

(56) References Cited

U.S. PATENT DOCUMENTS

| | | |
|---|---|---|
| 3,801,758 A | 4/1974 | Shand et al. |
| 6,107,922 A | 8/2000 | Bryuzgin |
| (Continued) | | |

FOREIGN PATENT DOCUMENTS

| | | |
|---|---|---|
| CA | 2163855 A1 | 6/1996 |
| CN | 1602970 A | 4/2005 |
| (Continued) | | |

OTHER PUBLICATIONS

Abraham, et al., Phrenic Nerve Stimulation for the Treatment of Central Sleep Apnea, Jacc: Heart Failure, 3(5):360-369 (May 2015).
(Continued)

*Primary Examiner* — Rex R Holmes
(74) *Attorney, Agent, or Firm* — Greenberg Traurig, LLP; Christopher C. Bolten; Robert D. Ward

(57) ABSTRACT

The present disclosure is in the field of sleep and respiratory care. In particular, the present disclosure provides means and methods for stimulating select muscles of a subject for improving sleep. A wearable device is provided to be worn on the head of the subject and having stimulating electrodes arranged on the wearable device such that when the wearable device is worn by the subject the electrodes contact the subject's skin for transcutaneous stimulation of the subject's facial muscles. For example, the wearable device may include two electrodes for transcutaneously stimulating the subject's left and right masseter muscles and two electrodes for transcutaneously stimulating the subject's left and right pterygoid muscles. Stimulating the masseter and pterygoid muscles causes the masseter and pterygoid muscles to contract, thereby elevating the subject's mandible to decrease respiratory effort during sleep. The present disclosure also provides means and methods for treating the snoring of a sleeping subject.

20 Claims, 21 Drawing Sheets

Related U.S. Application Data which is a continuation of application No. PCT/EP2021/077190, filed on Oct. 1, 2021.

(58) Field of Classification Search
CPC .............. A61N 1/3601; A61N 1/36034; A61N 1/3611; A61B 5/4812; A61B 2562/0219; A61B 5/4806
See application file for complete search history.

(56) References Cited

U.S. PATENT DOCUMENTS

| | | | |
|---|---|---|---|
| 7,680,538 | B2 | 3/2010 | Durand et al. |
| 7,949,403 | B2 | 5/2011 | Palermo et al. |
| 8,545,416 | B1 | 10/2013 | Kayyali et al. |
| 8,548,770 | B2 | 10/2013 | Yuen et al. |
| 9,014,819 | B2 | 4/2015 | Lee et al. |
| 9,180,267 | B2 | 11/2015 | Bowditch et al. |
| 9,415,216 | B2 | 8/2016 | Mashiach |
| 9,504,828 | B2 | 11/2016 | Mashiach et al. |
| 9,643,022 | B2 | 5/2017 | Mashiach et al. |
| 9,750,977 | B2 | 9/2017 | Yuen et al. |
| 10,029,098 | B2 | 7/2018 | Papay |
| 10,092,219 | B2 | 10/2018 | Arnold et al. |
| 10,311,745 | B2 | 6/2019 | Arnold et al. |
| 10,354,135 | B2 | 7/2019 | Herscovici-Cohen et al. |
| 10,381,109 | B2 | 8/2019 | Hong et al. |
| 10,695,528 | B2 | 6/2020 | Soulet et al. |
| 10,700,774 | B2 | 6/2020 | Panther et al. |
| 10,755,814 | B2 | 8/2020 | Bradley |
| 10,814,137 | B2 | 10/2020 | Mashiach et al. |
| 11,033,738 | B2 | 6/2021 | Steier |
| 11,191,970 | B2 | 12/2021 | Mashiach et al. |
| 11,298,258 | B2 | 4/2022 | Bedford |
| 11,752,327 | B2 | 9/2023 | Martinot |
| 11,864,910 | B2 | 1/2024 | Martinot |
| 11,992,671 | B2 | 5/2024 | Martinot |
| 12,257,069 | B2 | 3/2025 | Martinot |
| 12,369,850 | B2 | 7/2025 | Martinot |
| 2007/0156182 | A1* | 7/2007 | Castel ................ A61N 1/36034 607/2 |
| 2007/0273366 | A1 | 11/2007 | Ansay et al. |
| 2008/0033304 | A1 | 2/2008 | Dalal et al. |
| 2009/0275031 | A1 | 11/2009 | Tanner et al. |
| 2011/0230702 | A1* | 9/2011 | Honour .................... A61N 1/40 607/42 |
| 2011/0308528 | A1 | 12/2011 | Ciardullo |
| 2013/0096843 | A1 | 4/2013 | Yuen et al. |
| 2013/0226020 | A1 | 8/2013 | Holley et al. |
| 2014/0278139 | A1 | 9/2014 | Hong et al. |
| 2016/0022203 | A1 | 1/2016 | Arnold et al. |
| 2016/0128624 | A1 | 5/2016 | Matt |
| 2016/0296165 | A1 | 10/2016 | Moore et al. |
| 2016/0325143 | A1 | 11/2016 | Yuen et al. |
| 2017/0035350 | A1 | 2/2017 | Allessie |
| 2017/0265801 | A1 | 9/2017 | Patwa et al. |
| 2017/0347946 | A1 | 12/2017 | Arnold et al. |
| 2018/0000563 | A1 | 1/2018 | Shanjani et al. |
| 2018/0110960 | A1 | 4/2018 | Youngblood et al. |
| 2018/0116863 | A1 | 5/2018 | Shah et al. |
| 2018/0117317 | A1 | 5/2018 | Oku et al. |
| 2018/0126107 | A1* | 5/2018 | Valster ................. A61B 5/4836 |
| 2018/0261324 | A1 | 9/2018 | Bradley |
| 2018/0272118 | A1* | 9/2018 | Goldwasser ......... A61N 1/0492 |
| 2019/0021651 | A1 | 1/2019 | Hanssen et al. |
| 2019/0142625 | A1 | 5/2019 | Goff et al. |
| 2019/0229802 | A1 | 7/2019 | Panther et al. |
| 2019/0247650 | A1 | 8/2019 | Tran |
| 2020/0015737 | A1 | 1/2020 | Van Pee et al. |
| 2020/0016401 | A1 | 1/2020 | Papay et al. |
| 2020/0129762 | A1 | 4/2020 | Toong et al. |
| 2020/0155840 | A1 | 5/2020 | Giannoukos et al. |
| 2020/0155846 | A1 | 5/2020 | Toong et al. |
| 2020/0163794 | A1 | 5/2020 | Goff et al. |
| 2020/0353244 | A1 | 11/2020 | Yamazaki |
| 2021/0162211 | A1 | 6/2021 | Chase et al. |
| 2021/0260369 | A1 | 8/2021 | Steier |

FOREIGN PATENT DOCUMENTS

| | | |
|---|---|---|
| CN | 101566328 A | 10/2009 |
| CN | 103167828 A | 6/2013 |
| CN | 205493840 U | 8/2016 |
| CN | 106163391 A | 11/2016 |
| CN | 107205721 A | 9/2017 |
| CN | 107405486 A | 11/2017 |
| CN | 107440680 A | 12/2017 |
| CN | 107518952 A | 12/2017 |
| CN | 107614056 A | 1/2018 |
| CN | 108451503 A | 8/2018 |
| DE | 202013105962 U1 | 1/2014 |
| DE | 102016120583 B3 | 4/2018 |
| EP | 3253443 B1 | 11/2018 |
| EP | 3801758 A1 | 4/2021 |
| FR | 2655072 A1 | 5/1991 |
| JP | 2004187961 A | 7/2004 |
| JP | 2014158607 A | 9/2014 |
| JP | 2017533752 A | 11/2017 |
| KR | 20130134268 A | 12/2013 |
| KR | 20170083483 A | 7/2017 |
| RU | 2015154805 A | 6/2017 |
| RU | 2628064 C2 | 8/2017 |
| WO | WO-2009012298 A2 | 1/2009 |
| WO | WO-2020035852 A2 | 2/2020 |
| WO | WO-2020193778 A1 | 10/2020 |
| WO | WO-2020261226 A1 | 12/2020 |
| WO | WO-2022069748 A2 | 4/2022 |

OTHER PUBLICATIONS

Allen, et al., Using Electrical Stimulation, A Guideline for Allied Health Professionals, Jan. 2014.

Ayappa et al. "The upper airway in sleep: physiology of the pharynx," Sleep Medicine Review, 7(1):9-33 (2003).

Benjafield, et al., Estimation of the global prevalence and burden of obstructive sleep apnoea: a literature-based analysis, The lancet Respiratory Medicine, 7(8):687-98 (Aug. 2019).

Berquin et al. "Brainstem and hypothalamic areas involved in respiratory chemoreflexes: a Fos study in adult rats," Brain Research, 857:30-40 (2000).

Boon, et al., Upper Airway Stimulation for Obstructive Sleep Apnea: Results from the ADHERE Registry, Otolaryngology-Head and Neck Surgery, 159(2):379-385 (Aug. 2018).

CES 2021 Innovation Award product, Sunrise, accessed at https://www.ces.tech/innovation-awards/honorees/2021/honorees/s/sunrise.aspx.

Decker, et al., Functional electrical stimulation and respiration during sleep, J. Appl. Physiol., 75(3):1056-1061 (Sep. 1993).

Dotan, et al., Parameters affecting pharyngeal response to genioglossus stimulation in sleep apnoea, Eur. Respir. J., 38(2):338-347 (Aug. 2011).

Eastwood, et al., Bilateral hypoglossal nerve stimulation for treatment of adult obstructive sleep apnoea, Eur. Respir. J., 55(1):1901320 (Jan. 2020).

Eastwood, et al., Treating Obstructive Sleep Apnea with Hypoglossal Nerve Stimulation, Sleep, 34(11):1479-1486 (Nov. 2011).

Edmonds, et al., The Effects of Transcutaneous Electrical Stimulation During Wakefulness and Sleep in Patients with Obstructive Sleep Apnea, Am. Rev. Respir. Dis., 146(4):1030-1036 (Oct. 1992).

Europe's 100 hottest young scaleups of 2021, awarded by The Next Web (TNW), accessed at thenextweb.com (2021).

Extended EP Search Report dated Mar. 11, 2021 in EP Patent Application Serial No. 20199684.0 (0230).

French Ministry of Health-Sunrise-relating to coverage under Article L. 165-1 of the Social Security Code for the diagnosis of obstructive sleep apnea-hypopnea syndrome, Jun. 17, 2021, accessed at, https://www.legifrance.gouv.fr/jorf/id/JORFTEXT000043699634.

(56)                    References Cited

OTHER PUBLICATIONS

Friedman, et al., Targeted Hypoglossal Nerve Stimulation for the Treatment of Obstructive Sleep Apnea: Six-Month Results, The Laryngoscope, 126(11):2618-2623 (Nov. 2016).

Gestreau et al. "Differential Brainstem Fos-Like Immunoreactivity after Laryngeal-induced Coughing and Its Reduction by Codeine," The Journal of Neuroscience, 17(23):9340-9352 (Dec. 1997).

Giannasi, et al., Effects of Neuromuscular Electrical Stimulation on the Masticatory Muscles and Physiologic Sleep Variables in Adults with Cerebral Palsy: A Novel Therapeutic Approach, PloS one, 10(8):e0128959 (Aug. 2015).

Goding, et al., Hypoglassal nerve Stimulation and Airway Changes Under Fluoroscopy, Otolaryngology-Head and Neck Surgery, 146(6):117-1022 (Jun. 2012).

Guilleminault, et al., The Effect of Electrical Stimulation on Obstructive Sleep Apnea Syndrome, Chest, 107(1):67-73 (Jan. 1995).

Heiser, et al., Functional Outcome of tongue motions with selective hypoglossal nerve stimulation in patients with obstructive sleep apnea, Sleep and Breathing, 20(2):553-60 (May 2016).

Heiser, et al., Selective upper airway stimulation for obstructive sleep apnea: a single center clinical experience, Eur. Arch. Oto-Rhino-Laryngology, 274(3):1727-1734 (Mar. 2017).

Henke et al. "Load compensation and respiratory muscle function during sleep," J. Appl. Physiol., 72(4):1221-1234 (1992).

Hida, et al., Effects of submental stimulation for several consecutive nights in patients with obstructive sleep apnoea, Thorax, 49(5):446-452 (May 1994).

Hida, et al., The Effect of Submental Electrical Stimulation on Sleep Disordered Breathing in Patients with Obstructive Apnea, Sleep, 16:S96-S97 (Dec. 1993).

Hofauer, et al., Effects of upper-airway stimulation on sleep architecture in patients with obstructive sleep apnea, Sleep Breath, 21(4):901-908 (Dec. 2017).

Hofauer, et al., Patient experience with upper airway stimulation in the treatment of obstructive sleep apnea, Sleep and Breathing, 23(1);235-241 (Mar. 2019).

Hollowell et al. "Activation of masseter muscles with respiratory resistance loading," J. Appl. Physiol., 67(1):270-275 (1989).

Hollowell et al. "Mandible position and activation of submental and masseter muscle during sleep," J. Appl. Physiol., 71(6):2267-2273 (1991).

Hollowell et al. "Respiratory-related recruitment of the masseter: response to hypercapnia and loading," J. Appl. Physiol., 70(6):2508-2513 (1991).

Hu, et al., Percutaneous Biphasic Electrical Stimulation for Treatment of Obstructive Sleep Apnea Syndrome, IEEE Transactions on Biomedical Engineering, 55(1):181-187 (Jan. 2008).

International Search Report & Written Opinion dated Apr. 8, 2022 in Int'l PCT Patent Appl. Serial No. PCT/EP2021/077190 (0210).

International Search Report & Written Opinion dated Aug. 21, 2020 in Int'l PCT Patent Appl. Serial No. PCT/EP2020/058822 (0110).

Isono, et al., Effects of tongue electrical stimulation on pharyngeal mechanics in anaesthetized patients with obstructive sleep apnoea, Eur. Respir. J., 14(6):1258-1265 (1999).

Kelly et al. "Diagnosis of Sleep Apnoea Using a Mandibular Monitor and Machine Learning Analysis: One-Night Agreement Compared to in-Home Polysomnography," Frontiers in Neuroscience, 16:1-10 (Mar. 2022).

Kezirian, et al., Hypoglossal nerve stimulation improves obstructive sleep apnoea, J. Sleep Res., 23(1):77-83 (Feb. 2014).

Lewis, et al., Implantation of the Nyxoah Bilateral Hypoglossal Nerve Stimulator for Obstructive Sleep Apnea, Laryngoscope Investigative Otolaryngology, 46(6):703-707 (Dec. 2019).

Lin, et al., Development of the Miniaturized Wireless Inertial measurement Unit WB-4: Pilot Test for Mastication Analysis, IEEE/SICE International Symposium on System Integration, Sendai, Japan, pp. 420-425 (Dec. 2010).

Martinot et al. "Artificial Intelligence Analysis of Mandibular Movements Enables Accurate Detection of Phasic Sleep Bruxism in OSA Patients: A Pilot Study," Nature and Science of Sleep, vol. 13., 1449-1459 (Aug. 2021).

Martinot et al. "Bruxism Relived under CPAP Treatment in a Patient With OSA Syndrome," Chest, 157(3):e59-e62 (2020).

Martinot et al. "Clinical validation of a mandibular movement signal based system for the diagnosis of pediatric sleep apnea," Pediatric Pulmonology, pp. 1-10 (Feb. 2021).

Martinot et al. "Mandibular Movements as Accurate Reporters of Respiratory Effort during Sleep: Validation against Diaphragmatic Electromyography," Frontiers in Neurology, 8(353):1-8 (Jul. 2017).

Martinot et al. "Mandibular Movements Identify Respiratory Effort in Pediatric Obstructive Sleep Apnea," J. Clin Sleep Med. 11(5):567-574 (2015).

Martinot et al. "Mandibular position and movements: Suitability for diagnosis of sleep apnoea," Respirology, pp. 1-8 (Aug. 2016).

Martinot et al. "Monitoring mandibular movements to detect Cheyne-Stokes Breathing," Respiratory Research 18:66 pp. 1-9 (2017).

Martinot et al. "Persistent Respiratory Effort After Adenotonsillectomy in Children with Sleep-Disordered Breathing," Sleep Respiratory—Laryngoscope, pp. 1-8 (2017).

Martinot et al. "The key role of the mandible in modulating airflow amplitude during sleep," Respiratory Physiology & Neurobiology, 279:103447 pp. 1-6 (May 2020).

Maurer, et al., Operative technique of upper airway stimulation: an implantable treatment of obstructive sleep apnea, Operative Techniques in Otolaryngology-Head and Neck Surgery, 23(3):227-233 (Sep. 2012).

Merrill et al. "Origin of the Expiratory Inhibition of Nucleus Tractus Solitarius Inspiratory Neurones," Brain Research, 263:43-50 (1983).

Miki, et al., Effects of Electrical Stimulation of the Genioglossus on Upper Airway Resistance in Anesthetized Dogs, Am. Rev. Respir. Dis., 140(5):1279-84 (1989).

Miki, et al., Effects of Submental Electrical Stimulation During Sleep on Upper Airway Patency in Patients with Obstructive Sleep Apnea, Am. Rev. Respir. Dis., 140(5):1285-1290 (1989).

Moore et al. "How the brainstem controls orofacial behaviors comprised of rhythmic action," Trends in Neuroscience—Cell Press, pp. 1-11 (2014).

National Sleep Foundation's 2022 SleepTech Award, AYO and Sunrise Win National Sleep Foundation's 2022 SleepTech Award, accessed at https://www/thensf.org/avo-and-sunrise-win-national-sleep-foundations-2022-sleeptech-award.

Oliven, et al., Improved Upper Airway Patency Elicited by Electrical Stimulation of The Hypoglossus Nerves, Respiration, 63(4):213-216 (1996).

Oliven, et al., Sublingual electrical stimulation of the tongue during wakefulness and sleep, Respiration Physiology, 127(2-3):217-226 (Sep. 2001).

Oliven, et al., Upper airway response to electrical stimulation of the genioglossus in obstructive sleep apnea, J. Appl. Physiol, 95(5):2023-2029 (Nov. 2003).

Peek et al. "Machine Learning-based Sleep Staging in Patients with Sleep Apnea Using a Single Mandibular Movement Signal," Am. Journal of Respiratory and Critical Care Medicine, vol. 204:10, 1227-1230 (Nov. 2021).

Pepin et al. "Assessment of Mandibular Movement Monitoring With Machine Learning Analysis for the Diagnosis of obstructive Sleep Apnea," JAMA network Open, pp. 1-12 (Jan. 2020).

Polese, et al., Portable monitoring devices in the diagnosis of obstructive sleep apnea: current status, advantages, and limitations, J. Bras. Pneumol., 36(4):498-505 (2010).

Schwartz, et al., Electrical Stimulation of the Lingual Musculature in Obstructive Sleep Apnea, J. Appl. Physiol, 81(2):643-652 (Aug. 1996).

Schwartz, et al., Therapeutic Electrical Stimulation of the Hypoglossal Nerve in Obstructive Sleep Apnea, Arch. Otolaryngol. Head Neck Surg., 127(10):1216-1223 (Oct. 2001).

SLEEP 2022, "Sunrise unveils ground-breaking home sleep apnea test at SLEEP 2022," accessed at https://www.prnewswire.com/news-releases/sunrise-unveils-ground-breaking-home-sleep-apnea-test-at-sleep-2022-301543710.html.

(56) References Cited

OTHER PUBLICATIONS

Sunrise FDA 510(k) Approval on Device for Sleep Apnea Testing Based on Mandibular Movement (Dec. 22, 2022), available at https://www.accessdatta.fda.gov/cdrh_docs/pdf22/K222262.pdf.

Tamura et al. "Mandibular Advancement Improves the Laryngeal View during Direct Laryngoscopy Performed by Inexperienced Physicians," Anesthesiology, 100(3):598-601 (Mar. 2004).

The Big Squeeze Awards, "Disruptive Innovation of the Year," awarded by Startups.be & Scale-Ups.eu, accessed at https://www.startups.be/the-big-squeeze (2021).

Sunrise Receives FDA Clearance for Its At-home Sleep Apnea Test, BusinessWire, Feb. 1, 2023, accessed at https://www.businesswire.com/news/home/20230213005361/rn/Sunrise-Receives-FDA-Clearance-for-Its-At-home-Sleep-Apnea-Test.

Woodson, et al., Randomized Controlled Withdrawal Study of Upper Airway Stimulation on OSA: Short- and Long-term Effect, Otolaryngology-Head and Neck Surgery, 151(5):880-887 (Nov. 2014).

Guo-Ping, et al., Mandibular distraction osteogenesis for improving respiratory function in patients with micrognathia complicated by obstructive sleep apnea syndrome, Chinese Journal of Clinical Rehabilitation, 9(6):195-198 (Feb. 2005).

Liang, et al., Distraction osteogenesis for treatment of temporomandibular joint ankylosis accompanying with mandibular micrognathia and obstructive sleep apnea syndrome, Journal Peking University (Health Sci), 34:112-116 (Dec. 2002).

Medical Advisory Secretariat, Oral Appliances For Obstructive Sleep Apnea: An Evidence-Based Analysis, *Ontario Health Technology Assessment Series*, 9(5):1-51 (Sep. 2009).

* cited by examiner

Fixed cut offs

| Wake state detection | Balanced wake/sleeping state detection | Sleeping state detection |
|---|---|---|
| Sensitivity constrained to 0.90 and maximize specificity | Balance between sensitivity and specificity | Specificity constrained to 0.90 and maximize sensitivity |

GNORM STD > 0.3455

Chin

|  | Wake | Sleep |
|---|---|---|
| Wake | 8394 | 14064 |
| Sleep | 932 | 14608 |

Total = 37998

Chin

|  | Wake | Sleep |
|---|---|---|
| Wake | 0.90 | 0.49 |
| Sleep | 0.10 | 0.51 |

Sens 0.90
Spec 0.51

GNORM max > 2.2555

Chin

|  | Wake | Sleep |
|---|---|---|
| Wake | 8394 | 13760 |
| Sleep | 932 | 14912 |

Total = 37998

Chin

|  | Wake | Sleep |
|---|---|---|
| Wake | 0.90 | 0.48 |
| Sleep | 0.10 | 0.52 |

Sens 0.90
Spec 0.52

GNORM STD > 1.1725

Chin

|  | Wake | Sleep |
|---|---|---|
| Wake | 7377 | 5993 |
| Sleep | 1949 | 22679 |

Total = 37998

Chin

|  | Wake | Sleep |
|---|---|---|
| Wake | 0.79 | 0.21 |
| Sleep | 0.21 | 0.79 |

Sens 0.79
Spec 0.79

GNORM max > 7.7145

Chin

|  | Wake | Sleep |
|---|---|---|
| Wake | 7416 | 5872 |
| Sleep | 1910 | 22800 |

Total = 37998

Chin

|  | Wake | Sleep |
|---|---|---|
| Wake | 0.80 | 0.20 |
| Sleep | 0.20 | 0.80 |

Sens 0.80
Spec 0.80

GNORM STD > 2.3133

Chin

|  | Wake | Sleep |
|---|---|---|
| Wake | 6412 | 2867 |
| Sleep | 2914 | 25805 |

Total = 37998

Chin

|  | Wake | Sleep |
|---|---|---|
| Wake | 0.69 | 0.10 |
| Sleep | 0.31 | 0.90 |

Sens 0.69
Spec 0.90

GNORM max > 14.35

Chin

|  | Wake | Sleep |
|---|---|---|
| Wake | 6501 | 2866 |
| Sleep | 2725 | 25806 |

Total = 37998

Chin

|  | Wake | Sleep |
|---|---|---|
| Wake | 0.71 | 0.10 |
| Sleep | 0.29 | 0.90 |

Sens 0.71
Spec 0.90

FIG. 18

Wake state detection for fixed cut-off data

| # | Chin – data Sleep | Chin – data Wake | Cheek – data Sleep | Cheek – data Wake | Cheek – SD Sleep | Cheek – SD Wake | Cheek – MAX Sleep | Cheek – MAX Wake | Diff TST | Diff TST1 | Diff TST2 |
|----|------|------|------|------|------|-------|------|-------|--------|--------|--------|
| 1 | 7.67 | 3.09 | 7.78 | 2.98 | 6.11 | 4.65 | 5.86 | 4.90 | 1.53% | 20.33% | 23.59% |
| 2 | 6.17 | 3.38 | 6.03 | 3.52 | 1.76 | 7.79 | 2.09 | 7.45 | 1.90% | 71.49% | 66.08% |
| 3 | 8.43 | 1.65 | 8.48 | 1.60 | 6.65 | 3.43 | 6.04 | 4.04 | 0.59% | 21.15% | 28.36% |
| 4 | 8.27 | 2.42 | 8.58 | 2.10 | 4.02 | 6.67 | 3.92 | 6.77 | 1.83% | 51.41% | 52.62% |
| 5 | 8.03 | 2.04 | 7.98 | 2.09 | 5.10 | 4.58 | 4.56 | 5.52 | 0.62% | 36.51% | 43.26% |
| 6 | 7.08 | 3.86 | 8.33 | 2.61 | 0.73 | 10.22 | 1.33 | 9.71 | 17.65% | 89.76% | 82.59% |
| 7 | 7.67 | 1.24 | 7.43 | 1.49 | 5.45 | 3.46 | 5.13 | 3.78 | 3.13% | 28.91% | 33.04% |
| 8 | 8.85 | 2.01 | 9.02 | 1.84 | 7.26 | 3.60 | 7.55 | 3.31 | 1.80% | 17.98% | 14.69% |
| 9 | 7.93 | 2.08 | 7.90 | 2.09 | 6.25 | 3.74 | 6.13 | 3.87 | 0.21% | 21.05% | 22.63% |
| 10 | 8.93 | 2.37 | 9.13 | 2.16 | 2.79 | 8.57 | 3.09 | 8.27 | 2.33% | 69.47% | 66.11% |
| 11 | 6.78 | 2.38 | 6.78 | 2.38 | 3.67 | 5.49 | 3.82 | 5.34 | 0.12% | 45.88% | 43.67% |
| 12 | 8.46 | 2.24 | 8.53 | 2.18 | 8.19 | 2.51 | 7.92 | 2.78 | 0.79% | 5.15% | 6.46% |
| 13 | 8.10 | 3.03 | 8.55 | 2.58 | 6.93 | 4.20 | 6.97 | 4.16 | 5.50% | 14.55% | 13.99% |
| 14 | 8.71 | 2.12 | 8.69 | 2.13 | 5.08 | 5.75 | 5.19 | 5.63 | 0.19% | 41.72% | 40.38% |
| 15 | 7.04 | 3.58 | 7.64 | 2.98 | 4.47 | 6.16 | 4.45 | 6.18 | 8.55% | 36.57% | 36.80% |
| 16 | 7.76 | 1.95 | 8.08 | 1.63 | 4.97 | 4.84 | 5.11 | 4.60 | 4.06% | 37.27% | 34.16% |
| 17 | 8.75 | 2.63 | 8.39 | 2.98 | 7.99 | 3.36 | 7.80 | 3.58 | 4.10% | 6.07% | 10.86% |
| 18 | 7.68 | 3.35 | 7.88 | 3.15 | 6.69 | 4.33 | 6.66 | 4.37 | 2.61% | 12.61% | 13.25% |
| 19 | 7.78 | 3.13 | 8.19 | 2.73 | 1.88 | 9.03 | 1.83 | 9.09 | 5.25% | 75.86% | 76.55% |
| 20 | 6.34 | 3.93 | 6.79 | 3.48 | 1.63 | 8.63 | 1.65 | 8.62 | 7.10% | 74.11% | 73.98% |
| 21 | 8.96 | 2.88 | 9.33 | 2.50 | 3.21 | 8.63 | 4.35 | 7.58 | 4.05% | 64.19% | 52.56% |
| 22 | 7.86 | 3.48 | 8.31 | 3.03 | 5.73 | 5.61 | 5.61 | 5.73 | 5.73% | 27.15% | 28.63% |
| 23 | 7.58 | 2.58 | 7.35 | 2.82 | 3.88 | 6.38 | 4.19 | 5.98 | 3.00% | 48.79% | 44.73% |
| 24 | 7.79 | 2.15 | 7.93 | 2.02 | 3.18 | 6.77 | 3.61 | 6.33 | 1.71% | 59.25% | 53.69% |
| 25 | 7.66 | 3.31 | 7.81 | 3.16 | 3.65 | 7.31 | 3.60 | 7.57 | 1.90% | 52.23% | 55.60% |
| 26 | 9.23 | 1.30 | 9.22 | 1.31 | 0.94 | 10.18 | 0.38 | 10.17 | 0.09% | 96.30% | 98.12% |
| 27 | 7.61 | 2.86 | 7.63 | 2.84 | 8.37 | 7.10 | 8.88 | 6.59 | 0.22% | 55.75% | 49.07% |
| 28 | 8.63 | 2.06 | 8.47 | 2.23 | 1.98 | 8.81 | 1.88 | 8.82 | 1.93% | 78.19% | 78.28% |
| 29 | 7.53 | 2.95 | 7.41 | 3.07 | 2.83 | 7.64 | 3.12 | 7.36 | 1.55% | 62.35% | 58.58% |
| 30 | 9.69 | 1.70 | 9.29 | 2.10 | 8.98 | 7.41 | 4.83 | 6.56 | 4.15% | 58.98% | 50.13% |

FIG. 19

Balanced sleep/wake state detection for fixed cut-off data

| | Chin - data | | Cheek - data | | Cheek - SD | | Cheek - MAX | | Diff TST | Diff TST1 | Diff TST2 |
|---|---|---|---|---|---|---|---|---|---|---|---|
| | Sleep | Wake | Sleep | Wake | Sleep | Wake | Sleep | Wake | | | |
| 1 | 7.67 | 3.09 | 7.28 | 2.98 | 7.43 | 3.33 | 7.30 | 3.46 | 1.52% | 3.13% | 4.79% |
| 2 | 6.17 | 3.38 | 6.03 | 3.52 | 4.77 | 4.78 | 4.83 | 4.72 | 2.30% | 22.70% | 31.76% |
| 3 | 8.43 | 1.63 | 8.48 | 1.60 | 8.48 | 1.60 | 8.35 | 1.73 | 0.59% | 0.59% | 0.99% |
| 4 | 8.27 | 2.42 | 6.58 | 2.10 | 6.34 | 4.34 | 6.36 | 4.33 | 1.66% | 23.29% | 23.08% |
| 5 | 8.03 | 2.04 | 7.98 | 3.09 | 7.22 | 2.86 | 6.79 | 3.28 | 0.62% | 10.17% | 15.46% |
| 6 | 7.08 | 3.86 | 8.33 | 2.61 | 4.22 | 6.73 | 4.31 | 6.63 | 17.65% | 40.47% | 39.18% |
| 7 | 7.67 | 1.24 | 7.43 | 1.48 | 7.66 | 1.23 | 7.40 | 1.51 | 8.15% | 0.11% | 3.46% |
| 8 | 8.85 | 3.01 | 9.02 | 1.84 | 9.09 | 1.77 | 9.02 | 1.84 | 1.68% | 2.72% | 1.99% |
| 9 | 7.92 | 2.08 | 7.90 | 2.09 | 7.54 | 2.45 | 7.43 | 2.54 | 0.22% | 4.06% | 5.89% |
| 10 | 8.93 | 2.37 | 9.13 | 2.16 | 7.05 | 4.24 | 7.44 | 3.85 | 2.13% | 21.01% | 16.62% |
| 11 | 6.78 | 2.36 | 6.78 | 2.38 | 5.91 | 3.25 | 5.81 | 3.35 | 0.15% | 12.79% | 14.57% |
| 12 | 8.46 | 2.24 | 8.53 | 2.18 | 8.96 | 1.74 | 8.89 | 1.83 | 0.79% | 5.53% | 5.12% |
| 13 | 8.10 | 3.03 | 8.55 | 2.58 | 8.64 | 2.48 | 8.52 | 2.61 | 5.50% | 6.66% | 5.14% |
| 14 | 8.71 | 2.12 | 8.69 | 2.33 | 7.88 | 2.95 | 7.58 | 3.25 | 0.19% | 8.57% | 18.03% |
| 15 | 7.04 | 3.50 | 7.64 | 2.98 | 6.31 | 4.32 | 6.25 | 4.38 | 6.57% | 10.41% | 11.63% |
| 16 | 7.76 | 1.95 | 8.08 | 1.63 | 7.22 | 2.49 | 7.03 | 2.68 | 4.06% | 6.98% | 9.64% |
| 17 | 8.75 | 2.63 | 8.39 | 2.98 | 8.44 | 2.93 | 8.43 | 2.95 | 4.10% | 3.03% | 3.71% |
| 18 | 7.68 | 3.35 | 7.88 | 3.15 | 7.17 | 3.86 | 7.16 | 3.87 | 2.61% | 8.62% | 6.70% |
| 19 | 7.78 | 3.13 | 6.19 | 2.73 | 6.43 | 4.49 | 6.67 | 4.25 | 5.25% | 17.45% | 14.63% |
| 20 | 6.34 | 3.93 | 6.79 | 3.48 | 4.08 | 6.18 | 6.90 | 6.32 | 7.05% | 35.61% | 37.71% |
| 21 | 8.96 | 2.88 | 9.33 | 2.50 | 7.49 | 4.34 | 7.53 | 4.25 | 4.05% | 16.37% | 15.35% |
| 22 | 7.86 | 3.46 | 6.31 | 3.03 | 7.66 | 3.65 | 7.58 | 3.76 | 5.25% | 4.22% | 3.61% |
| 23 | 7.58 | 2.58 | 7.35 | 2.82 | 6.83 | 3.34 | 6.83 | 3.33 | 3.66% | 10.00% | 9.20% |
| 24 | 7.79 | 2.15 | 7.93 | 2.02 | 7.02 | 2.93 | 6.98 | 2.97 | 1.77% | 9.95% | 10.46% |
| 25 | 7.66 | 3.31 | 7.81 | 3.16 | 6.62 | 4.35 | 6.43 | 4.54 | 1.68% | 12.60% | 16.10% |
| 26 | 9.33 | 1.30 | 9.22 | 1.31 | 6.86 | 6.83 | 6.86 | 7.85 | 0.05% | 81.65% | 71.00% |
| 27 | 7.61 | 2.86 | 7.63 | 2.64 | 7.35 | 3.12 | 7.28 | 3.18 | 0.22% | 3.42% | 4.27% |
| 28 | 6.63 | 2.06 | 8.47 | 3.23 | 4.70 | 5.99 | 5.12 | 5.58 | 1.95% | 45.56% | 40.73% |
| 29 | 7.53 | 2.95 | 7.41 | 3.07 | 6.73 | 3.75 | 6.58 | 3.89 | 1.53% | 10.65% | 12.31% |
| 30 | 9.69 | 1.70 | 9.29 | 2.10 | 8.30 | 3.09 | 9.35 | 2.04 | 4.13% | 14.26% | 3.55% |

FIG. 20

Figure 21:
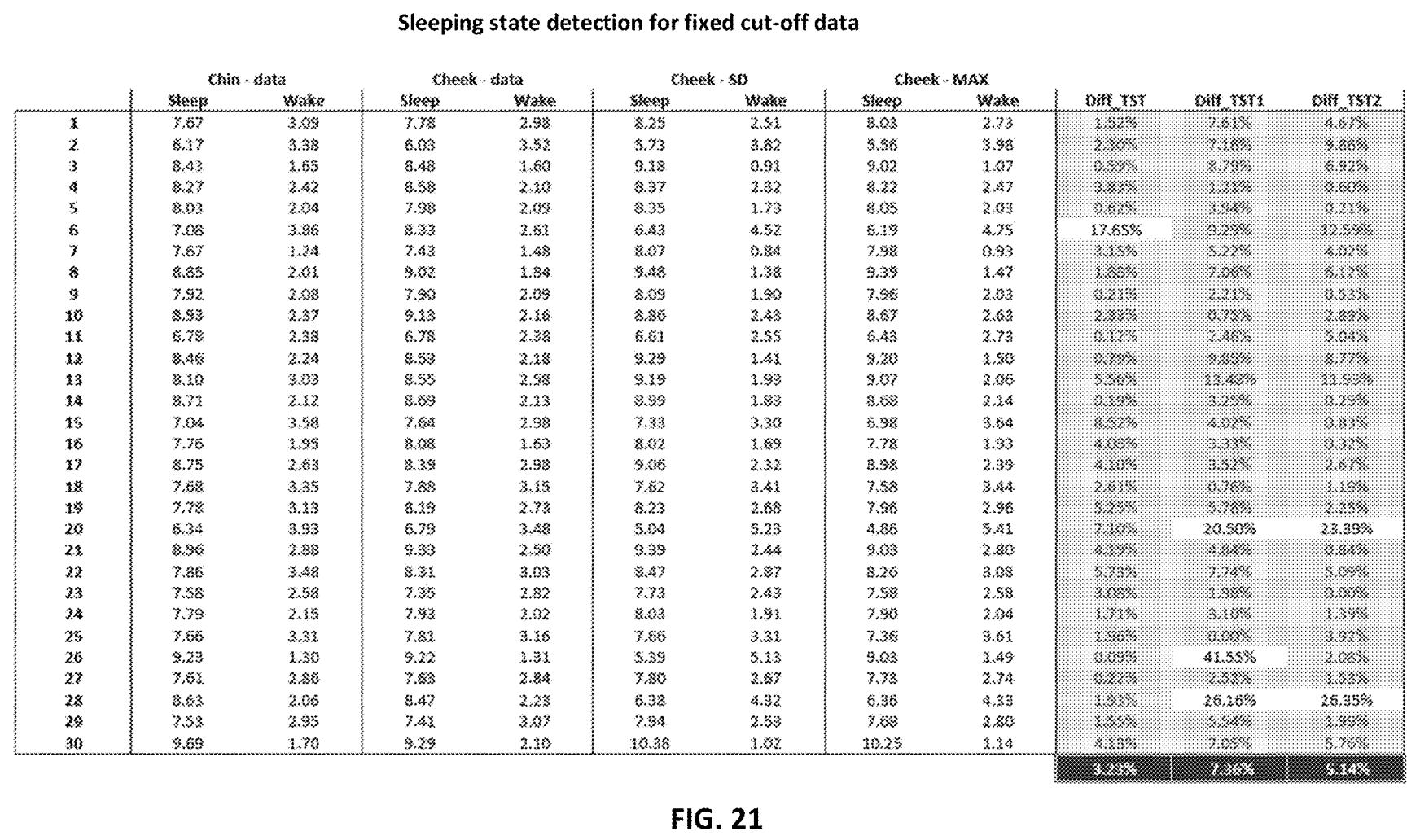

Sleeping state detection for fixed cut-off data

| | Chin - data | | Cheek - data | | Cheek - SD | | Cheek - MAX | | Diff_TST | Diff_TST1 | Diff_TST2 |
|---|---|---|---|---|---|---|---|---|---|---|---|
| | Sleep | Wake | Sleep | Wake | Sleep | Wake | Sleep | Wake | | | |
| 1 | 7.67 | 3.09 | 7.78 | 2.98 | 8.25 | 2.51 | 8.03 | 2.73 | | | |
| 2 | 6.17 | 3.38 | 6.03 | 3.53 | 5.73 | 3.82 | 5.56 | 3.98 | | | |
| 3 | 8.43 | 1.65 | 8.48 | 1.60 | 9.18 | 0.91 | 9.02 | 1.07 | | | |
| 4 | 8.27 | 2.42 | 8.58 | 2.10 | 8.37 | 2.32 | 8.22 | 2.47 | | | |
| 5 | 8.03 | 2.04 | 7.98 | 2.09 | 8.35 | 1.73 | 8.05 | 2.03 | | | |
| 6 | 7.06 | 3.86 | 8.33 | 2.61 | 6.43 | 4.52 | 6.19 | 4.75 | 17.65% | | |
| 7 | 7.67 | 1.24 | 7.43 | 1.48 | 8.07 | 0.84 | 7.98 | 0.93 | | | |
| 8 | 8.85 | 2.01 | 9.02 | 1.84 | 9.48 | 1.38 | 9.39 | 1.47 | | | |
| 9 | 7.92 | 2.08 | 7.90 | 2.09 | 8.09 | 1.90 | 7.96 | 2.03 | | | |
| 10 | 8.93 | 2.37 | 9.13 | 2.16 | 8.86 | 2.43 | 8.67 | 2.63 | | | |
| 11 | 6.78 | 2.38 | 6.78 | 2.38 | 6.61 | 3.55 | 6.43 | 2.73 | | | |
| 12 | 8.46 | 2.24 | 8.53 | 2.18 | 9.29 | 1.41 | 9.20 | 1.50 | | | |
| 13 | 8.10 | 3.03 | 8.55 | 2.58 | 9.19 | 1.99 | 9.07 | 2.06 | | | |
| 14 | 8.71 | 2.12 | 8.69 | 3.13 | 8.99 | 1.83 | 8.68 | 2.14 | | | |
| 15 | 7.04 | 3.58 | 7.64 | 2.98 | 7.33 | 3.30 | 6.98 | 3.64 | | | |
| 16 | 7.76 | 1.95 | 8.08 | 1.63 | 8.02 | 1.69 | 7.78 | 1.93 | | | |
| 17 | 8.75 | 2.63 | 8.39 | 2.98 | 9.06 | 2.33 | 8.98 | 2.39 | | | |
| 18 | 7.68 | 3.35 | 7.88 | 3.15 | 7.62 | 3.41 | 7.58 | 3.44 | | | |
| 19 | 7.78 | 3.13 | 8.19 | 2.73 | 8.23 | 2.68 | 7.96 | 2.96 | | | |
| 20 | 6.34 | 3.93 | 6.79 | 3.48 | 5.04 | 5.23 | 4.86 | 5.41 | | 20.50% | 23.39% |
| 21 | 8.96 | 2.88 | 9.33 | 2.50 | 9.39 | 2.44 | 9.03 | 2.80 | | | |
| 22 | 7.86 | 3.48 | 8.31 | 3.03 | 8.47 | 2.87 | 8.26 | 3.08 | | | |
| 23 | 7.36 | 2.58 | 7.35 | 2.82 | 7.73 | 2.43 | 7.58 | 2.58 | | | |
| 24 | 7.79 | 2.15 | 7.93 | 2.02 | 8.03 | 1.91 | 7.90 | 2.04 | | | |
| 25 | 7.66 | 3.31 | 7.81 | 3.16 | 7.66 | 3.31 | 7.36 | 3.61 | | | |
| 26 | 9.23 | 1.30 | 9.22 | 1.31 | 5.39 | 5.13 | 9.03 | 1.49 | | 41.55% | |
| 27 | 7.61 | 2.86 | 7.63 | 2.84 | 7.80 | 2.67 | 7.73 | 2.74 | | | |
| 28 | 8.63 | 2.06 | 8.47 | 2.23 | 6.38 | 4.32 | 6.36 | 4.33 | | 26.16% | 26.35% |
| 29 | 7.53 | 2.95 | 7.41 | 3.07 | 7.94 | 2.53 | 7.68 | 2.80 | | | |
| 30 | 9.69 | 1.70 | 9.29 | 2.10 | 10.36 | 1.02 | 10.25 | 1.14 | | | |

FIG. 21 personalised cut-offs

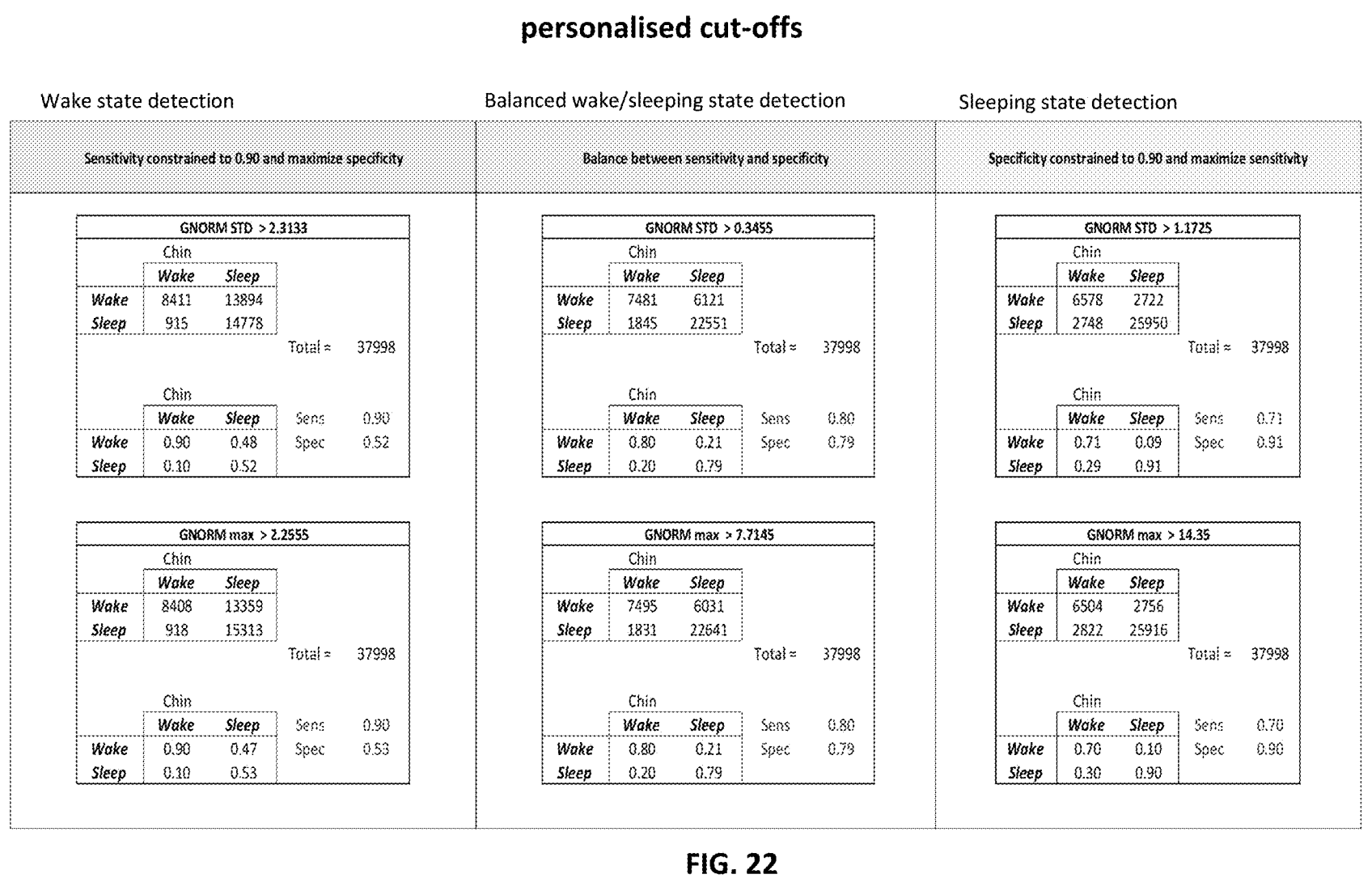

Wake state detection
Sensitivity constrained to 0.90 and maximize specificity

GNORM STD > 2.3133

| Chin | Wake | Sleep |
|------|------|-------|
| Wake | 8411 | 13894 |
| Sleep | 915 | 14778 |

Total ≈ 37998

| Chin | Wake | Sleep |
|------|------|-------|
| Wake | 0.90 | 0.48 |
| Sleep | 0.10 | 0.52 |

Sens 0.90
Spec 0.52

GNORM max > 2.2555

| Chin | Wake | Sleep |
|------|------|-------|
| Wake | 8408 | 13359 |
| Sleep | 918 | 15313 |

Total ≈ 37998

| Chin | Wake | Sleep |
|------|------|-------|
| Wake | 0.90 | 0.47 |
| Sleep | 0.10 | 0.53 |

Sens 0.90
Spec 0.53

Balanced wake/sleeping state detection
Balance between sensitivity and specificity

GNORM STD > 0.3455

| Chin | Wake | Sleep |
|------|------|-------|
| Wake | 7481 | 6121 |
| Sleep | 1845 | 22551 |

Total ≈ 37998

| Chin | Wake | Sleep |
|------|------|-------|
| Wake | 0.80 | 0.21 |
| Sleep | 0.20 | 0.79 |

Sens 0.80
Spec 0.79

GNORM max > 7.7145

| Chin | Wake | Sleep |
|------|------|-------|
| Wake | 7495 | 6031 |
| Sleep | 1831 | 22641 |

Total ≈ 37998

| Chin | Wake | Sleep |
|------|------|-------|
| Wake | 0.80 | 0.21 |
| Sleep | 0.20 | 0.79 |

Sens 0.80
Spec 0.79

Sleeping state detection
Specificity constrained to 0.90 and maximize sensitivity

GNORM STD > 1.1725

| Chin | Wake | Sleep |
|------|------|-------|
| Wake | 6578 | 2722 |
| Sleep | 2748 | 25950 |

Total ≈ 37998

| Chin | Wake | Sleep |
|------|------|-------|
| Wake | 0.71 | 0.09 |
| Sleep | 0.29 | 0.91 |

Sens 0.71
Spec 0.91

GNORM max > 14.35

| Chin | Wake | Sleep |
|------|------|-------|
| Wake | 6504 | 2756 |
| Sleep | 2822 | 25916 |

Total ≈ 37998

| Chin | Wake | Sleep |
|------|------|-------|
| Wake | 0.70 | 0.10 |
| Sleep | 0.30 | 0.90 |

Sens 0.70
Spec 0.90

FIG. 22

Wake state detection for personalised cut-off data

FIG. 23

Balanced sleep /wake state detection for fixed cut-off data

| # | Chin - data | | Cheek - data | | Cheek - SD | | Cheek - MAX | | Diff TST | Diff TST1 | Diff TST2 |
|---|---|---|---|---|---|---|---|---|---|---|---|
| | Sleep | Wake | Sleep | Wake | Sleep | Wake | Sleep | Wake | | | |
| 1 | 7.67 | 3.09 | 7.76 | 2.98 | 6.80 | 3.96 | 6.61 | 3.95 | 1.5% | 11.9% | 11.2% |
| 2 | 6.17 | 3.38 | 6.03 | 3.52 | 5.55 | 3.99 | 5.53 | 4.02 | 2.0% | 10.0% | 10.4% |
| 3 | 8.43 | 1.65 | 8.48 | 1.60 | 7.17 | 2.92 | 7.10 | 2.98 | 0.5% | 15.02% | 15.81% |
| 4 | 8.27 | 2.42 | 8.58 | 2.10 | 6.75 | 3.93 | 6.89 | 3.79 | 3.8% | 18.35% | 16.63% |
| 5 | 8.03 | 2.04 | 7.98 | 2.09 | 5.91 | 4.17 | 5.88 | 4.19 | 0.62% | 26.45% | 26.76% |
| 6 | 7.08 | 3.86 | 8.33 | 2.61 | 6.36 | 4.58 | 6.38 | 4.56 | 17.65% | 10.24% | 9.6% |
| 7 | 7.67 | 1.24 | 7.43 | 1.48 | 6.28 | 2.69 | 6.20 | 2.71 | 3.1% | 18.04% | 19.13% |
| 8 | 8.85 | 2.01 | 9.02 | 1.84 | 7.08 | 3.76 | 7.14 | 3.72 | 1.8% | 20.06% | 19.30% |
| 9 | 7.92 | 2.08 | 7.90 | 2.09 | 7.00 | 2.99 | 6.97 | 3.03 | 0.1% | 11.56% | 12.00% |
| 10 | 8.93 | 2.37 | 9.13 | 2.16 | 7.88 | 4.22 | 7.08 | 4.22 | 2.3% | 20.73% | 20.73% |
| 11 | 6.78 | 2.38 | 6.78 | 2.38 | 5.72 | 3.44 | 5.68 | 3.48 | 0.1% | 15.63% | 16.11% |
| 12 | 8.46 | 2.24 | 8.59 | 2.18 | 7.19 | 3.51 | 7.17 | 3.53 | 0.7% | 14.98% | 15.27% |
| 13 | 8.10 | 3.03 | 8.55 | 2.58 | 7.13 | 4.00 | 7.17 | 3.96 | 5.6% | 12.66% | 11.66% |
| 14 | 8.71 | 2.12 | 8.69 | 2.13 | 7.70 | 3.13 | 7.70 | 3.13 | 0.1% | 11.56% | 11.56% |
| 15 | 7.04 | 3.59 | 7.64 | 2.98 | 6.70 | 3.93 | 6.68 | 3.95 | 8.5% | 4.66% | 5.3% |
| 16 | 7.76 | 1.95 | 8.08 | 1.63 | 6.80 | 3.71 | 6.04 | 3.67 | 4.0% | 22.66% | 22.13% |
| 17 | 8.75 | 2.63 | 8.39 | 2.98 | 7.64 | 3.73 | 6.58 | 3.79 | 4.4% | 12.67% | 12.3% |
| 18 | 7.68 | 3.35 | 7.88 | 3.15 | 7.26 | 3.77 | 7.27 | 3.76 | 2.6% | 9.46% | 9.5% |
| 19 | 7.78 | 3.13 | 8.19 | 2.73 | 7.10 | 3.82 | 7.19 | 3.73 | 5.2% | 8.79% | 7.6% |
| 20 | 6.34 | 3.93 | 6.79 | 3.48 | 5.97 | 4.30 | 5.94 | 4.33 | 7.1% | 9.5% | 6.5% |
| 21 | 8.96 | 1.88 | 9.33 | 2.50 | 7.79 | 4.04 | 7.83 | 4.00 | 4.1% | 13.02% | 10.5% |
| 22 | 7.86 | 3.48 | 8.31 | 3.03 | 7.17 | 4.17 | 7.13 | 4.20 | 5.7% | 6.86% | 9.2% |
| 23 | 7.58 | 2.58 | 7.35 | 2.82 | 6.88 | 3.09 | 6.88 | 3.29 | 3.0% | 9.34% | 9.34% |
| 24 | 7.79 | 2.15 | 7.93 | 2.03 | 6.48 | 3.46 | 6.59 | 3.35 | 1.7% | 16.79% | 15.40% |
| 25 | 7.66 | 3.31 | 7.81 | 3.16 | 7.37 | 3.60 | 7.31 | 3.66 | 1.5% | 3.81% | 4.57% |
| 26 | 9.23 | 1.30 | 9.22 | 1.31 | 6.08 | 4.45 | 6.58 | 3.94 | 0.0% | 34.15% | 28.64% |
| 27 | 7.61 | 2.88 | 7.63 | 2.84 | 7.23 | 3.23 | 7.23 | 3.24 | 0.2% | 4.55% | 5.0% |
| 28 | 8.63 | 2.06 | 8.47 | 2.23 | 6.53 | 4.16 | 6.57 | 4.13 | 1.9% | 24.32% | 23.34% |
| 29 | 7.53 | 2.95 | 7.41 | 3.07 | 6.18 | 4.29 | 6.17 | 4.31 | 1.5% | 17.83% | 18.05% |
| 30 | 9.69 | 1.70 | 9.29 | 2.10 | 7.23 | 4.17 | 7.36 | 4.13 | 4.1% | 25.45% | 25.11% |

FIG. 24

Sleeping state detection for personalised cut-off data

SYSTEMS AND METHODS FOR A WEARABLE DEVICE FOR IMPROVING SLEEP

CROSS-REFERENCE TO RELATED APPLICATIONS

This application is a continuation-in-part of U.S. patent application Ser. No. 17/821,447, filed Aug. 22, 2022, now U.S. Pat. No. 11,752,327, which is a continuation application of PCT/EP2021/077190, filed on Oct. 1, 2021, which claims priority to EP Patent Application Serial No. 20199684.0, filed Oct. 1, 2020, the entire contents of each of which are incorporated herein by reference.

FIELD OF THE INVENTION

The present disclosure is in the field of sleep and respiratory care. In particular, the present disclosure provides means and methods for decreasing the respiratory effort of a subject during sleep. The present disclosure may also provide means and methods for treating the snoring of a subject during sleep.

BACKGROUND

Sleep disturbed breathing (SDB) marked with increased respiratory effort is a condition affecting sleep quality and causing excessive daytime sleepiness which contributes to most of road traffic accidents. Continuous positive airway pressure (CPAP) is the most effective treatment for SDB; however, long-term adherence is limited. There is an urgent need for new therapeutic approaches and easy to use systems on a large scale.

Electrical stimulation for the treatment of SDB occurring in the upper airways during sleep has been investigated. The genioglossus, which is the constitutive muscle of the tongue, was considered like the main dilator muscle of the upper airway for specific targeting. Previous trials aimed to target the tongue to move it to a more anterior position in the oral cavity, either unilaterally or bilaterally for more symmetrically movement of the tongue. It was confirmed that the unilateral stimulation of the tongue through an implantable stimulator of the hypoglossal nerve may effectively decrease respiratory effort, but the related cost and invasiveness of the proposed treatment limit the applicability to serious cases only. Bilateral stimulation of the tongue trying to provide more symmetric muscular tone to the genioglossus and consequently to increase the upper airway patency more largely and consistently has been proposed. Until now the bilateral stimulation was examined with an implantable hypoglossal nerve stimulating technology.

However, the anatomy of the upper airway in sapiens hominid is complex, as is the function, required for mastication, swallowing, speech and respiration. Upper airway obstruction during sleep is more prevalent than in other primates because the human pharynx has no rigid support except at its cranial and caudal ends, where it is anchored to bone (in its upper side) and cartilage (larynx) caudally.

Therefore, the pharynx behaves in sleep like a collapsible tube during the process of respiration. On the other hand, most of the building muscles of the pharynx anchor directly or indirectly via the hyoid bone to the mandible, the other mobile bone human beings have. Targeting only the genioglossus to prevent the occurrence of respiratory disturbances, such as airway obstruction or collapse, and related increase in respiratory effort from the brainstem during sleep exposed to failure because pharynx can still collapse from other parts than the tongue. Indeed, until now, bilateral genioglossus stimulators could not exhibit significant physiological and clinical benefits in a large proportion of patients. There is therefore a need to remedy the issues and limitations of state of art treatments for SDB marked with respiratory effort.

SUMMARY OF THE INVENTION

As described above, there is a need to remedy the issues and limitations of state of art treatments for sleep disturbed breathing marked with respiratory effort (SDB). The present disclosure relates to means and methods for decreasing the respiratory effort of a sleeping subject and/or prevent the occurrence of sleep respiratory disturbances. In particular, the present disclosure aims to provide transcutaneous electrical stimulation to the masseter, pterygoid and/or temporalis muscles of a subject to adjust their contribution to the sleep respiratory activity and reduce the subject's respiratory effort during sleep. Further, the present disclosure aims to provide means and methods for retraining the subject's brain through the provided electrical stimulation to decrease the central respiratory drive of the masseter, pterygoid and/or temporalis muscles.

An aspect of the present disclosure relates to a wearable device for decreasing the respiratory effort of a subject during sleep, the device comprising:

at least one left electrode adapted to be positioned into electrical contact with a selected portion of the subject's skin ranging from a left masseter, pterygoid and/or temporalis muscle motor point to a left posterior angle of the mandible;

at least one right electrode adapted to be positioned into electrical contact with a selected portion of the subject's skin ranging from a right masseter, pterygoid and/or temporalis muscle motor point to a right posterior angle of the mandible;

a stimulator configured to apply a transcutaneous electrical stimulation between the left electrode and at least one left masseter, pterygoid and/or temporalis muscle and between the right electrode and at least one right masseter, pterygoid and/or temporalis muscle;

wherein the applied electrical stimulation promotes the contraction of said left and right stimulated masseter, pterygoid and/or temporalis muscles to controllably elevate the subject's mandible such that the upper airway is opened.

An aspect of the present disclosure relates to a wearable device for decreasing the respiratory effort of a subject during sleep, the device comprising:

at least one left bipolar electrode configured for mounting on a selected portion of the subject's skin corresponding with the position of at least one left target muscle including a left masseter, a left pterygoid and/or a left temporalis muscle, at least one right bipolar electrode configured for mounting on a selected portion of the subject's skin corresponding with the position of at least one right target muscle including a right masseter, a right pterygoid and/or a right temporalis muscle, wherein the bipolar electrodes comprise at least two electrically conductive elements, wherein a first electrically conductive element is configured for mounting on the target muscle's motor point and a second electrically conductive element is configured for mounting along the direction of the target muscle fibre;

a stimulator configured to generate a biphasic transcutaneous electrical stimulation to be applied between the two electrically conductive elements of bipolar electrodes; wherein said electrical stimulation promotes the contraction of the target muscles to controllably elevate the subject's mandible so that the respiratory effort can be decreased.

In an embodiment the electrical stimulation is a biphasic and discontinuous electrical current.

In an embodiment the electrical stimulation has a current intensity of at least 1 mA to at most 50 mA, 1 mA to 30 mA.

In an embodiment the electrical stimulation has a pulse frequency of at least 1 Hz to at most 100 Hz, 30 Hz to 50 Hz.

In an embodiment the electrical stimulation has a pulse width of at least 100 μs to at most 400 μs, 200 μs to 300 μs.

In an embodiment the electrical stimulation has a stimulation duration of at least 1 sec to at most 20 sec, 5 sec to 10 sec.

In an embodiment the stimulator is configured to generate said electrical stimulation in accordance with at least one stimulation program, wherein said stimulation program is configured to generate an electrical stimulation with a duty cycle that has a stimulation period of 1 sec to 20 sec and/or a rest period of 1 sec to 20 sec.

In an embodiment the stimulator is configured to generate said electrical stimulation in accordance with at least one stimulation program, wherein said stimulation program includes at least one muscle recruitment program configured to generate an electrical stimulation defined by the following stimulation parameters: a current intensity between 5 mA to 10 mA, preferably 6 mA to 10 mA; a frequency between 15 Hz to 50 Hz, preferably 25 Hz to 45 Hz, more preferably 30 Hz to 40 Hz; and a pulse width between 50 μs to 300 μs, preferably 225 μs to 275 μs, more preferably 200 μs to 250 μs.

In an embodiment the stimulator is configured to generate said electrical stimulation in accordance with at least one stimulation program, wherein said stimulation program includes at least one muscle rehabilitation program configured to generate an electrical stimulation defined by the following stimulation parameters: a current intensity between 1 mA to 4 mA, preferably 2 mA to 4 mA; a frequency between 15 Hz to 50 Hz, preferably 20 Hz to 45 Hz, more preferably 30 Hz to 40 Hz; and, a pulse width between 50 μs to 300 μs, preferably 225 μs to 275 μs, more preferably 200 μs to 250 μs.

In an embodiment the stimulator is configured to generate said electrical stimulation in accordance with at least one stimulation program, wherein said stimulation program includes at least one neuromuscular retraining program configured to generate an electrical stimulation defined by the following stimulation parameters: a current intensity between 1 mA to 4 mA, between 2 mA to 4 mA; a frequency between 50 Hz to 150 Hz, preferably between 70 Hz to 130 Hz, even more preferably 90 Hz to 110 Hz; and, a pulse width between 500 μs to 1000 μs, preferably between 600 μs to 900 μs, more preferably 700 μs to 800 μs. In an embodiment the stimulator is configured to set the current intensity according to an intensity determination programme, wherein the current intensity is adjusted to a value between the stimulation perception threshold and stimulation discomfort threshold.

In an embodiment the stimulator is configured to selectively increase the electrical stimulation intensity between at least two sleeping sessions; preferably increase the electrical stimulation by 1% to 25%.

In an embodiment the stimulator is configured to selectively increase the electrical stimulation intensity between each and every consecutive sleeping session; preferably increase the electrical stimulation by 1% to 25%.

In an embodiment the stimulator is configured to apply a time-limited electrical pre-stimulation current between the left and/or right electrode and the subject skin to reduce the skin impedance.

In an embodiment the stimulator is configured to apply a time-limited electrical pre-stimulation current between the left and/or right electrode and the subject skin, current which has a pulse width of about or below 100μ and/or a pulse frequency of about or above 100 Hz.

In an embodiment the inter electrode distance between at least two electrically conductive elements of at least one electrode is between 15 mm to 25 mm, preferably 16 mm to 24 mm, more preferably 17 mm to 23 mm, even more preferably 18 mm to 22 mm, even more preferably 19 mm to 21 mm, even more preferably about 20 mm.

In an embodiment the diameter of at least one electrically conductive element of at least one electrode is between 10 mm to 20 mm, preferably 11 mm to 19 mm, more preferably 12 mm to 18 mm, even more preferably 13 mm to 17 mm, even more preferably 14 mm to 16 mm.

In an embodiment the wearable device comprises a sensing unit configured for recording of mandibular movement of the subject and a processing unit operatively connected to said sensing unit; wherein the processing unit is configured to receive, from said sensing unit, mandibular activity data; and, determine, from the mandibular activity data, one or more mandibular features. In an embodiment the mandibular feature includes at least the position, rotation or displacement of the mandible.

In an embodiment the wearable device comprises a sensing unit configured for recording of mandibular movement of the subject and a processing unit operatively connected to said sensing unit; wherein the processing unit is configured to receive, from said sensing unit, mandibular activity data; and, determine, from the mandibular activity data, one or more mandibular features, preferably including at least a position, a rotation and/or a displacement of the subject's mandible and/or head.

In an embodiment the wearable device comprises a sensing unit that comprises at least one gyroscope and/or accelerometer configured for recording mandibular movement; wherein the sensing unit is mounted on the subject's mandible.

In an embodiment the wearable device comprises a sensing unit that is mounted on the left and/or right electrode; preferably on the left and/or right masseter muscle; preferably on the left and/or right electrode mounted on the left and/or right masseter muscle.

In an embodiment the processing is configured to receive, from said sensing unit, respiratory activity data; and, determine, from the respiratory activity data, one or more respiratory features. In an embodiment the respiratory feature includes at least a sleep disturbed breathing marked with increased respiratory effort and/or a sleep respiratory disturbance.

In an embodiment the processing unit is configured to determine from the respiratory activity data a stimulation response and compare said stimulation response with a desired response, the desired response consisting of a decrease in the respiratory effort of a sleeping subject; and to adjust at least one stimulation parameter if a difference between said stimulation response and said desired response is determined to effectuate the desired response. In an embodiment the desired response includes an adjusting of at least one stimulation parameter, preferably adjusting the current intensity.

In an embodiment the processing unit comprises a respiratory effort detection module configured to detect an increase in respiratory effort in the subject's mandibular activity data, preferably from one or more mandibular features, and adjust one or more stimulation parameters and/or stimulation programs to reduce respiratory effort.

In an embodiment said respiratory effort detection module, upon detection of an increase in respiratory effort, is configured to increase the current intensity by 10%, 20%, 30%, 40%, 50% or more, increase the stimulation period of the duty cycle by 10%, 20%, 30%, 40%, 50% or more, and/or decrease the rest period of the duty cycle by 10%, 20%, 30%, 40%, 50% or more.

In an embodiment said respiratory effort detection module, upon detection of a decrease in respiratory effort, is configured to decrease the current intensity by 10%, 20%, 30%, 40%, 50% or more, decrease the stimulation period of the duty cycle by 10%, 20%, 30%, 40%, 50% or more, and/or increase the rest period of the duty cycle by 10%, 20%, 30%, 40%, 50% or more.

In an embodiment the processing unit comprises a respiratory disturbance detection module configured to detect the presence of a respiratory disturbance in the subject's mandibular activity data, preferably from one or more mandibular features, and adjust one or more stimulation parameters and/or stimulation programs to reduce, preferably prevent, the occurrence of a respiratory disturbance.

In an embodiment said respiratory disturbance detection module, upon detection of a respiratory disturbance, is configured to increase the current intensity by 10%, 20%, 30%, 40%, 50% or more, increase the stimulation period of the duty cycle by 10%, 20%, 30%, 40%, 50% or more, and/or decrease the rest period of the duty cycle by 10%, 20%, 30%, 40%, 50% or more.

In an embodiment the processing unit comprises a muscle fatigue detection module configured to detect the presence of muscle fatigue in the subject's mandibular activity data, preferably from the one or more mandibular features, and adjust one or more stimulation parameters and/or stimulation programs to reduce muscle fatigue.

In an embodiment said muscle fatigue detection module, upon detection of muscle fatigue, is configured to decrease the current intensity by 10%, 20%, 30%, 40%, 50% or more, decrease the stimulation period of the duty cycle by 10%, 20%, 30%, 40%, 50% or more, and/or increase the rest period of the duty cycle by 10%, 20%, 30%, 40%, 50% or more.

In an embodiment said muscle fatigue detection module, upon detection of muscle fatigue, is configured to terminate the recruitment program and/or initiate the rehabilitation program.

In an embodiment said muscle fatigue detection module is configured to detect the presence of peripheric muscular or fibre fatigue; and, upon detection of peripheric muscular or fibre fatigue, adjust one or more stimulation parameters by reducing the current intensity, preferably by 10%, 20%, 30%, 40%, 50% or more; preferably by initiating a stimulation defined by one or more stimulation parameter including a decreased current intensity of the electrical stimulation.

In an embodiment said muscle fatigue detection module is configured to detect the presence of spinal or supraspinal fatigue; and, upon detection of spinal or supraspinal fatigue, adjust one or more stimulation parameters by increasing the frequency, preferably by 10%, 20%, 30%, 40%, 50% or more, and/or increasing the pulse width of the electrical stimulation, preferably by 10%, 20%, 30%, 40%, 50% or more; preferably by initiating a stimulation defined by one or more stimulation parameter including an increased frequency and/or increased pulse width of the electrical stimulation.

In an embodiment the processing unit is configured to receive, from said sensing unit, sleeping activity data; and determine, from the sleeping activity data, or more sleeping features. In an embodiment the mandibular feature includes at least a sleeping state and/or a sleeping stage of the subject.

In an embodiment the processing unit is configured to determine, from the sleeping activity data, the sleeping state of the subject, which sleeping state includes at least an awake state and/or an asleep state; and instruct the stimulator to initiate the electrical stimulation during the asleep state and/or to terminate the electrical stimulation during the awake state.

In an embodiment the processing unit is configured to determine, from the sleeping activity data, the sleeping stage of the subject, which sleeping stage includes at least a light sleeping (N1) stage, a light sleeping (N2) stage, a REM stage, and/or a deep sleeping (N3) stage; and instruct the stimulator to initiate the electrical stimulation during the light sleeping (N1 and/or N2) stage and/or REM stage, and/or to terminate the electrical stimulation during the deep sleeping (N3) stage.

In an embodiment the processing unit comprises a sleeping stage determination module configured to determine a sleeping stage of the subject including at least an awake state and asleep state, and adjust one or more stimulation parameters and/or stimulation programs when a change in sleeping stage is determined.

In an embodiment said sleeping stage determination module, upon detection of the awake stage, is configured to terminate the electrical stimulation and/or adjust one or more stimulation parameters and/or stimulation programs to reduce the stimulation efficiency; preferably by terminating the recruitment program and/or decreasing the current intensity by 10%, 20%, 30%, 40%, 50% or more, decreasing the stimulation period of the duty cycle by 10%, 20%, 30%, 40%, 50% or more, and/or increasing the rest period of the duty cycle by 10%, 20%, 30%, 40%, 50% or more.

In an embodiment said sleeping stage determination module, upon detection of the asleep stage, is configured to initiate the electrical stimulation and/or adjust one or more stimulation parameters and/or stimulation programs to increase the stimulation efficiency; preferably by initiating the recruitment program and/or increasing the current intensity by 10%, 20%, 30%, 40%, 50% or more, increasing the stimulation period of the duty cycle by 10%, 20%, 30%, 40%, 50% or more, and/or decreasing the rest period of the duty cycle by 10%, 20%, 30%, 40%, 50% or more.

In an embodiment said sleeping stage determination module is further configured to determine a light sleeping (N1 and/or N2) stage and/or REM stage; and, wherein, upon detection of the light sleeping (N1 and/or N2) stage and/or REM stage, said sleeping stage determination module is configured to initiate the electrical stimulation and/or adjust one or more stimulation parameters to increase the stimulation efficiency; preferably by increasing the current intensity by 10%, 20%, 30%, 40%, 50% or more, increasing the stimulation period of the duty cycle by 10%, 20%, 30%, 40%, 50% or more, and/or decreasing the rest period of the duty cycle by 10%, 20%, 30%, 40%, 50% or more.

In an embodiment said sleeping stage determination module is further configured to determine a light sleeping (N1 and/or N2) stage and/or REM stage; and, wherein, upon detection of the light sleeping (N1 and/or N2) stage and/or REM stage, said sleeping stage determination module is configured to initiate the recruitment program and/or terminate the retraining program.

In an embodiment said sleeping stage determination module is further configured to determine a deep sleeping (N3) stage; and, wherein, upon detection of the deep sleeping (N3) stage, said sleeping stage determination module is configured to adjust one or more stimulation parameters to decrease the stimulation efficiency; preferably by decreasing the current intensity by 10%, 20%, 30%, 40%, 50% or more, decreasing the stimulation period of the duty cycle by 10%, 20%, 30%, 40%, 50% or more, and/or increasing the rest period of the duty cycle by 10%, 20%, 30%, 40%, 50% or more.

In an embodiment said sleeping stage determination module is further configured to determine a deep sleeping (N3) stage; and, wherein, upon detection of the deep sleeping (N3) stage, said sleeping stage determination module is configured to terminate the recruitment program and/or initiate the retraining program.

In an embodiment the processing unit is configured to determine the sleeping state and/or stage by
dividing the mandibular activity data into epochs of a specific time; and,
applying a mathematical model to assign a sleeping state and/or sleeping stage to every epoch;
wherein said mathematical model comprises the step of
extracting at least one feature from the recorded mandibular movement data for every epoch;
tracking the value of said extracted feature across every epoch;
setting a feature specific threshold value; and,
adjusting the sleeping state and/or sleeping stage of an epoch if the extracted feature value exceeds the feature specific threshold value.

In an embodiment the sensing unit comprises at least one gyroscope configured for recording mandibular movement of the subject's mandible.

In an embodiment the sensing unit comprises at least one gyroscope, at least one accelerometer and optionally also at least one magnetometer.

In an embodiment the sensing unit is provided on the left and/or right electrode.

In an embodiment the wearable device comprises a collar for housing the stimulator; wherein the collar is adapted for placement around the subject's neck and/or onto the subject's shoulders.

In an embodiment the left and/or right electrode is connected to the collar with a connective cable, the length of which may be adjusted.

An aspect of the present disclosure relates to a method for mounting of an electrode on a selected portion of the subject's skin corresponding with the position of a masseter muscle, the method comprising the steps of:
(i) identifying the gonial angle (Go), preferably the corner angle of the mandible;
(ii) identifying the zygomatic arch (Za), preferably the outer corner of the eye;
(iii) identifying the masseter muscle extending from said gonial angle (Go) towards said zygomatic arch (Za);
(iv) identifying a target stimulation zone (S) on said masseter muscle, preferably ranging from the gonial angle (Go) up to about halfway the distance between the gonial angle (Go) and the zygomatic arch (Za) along the direction of the masseter muscle fibre; and,

(v) mounting the electrode on said target stimulation zone (S).

In an embodiment of the method for mounting the electrode is a bipolar electrode comprising two conductive surfaces, wherein the first electrically conductive element is mounted on the masseter muscle's motor point, preferably adjacent to the gonial angle (Go), and the second electrically conductive element is mounted along the direction of the masseter muscle fibre, preferably about halfway the distance between the gonial angle (Go) and the zygomatic arch (Za) along the direction of the masseter muscle fibre.

An aspect of the present disclosure relates to a method for decreasing the respiratory effort of a subject during said subject's sleep, the method comprising:
selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;
selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;
applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased; wherein said electrical stimulation is generated according to a duty cycle that has a stimulation period of 1 sec to 20 sec and/or a rest period of 1 sec to 20 sec.

An aspect of the present disclosure relates to a method for recruiting of a target muscle to decrease the respiratory effort of a subject during said subject's sleep, the method comprising:
selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;
selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;

applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased;

wherein said electrical stimulation is generated according to the following stimulation parameters: a current intensity between 5 mA to 10 mA, preferably 6 mA to 10 mA; a frequency between 15 Hz to 50 Hz, preferably 25 Hz to 45 Hz, more preferably 30 Hz to 40 Hz; a pulse width between 50 µs to 300 µs, preferably 225 µs to 275 µs, more preferably 200 µs to 250 µs; and, a duty cycle with a stimulation period of 1 sec to 20 sec and/or a rest period of 1 sec to 20 sec.

An aspect of the present disclosure relates to a method for rehabilitating the muscle function of a target muscle to decrease the respiratory effort of a subject during said subject's sleep, the method comprising:

selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;

selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;

applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased;

wherein said electrical stimulation is generated according to the following stimulation parameters: a current intensity between 1 mA to 4 mA, preferably 2 mA to 4 mA; a frequency between 15 Hz to 50 Hz, preferably 20 Hz to 45 Hz, more preferably 30 Hz to 40 Hz; a pulse width between 50 µs to 300 µs, preferably 225 µs to 275 µs, more preferably 200 µs to 250 µs; and, a duty cycle with a stimulation period of 1 sec to 20 sec and/or a rest period of 1 sec to 20 sec.

An aspect of the present disclosure relates to a method for retraining of a neuromuscular related circuit to decrease the respiratory effort of a subject during said subject's sleep, the method comprising:

selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;

selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;

applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased; wherein said electrical stimulation is generated according to the following stimulation parameters: a current intensity between 1 mA to 4 mA, between 2 mA to 4 mA; a frequency between 50 Hz to 150 Hz, preferably between 70 Hz to 130 Hz, even more preferably 90 Hz to 110 Hz; a pulse width between 500 µs to 1000 µs, preferably between 600 µs to 900 µs, more preferably 700 µs to 800 µs; and, a duty cycle with a stimulation period of 1 sec to 20 sec and/or a rest period of 1 sec to 20 sec.

A wearable device is provided herein for decreasing respiratory effort of a subject during sleep. The wearable device may include a housing designed to be worn on the subject's head and/or neck during sleep, a first electrode connected to the housing and positioned with respect to the housing such that the first electrode is mounted on the subject's skin and designed to transcutaneously stimulate a masseter muscle of the subject when the wearable device is worn by the subject, a second electrode connected to the housing and positioned with respect to the housing such that the second electrode is mounted on the subject's skin and designed to transcutaneously stimulate a pterygoid muscle of the subject when the wearable device is worn by the subject, and a stimulator coupled to the first electrode and the second electrode, the stimulator designed to cause the first electrode to transcutaneously stimulate the masseter muscle to cause the masseter muscle to contract and designed to cause the second electrode to transcutaneously stimulate the pterygoid muscle to cause the pterygoid muscle to contract, thereby elevating the subject's mandible to decrease respiratory effort during sleep.

The first electrode may be a bipolar electrode. The bipolar electrode may include first and second electrode portions each designed to be positioned on the subject's skin at the masseter muscle. The second electrode may be a bipolar electrode. The bipolar electrode may include first and second electrode portions each designed to be positioned on the subject's skin at the pterygoid muscle. The first electrode may be connected to the housing and positioned with respect to the housing such that the first electrode is designed to transcutaneously stimulate a right masseter muscle of the subject. The second electrode may be connected to the housing and positioned with respect to the housing such that the second electrode is designed to transcutaneously stimulate a right pterygoid muscle of the subject.

The wearable device may also include a third electrode connected to the housing and positioned with respect to the housing such that the third electrode is mounted on the subject's skin and designed to transcutaneously stimulate a left masseter muscle of the subject when the wearable device is worn by the subject, and a fourth electrode connected to the housing and positioned with respect to the housing such that the fourth electrode is mounted on the subject's skin and designed to transcutaneously stimulate a left pterygoid muscle of the subject when the wearable device is worn by the subject. The first, second, third, and fourth electrodes may each be bipolar electrodes including first and second electrode portions, and wherein the first and second electrode portions of the first electrode are each designed to be positioned on the subject's skin at the right masseter muscle, the first and second electrode portions of the second electrode are each designed to be positioned on the subject's skin at the right pterygoid muscle, the first and second electrode portions of the third electrode are each designed to be positioned on the subject's skin at the left masseter muscle, and the first and second electrode portions of the fourth electrode are each designed to be positioned on the subject's skin at the left pterygoid muscle.

The first and second electrodes may each comprise adhesive surfaces designed to be adhered to the subject's skin. The housing may include a collar designed to be worn on the subject's neck during sleep. The stimulator may be designed to cause the first electrode and the second electrode to transcutaneously stimulate simultaneously. The stimulator is designed to cause the first electrode and the second electrode to transcutaneously stimulate sequentially. The stimulator may be programmed with a stimulation regime wherein the stimulator causes transcutaneous stimulation to the first electrode and the second electrode for a stimulation period followed by no stimulation for a rest period, wherein the stimulation period followed by the rest period is repeated throughout a sleep period of the subject. A sensing unit may include one or more of an accelerometer or a gyroscope designed to sense movement of the subject's mandible. The stimulator is designed to cause the first electrode to transcutaneously stimulate the masseter muscle and the second electrode to transcutaneously stimulate the pterygoid muscle responsive to movement of the subject's mandible sensed by the sensing unit. The housing comprises an adjustable strap designed to be adjusted to the subject's head and/or neck. The housing may wrap around a top of subject's head and beneath the subject's mandible.

A method is also provided for decreasing respiratory effort of a subject during sleep using a wearable device. The method may include providing the wearable device, which may include a housing designed to be worn on the subject's head and/or neck during sleep, first and second electrodes connected to the housing, and a stimulator connected the first and second electrodes, the first electrode positioned with respect to the housing such that the first electrode is mounted on the subject's skin and designed to transcutaneously stimulate a masseter muscle of the subject when the wearable device is worn by the subject, and the second electrode positioned with respect to the housing such that the second electrode is mounted on the subject's skin and designed to transcutaneously stimulate a pterygoid muscle of the subject when the wearable device is worn by the subject, causing the stimulator to transcutaneously stimulate the masseter muscle via the first electrode to cause the masseter muscle to contract, and causing the stimulator to transcutaneously stimulate the pterygoid muscle via the second electrode to cause the pterygoid muscle to contract, wherein transcutaneously stimulating the masseter muscle and the pterygoid muscle elevates a mandible of the subject to decrease respiratory effort during sleep.

DESCRIPTION OF THE FIGURES

The following description of the figures of specific embodiments of the disclosure are merely exemplary in nature and is not intended to limit the present teachings, their application or uses.

Throughout the drawings, the corresponding reference numerals indicate the following parts and features: stimulation region (S); superficial masseter (SM); medial pterygoid (MP); anterior temporalis (AT); gonial angle (Go); zygomatic arch (Za); wearable device (10); electrode (100); electrically conductive element (110); connective cable (150); wearable garment (200), e.g., collar or headband.

FIG. 18 shows the cut-off configuration parameters for the fixed cut-off model as discussed in Example 6.

FIG. 19 shows a table with the data analysis algorithm configured for wake state detection of the fixed cut-off model as discussed in Example 6.

FIG. 20 shows a table with the data analysis algorithm configured for balanced wake/sleeping state detection of the fixed cut-off model as discussed in Example 6.

FIG. 21 shows a table with the data analysis algorithm configured for sleeping state detection of the fixed cut-off model as discussed in Example 6.

FIG. 22 shows the cut-off configuration parameters for the personalised cut-off model as discussed in Example 6.

FIG. 23 shows a table with the data analysis algorithm configured for wake state detection of the personalised cut-off model as discussed in Example 6.

FIG. 24 shows a table with the data analysis algorithm configured for balanced wake/sleeping state detection of the personalised cut-off model as discussed in Example 6.

FIG. 25 shows a table with the data analysis algorithm configured for sleeping state detection of the personalised cut-off model as discussed in Example 6.

DETAILED DESCRIPTION

Figure 1:
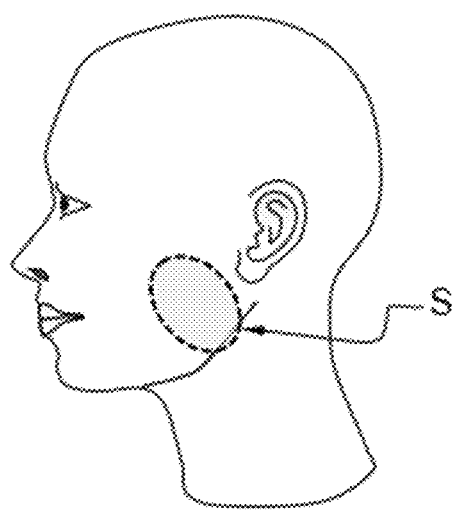
FIG. 1 is an illustration of the stimulation region (S) on a subject's skin for positioning of an electrode (100) according to a preferred embodiment of the present invention.

The present disclosure will be described with respect to particular embodiments, but the disclosure is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

The recitation of numerical ranges by endpoints includes all numbers and fractions subsumed within the respective ranges, as well as the recited endpoints.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the disclosure described herein are capable of operation in other sequences than described or illustrated herein.

Unless otherwise defined, all terms used in disclosing the invention, including technical and scientific terms, have the meaning as commonly understood by one of ordinary skill in the art to which this disclosure belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention, and form different embodiments, as would be understood by those in the art. For example, in the following claims and description, any of the claimed or described embodiments can be used in any combination.

The terms "left", "right", "front", "back", "top", "bottom", "over", "under", and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled", as used herein, is defined as directly or indirectly connected in an electrical or nonelectrical (i.e. physical) manner. Objects described herein as being "adjacent to" each other may be in physical contact with each other, in close proximity to each other, or in the same general region or area as each other, as appropriate for the context in which the phrase is used. Occurrences of the phrase "in one embodiment", or "in one aspect", herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

Reference in this specification may be made to devices, structures, systems, or methods that provide "improved" performance. It is to be understood that unless otherwise stated, such "improvement" is a measure of a benefit obtained based on a comparison to devices, structures, systems or methods in the prior art. Furthermore, it is to be understood that the degree of improved performance may vary between disclosed embodiments and that no equality or consistency in the amount, degree, or realization of improved performance is to be assumed as universally applicable.

In addition, it should be understood that embodiments of the present disclosure may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the present disclosure may be implemented in software (e.g., instructions stored on non-transitory computer-readable medium) executable by one or more processing units, such as a microprocessor and/or application specific integrated circuits ("ASICs"). As such, it should be noted that a plurality of hardware and software-based devices, as well as a plurality of different structural components may be utilized to implement the invention. For example, "servers" and "computing devices" described in the specification can include one or more processing units, one or more computer-readable medium modules, one or more input/output interfaces, and various connections (e.g., a system bus) connecting the components.

As described above, there is a need to remedy the issues and limitations of state of art treatments for sleep disturbed breathing marked with respiratory effort (SDB). The present disclosure relates to means and methods for decreasing the respiratory effort of a sleeping subject and/or prevent the occurrence of sleep respiratory disturbances. In particular, the present disclosure aims to provide transcutaneous electrical stimulation to muscles controlling the movement of the mandible of a subject to adjust their contribution to the sleep respiratory activity and reduce the subject's respiratory effort during or after sleep.

The electrical stimulation to the muscles may be applied during a session with a time limit, which will be referred to as the stimulation session throughout the present disclosure. The stimulation session according to the present disclosure may be configured for effectuating a therapeutic effect, for instance to reduce the occurrence of sleep respiratory disorders or sleep-disordered breathing, or it may be configured for non-therapeutic purposes, such as a reduction of snoring or sleep related noises, or improving the sleeping quality. The time limit of the session may be predetermined or variable.

Accordingly, the present disclosure relates to wearable devices for providing a transcutaneous electrical stimulation to muscles controlling the movement of the mandible of a subject to decrease the respiratory effort of said subject during sleep and/or prevent the occurrence of sleep respiratory disturbances. Further, the present disclosure aims to provide for a retraining of the subject's brain through the provided electrical stimulation to decrease the central respiratory drive of the stimulated muscles.

Further, the disclosure also relates to wearable devices to monitor a stimulation response of a sleeping subject, in response to a transcutaneous electrical stimulation provided by the herein disclosed wearable devices for providing a transcutaneous electrical stimulation. The wearable device may be configured to determine the stimulation response directly through a physiological response of the sleeping subject to the electrical stimulation, or indirectly through an effect effectuated by the electrical stimulation, such as a reduction of the subject's respiratory effort and/or occurrence of sleep respiratory disturbances.

Further, the disclosure also relates to wearable devices to monitor a respiratory activity of a sleeping subject. The wearable device may be configured to determine sleep disturbed breathing marked with increased respiratory effort and/or the occurrence of a sleep respiratory disturbance. The wearable devices to monitor a respiratory activity of a sleeping subject may be linked or combined with the wearable devices for providing a transcutaneous electrical stimulation as described herein.

Further, the disclosure also relates to wearable devices to monitor a sleeping activity of a sleeping subject. The wearable device may be configured to determine a sleep state of a subject, which may include an awake state and an asleep state, and/or a sleep stage of a sleeping subject, which may include a light sleeping (N1) stage, a light sleeping (N2) stage, a REM stage, and/or a deep sleeping (N3) stage. The wearable devices to monitor a sleeping activity of a sleeping subject may be used to adjust the transcutaneous electrical stimulation The wearable devices to monitor a sleeping activity of a sleeping subject may be linked or combined with the wearable devices for providing a transcutaneous electrical stimulation as described herein.

Selective electrical stimulation of muscles controlling the movement of the mandible may allow for the mandible to be controllably moved into an elevated and anterior position and subsequently stabilized in said elevated and anterior position during subject sleep. The mandible can be used as a lever to stiffen the whole pharyngeal musculature which anchors to the mandibular arch and controls the opening of the upper airways. By finely adjusting the position of the mandible, the relationship between the muscular fibre tension and its length can be controlled, as well the relationship between the fibre force and its velocity. The genioglossus muscle anchors itself to the elevated position of the mandible and may thus further contribute to the opening of the upper airways. Also, the attached muscles may elevate the hyoid bone to a more advanced and upper position. The functional result is a dilation of the pharynx to substantially open the upper airways and instruct the brain to decrease the necessary level of respiratory effort.

Figure 2:
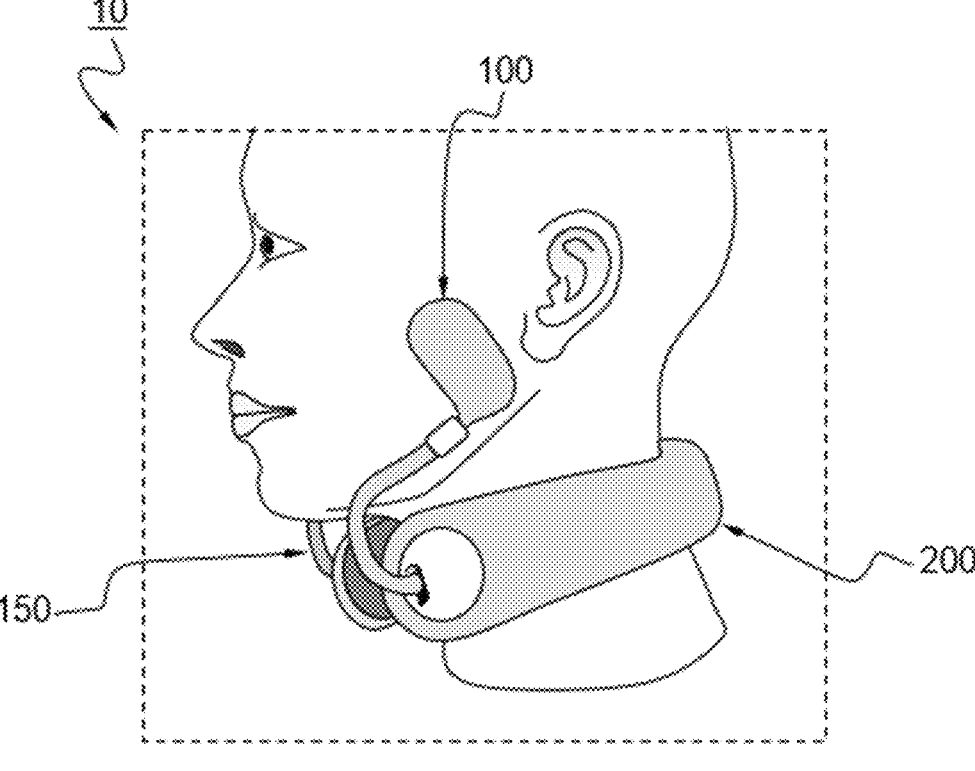
FIG. 2 is a schematic drawing of the wearable device (10) configured for stimulation of masseter muscles according to a preferred embodiment of the present invention.
Figure 5:
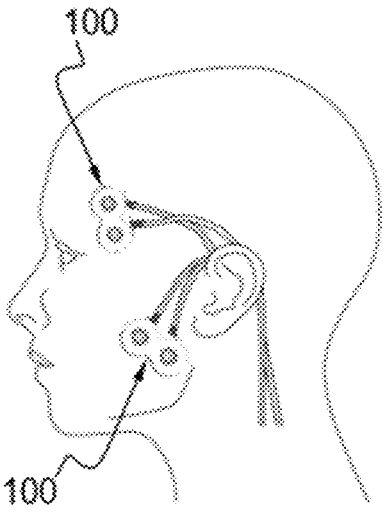
FIG. 5 is a perspective view of the wearable device (10) configured for stimulation of masseter and/or temporalis muscles according to another preferred embodiment of the present invention.
Figure 6:
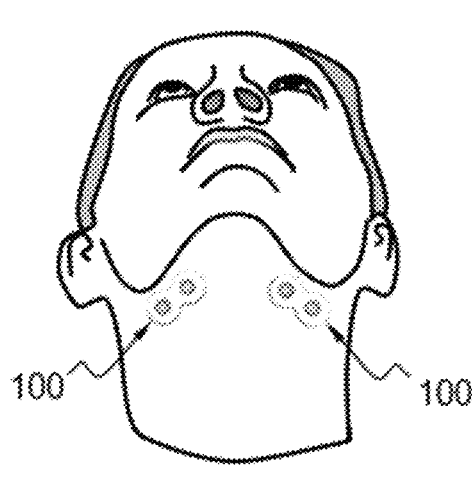
FIG. 6 is a perspective view of the wearable device (10) configured for stimulation of pterygoid muscles according to another preferred embodiment of the present invention.

Muscles for controlling the movement of the mandible may include the elevator muscles (i.e., muscles which contraction raises the position of the mandible), which includes the masseter, temporalis, medial pterygoid and superior belly of the lateral pterygoid, and/or the depressor muscles (i.e., muscles which contraction lowers the position of the mandible), which includes the anterior digastric, geniohyoid, mylohyoid and inferior belly of the lateral pterygoid. It is understood that any references to electrical stimulation of "muscles" as used herein refers to a stimulation of the listed elevator and/or depressor muscles. An embodiment of the present disclosure may provide for a stimulation of a single muscle type, for example only the masseter muscle, only the pterygoid muscle or only the temporalis muscle. An example of masseter muscle only stimulation is shown in FIG. 2, and an example of pterygoid muscle only stimulation is shown in FIG. 6. Another embodiment of the present disclosure may provide for a dual stimulation of a two different muscle types, for example the masseter and the temporalis muscles, the masseter and the pterygoid muscles, the temporalis and the pterygoid muscles, or the masseter and temporalis and pterygoid muscles, either sequentially or simultaneously, to effectuate the mandibular elevation and stabilisation. An example of dual masseter and temporalis muscle stimulation is shown in FIG. 5. Another embodiment of the present disclosure may provide for a triple stimulation of a three different muscle types, for example the masseter, temporalis and pterygoid muscles, either sequentially or simultaneously, to effectuate the mandibular elevation and stabilisation.

The electrical stimulation on the muscles for controlling the movement of the mandible may also provide for secondary effects on the other muscles connecting to the mandible. For instance, the genioglossus is anchored to the mental spines (on the internal face of the median line of the gnathion, the bony point on which the genioglossus hangs) at the inner side of the gnathion—by consequence when moving the mandible during elevation, the stimulation according to the present disclosure changes the spatial position of the anterior attachment point of the genioglossus. This may change the resting length of the genioglossus fibres by traction, a condition well known to induce a contraction of the anchored fibres (myotatic reflex). The risk of dry tongue is minimal when mouth is closed. Choking and gasping are avoided because the tongue is kept at an anterior location in the oral cavity.

Further, about the oral floor musculature (mylohyoid— geniohyoid—anterior belly of the digastric): when elevated, the mandible develops a leverage action on the oral floor muscles and these muscles become able to contract and to stiffen the upper airways while the hyoid bone position is regulated by other posterior and inferior muscles. Basically, the mandible is a mobile bone with several upper airway muscle attachments originating from surrounding locations. The mandible moves in response to active muscle contraction. This movement results in transfer of applied loads originating from one direction to other regions throughout the upper airway. The masseter displaces the mandible to an upper and forward position, and this enables also the other mobile hyoid bone to improve upper airway patency. These muscles attached directly or indirectly to the mandible are in a complex and intricate relationship with the final objective during sleep to ensure the local airflow circulation while diaphragm is going to constrict and create in the upper airway a sub atmospheric pressure.

It has been discovered that stimulation of the masseter, pterygoid and/or temporalis muscles are particularly effective for controlling and stabilising the elevation of the mandible and hence form a preferred embodiment of the present disclosure, specifically stimulation of the superficial masseter (sm), the medial pterygoid (mp) and the anterior temporalis (at). To elaborate, the masseter, pterygoid and/or temporalis muscles are specifically dedicated to the elevation of the mandible and therefore the mouth closing. These muscles are highly specialized and trained to perform this task. They are performant in endurance and in resistance due to their particular fibre muscular isoforms that are not present in the other groups of muscles in the human body. They are also involved in other important living functions: mastication, swallowing and speaking. When the masseter and/or the temporalis are stimulated, neurons develop in its representation area on the motor cortex as with the tongue— motor learning (neuroplasticity induced in corticomotor control of jaw muscles—cortical neuroplasticity is the ability of the brain to enhance a special skill with practice and to adapt or compensate for changes in sensory input).

Additionally, focusing the stimulation on the masseter, pterygoid and/or temporalis muscles only may reduce the discomfort experienced by the subject and decrease the build-up of muscle fatigue. These effects may for example be observed in stimulation focusing on too many different muscles at the same time and/or focusing on muscles that are considering as discomforting and/or easily fatigable, such the tongue. Accordingly, exclusive stimulation of the masseter, pterygoid and/or temporalis muscles form another preferred embodiment of the present disclosure.

There are different methods for effectuating electrical stimulation of the muscles, each method provoking a unique physiological response that may result in different technical effects and advantages. At least three different methods for effectuating electrical stimulation are contemplated in the present disclosure, specifically, recruiting the muscular fibres, rehabilitating the muscle function, and retraining the neuromuscular related circuit (through stimulation of the muscles).

To elaborate, recruiting the muscular fibres refers to a direct and acute muscle response to the electrical stimulation with directly measurable effects. Recruitment may hence be considered as a "basic" program for controlling the movement of the mandible during a stimulation session, but will typically not provide a persisting effect after the stimulation session has finished (i.e., when the stimulator is turned off).

Rehabilitating of the muscle function refers a training of the muscles through electrical stimulation that may improve the beneficial effects of the stimulation across successive stimulation sessions.

Rehabilitation may hence be considered as an "advanced" program that may provide for a delayed and advantageously persisting effect, but may require more than one, such as a plurality of successive stimulation sessions to achieve said effect.

Retraining of the neuromuscular related circuit refers to a central effect of the electrical stimulation on the central drive (directed on the central neural circuits involved in the breathing activity of the motor branch of the trigeminal nerve from the subject's brain) that is primarily aimed at achieving a persisting response after the stimulation session is finished or discontinued. Retraining may hence be considered as an "advanced" program that may provide for a persisting effect after the stimulation session has finished (i.e., when the stimulator is turned off), but may require more than one, such as a plurality of successive stimulation sessions to achieve said effect.

It may be appreciated that this initial overview of the stimulation methods is only intended to aid readers in understanding the difference between the methods more quickly. Specific embodiments for each method, for example in the form of programs to be executed by the herein disclosed stimulator, will be discussed throughout the present disclosure.

During general stimulation, the present disclosure may provide for a regulatory process of the central respiratory drive to reduce active effort needed for respiration and consequently relieve the sleeping subject from a harmful sympathetic stress provoked by respiratory disturbances. Further, the present disclosure may provide for a retraining process for the central respiratory drive to decrease the natural drive of the muscles and restore respiratory ventilation, which benefits may persist after stimulation. These processes may also provide for improvement in airflow, $SpO_2$, noise, orofacial dyskinesias, etc. Accordingly, the present disclosure can be applied for treatment of various disorders related to sleep disturbed breathing marked with respiratory effort (SDB), such as airway obstruction or collapse. Additionally, the device may aid in alleviating the occurrence and/or intensity of snoring.

Mandibular elevation effectuated by the present disclosure may open the upper airways or upper respiratory tract by increasing the upper airway width and/or reducing its collapsibility. The degree of mandibular elevation may be expressed as a % of maximum protrusive capacity or/and in millimetres (mm). Percentage of maximum protrusive capacity may be linked to potential side effects and percentage or millimetres to effectiveness in opening the upper airway. Exemplary protrusion positions may include 10% to 90% of the maximum mandibular protrusion.

It has been observed that recruiting and retraining of the muscles for controlling the movement of the mandible with "mild" transcutaneous electrical stimulation does not achieve adequate results. However, the present disclosure presents evidence that a sufficiently strong closing of the mandible for a sufficiently long period of time may provide improved short-term and/or long-term results. These results may be therapeutic in nature, for example by reducing the occurrence of sleep respiratory disorders or sleep-disordered breathing, or they may be non-therapeutic, for example by reducing the amount of sleep related noises or improving the sleeping quality. Advantageously, the short-term and/or long-term may be combined to achieve an efficient stimulation response by first recruiting the stimulated muscles and further retraining these stimulated muscles to improve the stimulation response and/or achieving persisting effects after termination of the stimulation. This way a synergistic effect can be achieved that goes beyond the benefits of local stimulation methods of the art.

Within the context of an electrical stimulation, "sufficiently strong closing" relates to the current intensity as experienced by the user at the beginning of the stimulation while in a quiet position just before falling asleep, as a spontaneous (not voluntary) tendency of mouth closure. The strength of the closing can be measured clinically by means of a force meter (min contractive force (F), min % of muscular fibres) or by mandible movement (change in amplitude, mandible position). Within the context of an electrical stimulation, "sufficiently long closing" relates to the time that the mandible is kept in a high and forward position that may ensure the air circulation. For example, the mandible can be elevated to close the mouth during the stimulation period of the duty cycle and then the mandibular jaw keeping elevated during the rest period of the duty cycle. The length of the closing can be measured clinically by means of an airflow meter (airflow amplitude (%)) or by mandible movement (time and frequency, mandible position). Measurement of the efficacy of the stimulation may be found discussed in Example 3.

An initial overview of various aspects of the disclosure is provided below and specific embodiments are then described in further detail. This initial overview is intended to aid readers in understanding the technological concepts more quickly, but is not intended to identify key or essential features thereof, nor is it intended to limit the scope of the claimed subject matter. The skilled person understands that the various aspects can be combined unless otherwise stated. As such, any specific embodiment of a specific aspect may be understood to constitute a specific embodiment of another aspect without the explicitly discussion thereof. For example, an embodiment of the device as described below also forms an embodiment for the manufacturing of said device, the use of said device, and so on.

An aspect of the present disclosure relates to a wearable device for decreasing the respiratory effort of a subject during sleep, the device comprising:

at least one left electrode adapted to be positioned into electrical contact with a selected portion of the subject's skin ranging from a left muscle motor point to a left posterior angle of the mandible;

at least one right electrode adapted to be positioned into electrical contact with a selected portion of the subject's skin ranging from a right muscle motor point to a right posterior angle of the mandible;

a stimulator configured to apply a transcutaneous electrical stimulation from the left electrode to at least one left muscle and from the right electrode to at least one right muscle; wherein the applied electrical stimulation promotes the contraction of said left and right stimulated muscles to controllably elevate the subject's mandible such that the upper airway is opened.

In an embodiment at least one left electrode may be adapted to be positioned into electrical contact with a selected portion of the subject's skin ranging from a left masseter, pterygoid and/or temporalis muscle motor point to a left posterior angle of the mandible and the stimulator is configured to apply a transcutaneous electrical stimulation from the left electrode to the at least one left masseter, pterygoid and/or temporalis muscle.

In an embodiment the at least one right electrode may be adapted to be positioned into electrical contact with a selected portion of the subject's skin ranging from a right masseter, pterygoid and/or temporalis muscle motor point to a right posterior angle of the mandible and the stimulator is configured to apply a transcutaneous electrical stimulation from the right electrode to the at least one right masseter, pterygoid and/or temporalis muscle.

The electrodes, preferably the left and right electrodes may deliver the electrical stimulation generated by the stimulator to the target muscles. According to an embodiment two or more electrodes may be provided, at least one for each side of the mandible, specifically the left and right electrode, such that the target muscles can be bilaterally stimulated.

In an embodiment the electrode may have an electrically conductive element with a diameter between 10 mm to 20 mm, preferably 11 mm to 19 mm, more preferably 12 mm to 18 mm, even more preferably 13 mm to 17 mm, even more preferably 14 mm to 16 mm, for example about 15 mm. Typically a circular electrically conductive element may be used, i.e., a conductive element with a circular surface area, but other geometrical shapes may also be contemplated, for example an oval element, square element, triangular element, etc. This may allow for covering the most prominent muscles bulk to achieve an efficient stimulation response. In another embodiment a diameter of 10 mm or lower can be used and still allow covering of the most prominent muscles bulk for targeted stimulation of smaller or more narrow muscles, such as the surface of the temporalis muscle.

Figure 10:
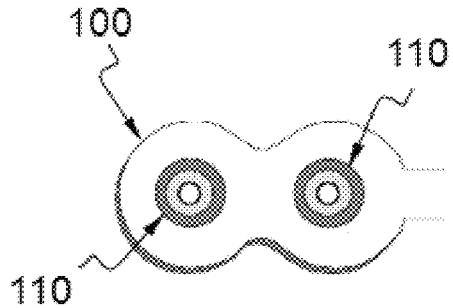
FIG. 10 is an illustration of a bipolar electrode (100) according to a preferred embodiment of the present invention.

In an embodiment the electrode may be a bipolar electrode, i.e., wherein each electrode comprises two electrically conductive elements that are applied between the target stimulation zone and the tendon. An example of a bipolar electrode with two adjacently disposed electrically conductive elements is shown in FIG. 10. The distance between the adjacent electrically conductive elements of the bipolar electrode is defined as the inter electrode distance. The inter electrode distance has an important impact on the comfort of the stimulation. If the comfort is improved, it may be possible for the patient to reach higher current intensities and thus improve the effectiveness of the treatment. In an embodiment the inter electrode distance may be between 10 mm to 30 mm, preferably 15 mm to 25 mm, preferably 16 mm to 24 mm, more preferably 17 mm to 23 mm, even more preferably 18 mm to 22 mm, even more preferably 19 mm to 21 mm, even more preferably about 20 mm. Typically a smaller inter electrode distance, for example 10 mm to 15 mm, may be selected for stimulation of smaller muscles and a larger inter electrode distance, for example 20 mm to 30 mm, may be selected for stimulation of larger muscles, such as the temporalis. Advantageously, the adjacent surface electrodes may be aligned with the muscle fibre direction to stimulate the same motor unit response twice but spatially shifted along the muscle.

In an embodiment the electrode can be repeatedly attached to the skin. Repeated attachment is advantageous for the device to be reusable over successive sleeping sessions. The electrodes are conveniently attached to stay in place during normal head and body movements. The electrodes may be provided with adhesive surfaces, which allow for easy attachment to the skin. Each electrode may be provided with a surface which is adapted for skin-dismountable attachment. Advantageously, each electrode may be configured to ensure electric conductivity such that comfort and effectiveness can be improved.

In an embodiment the electrode surface may be provided with an adhesive hydrogel to ensure a low resistive contact between the electrode and the skin. The electrode surface may be replaceable when the adhesive layer is worn out with repeated use, or alternatively, the adhesive layer may be replenished. In an alternative embodiment single use electrodes can be contemplated. In another embodiment electrodes provided with a single use, replaceable surface can be contemplated.

The stimulating means or as used herein "stimulator" may typically comprise a power source configured to generate an electrical current and a controller operatively connected to said power source. The controller may control the power source to generate electrical current according to the herein disclosed stimulation parameters to promote contraction of the stimulated muscles. The power source may be battery operated, such that the device can be freely worn during sleep. The electrodes can be connected to the stimulator by wires. Exemplary embodiments thereof are described further below.

The bilateral electrodes may provide simultaneous stimulation to the opposite left and right muscles. In some embodiments the provided stimulus along the left and right electrode may be equal. However, in other embodiments the stimulus along the left and right electrode may be different, such that different programs may be programmed according to the treatment type. The unequal stimulation may be performed using multiple controllers or a single controller configured to perform separate stimulations programs for the left and right electrode in accordance with differences in anatomy; for example a subject having a more defined muscle on one side of the mandible.

The controller may be configured for executing the herein presented methods. Embodiments may be implemented in code and may be stored on a storage medium having stored thereon instructions which can be used to program a system to perform the instructions. For purposes of the present disclosure, the terms "code" or "program" cover a broad range of components and constructs, including applications, drivers, processes, routines, methods, modules, and subprograms. The terms "code" or "program" may thus be used to refer to any collection of instructions which, when executed by a processing system, performs a desired operation or operations. Additionally, alternative embodiments may include processes that use fewer than all of the disclosed operations, processes that use additional operations, processes that use the same operations in a different sequence, and processes in which the individual operations disclosed herein are combined, subdivided, or otherwise altered. Those skilled in the art can implement the herein presented methods as a code or program and appreciate the numerous modifications and variations thereon.

The way the generated electrical current is used to transcutaneously stimulate the targeted muscles can be influenced by multiple factors. The use of continuous low current typically requires less force than intermittent stimulation as it is easier to maintain an opened upper airway than to initiate the reopening of an occluded airway. Nonetheless, it is beneficial to avoid continuous stimulation for prolonged periods as it may have adverse effects on muscle fatigue and the sleep quality. Accordingly, selection of the optimal stimulation parameters, including the current intensity (in mA), pulse frequency (in Hz), pulse width (in μs), and/or stimulation duration (e.g. continuous, intermittent, triggered), are important factors to promote efficient muscle response but avoid adverse effects. Additionally, selection of specific stimulation parameters may also provoke different physiological responses, specifically, recruiting the muscular fibres, rehabilitating the muscle function and retraining the neuromuscular related circuit (through stimulation of the muscles).

The electrical current may be applied in accordance with a regular stimulation pattern having a controlled rhythm to form a pulsed current. In an embodiment the electrical current is a biphasic electrical current characterized by one or more one stimulation parameters, such as the biphasic current intensity, pulse frequency, pulse width, and/or stimulation duration. Different combinations of signal parameters tend to suit different subjects according to subject specific factors, such as age, weight, skin type, etc. For example, biphasic current may be particularly suitable for recruiting, rehabilitating and/or retraining the muscles. However, as discussed above certain stimulation parameters risk inducing muscle fatigue or affecting the sleep quality. Below various stimulation parameters are listed which were found to provide a particularly good trade-off between high efficacy and risk of side effects.

In a general embodiment the current intensity may be selected between at least 1 mA to at most 50 mA, or 1 mA to 45 mA, or 1 mA to 40 mA, or 1 mA to 35 mA, more preferably 1 mA to 30 mA, or 1 mA to 25 mA, or 5 mA to 25 mA, even more preferably 10 mA to 20 mA, or 15 mA to 20 mA, or 10 mA to 15 mA. Variation in signal intensity may affect the muscle contraction force. The stimulation intensity may typically be the first stimulation parameters to be adjusted according to the subject's need and discomfort threshold.

In a general embodiment the pulse frequency may be selected between at least 1 Hz to at most 100 Hz, more preferably 10 Hz to 90 Hz, or 10 Hz to 85 Hz, or 10 Hz to 80 Hz, or 15 Hz to 75 Hz, or 15 Hz to 70 Hz, even more preferably 20 Hz to 60 Hz, or 25 Hz to 55 Hz, even more preferably 30 Hz to 50 Hz, even more preferably about 40 Hz such as 35 Hz to 45 Hz. Variation in signal frequency may affect the muscle contraction force. To achieve appropriate contraction suitable frequency may be selected within the broad range as indicated above and is more suitable within the preferred narrow ranges.

In a general embodiment the pulse width may be selected between at least 50 μs to at most 1000 μs, preferably 100 μs to 500 μs, or 100 μs to 400 μs, more preferably 125 μs to 375 μs, or 150 μs to 350 μs, or 175 μs to 325 μs, even more preferably 200 μs to 300 μs, even more preferably about 250 μs such as 225 μs to 275 μs. Variation in signal pulse width may affect the muscle contraction time. The signal pulse width can also be varied according to the subject's need and discomfort threshold.

The stimulation duration may be biphasic such that it consists of two repeating phases or period, specifically a stimulation period (i.e., "on" period) that is followed by a stimulation-free rest period (i.e., "off" period); the difference between the stimulation period and the rest defined as the duty cycle. In an embodiment the stimulation period may be between at least 1 sec to at most 20 sec, or 1 sec to 15 sec, or 1 sec to 10 sec, more preferably 2 sec to 8 sec, even more preferably 3 sec to 7 sec, even more preferably 4 sec to 6 sec, even more preferably 5 seconds. In an embodiment the rest period may be between at least 1 sec to at most 20 sec, or 1 sec to 15 sec, or 1 sec to 10 sec, more preferably 2 sec to 8 sec, even more preferably 3 sec to 7 sec, even more preferably 4 sec to 6 sec, even more preferably 5 seconds. The duration of the stimulation and rest period may be symmetrical, for example 5 sec of stimulation followed by 5 sec of rest, or asymmetrical, for example 5 sec of stimulation followed by 10 sec of rest, or 10 sec of stimulation followed by 5 sec of rest. The duration and/or relative ratio of the stimulation and rest periods may be adjusted towards a specific physiological effect. For example, the stimulation period may be increased and/or the rest period may be decreased to promote muscle stimulation. For example, the stimulation period may be decreased and/or the rest period may be increased to reduce muscle fatigue.

The above specified values provide general guidelines for selection of one or more stimulation parameters suitable for effectuating a physiological response from a sleeping subject. However, by selecting more specific stimulation parameters the physiological response may be steered towards a specific physiological effect. The skilled person may appreciate that these stimulation parameters may be executed by the herein disclosed wearable stimulation device in the form of executable stimulation programs. At least three different stimulation programs for effectuating electrical stimulation are contemplated in the present disclosure, specifically, recruiting the muscular fibres, rehabilitating the muscle function and retraining the neuromuscular related circuit. It is, however, understood that the wearable device of the present disclosure is not limited to only these three different stimulation programs.

In an embodiment the stimulation for recruiting of the muscular fibres, herein referred to as the "recruitment program", may comprise a transcutaneous electrical stimulation with a high current intensity at a low frequency with narrow pulse width (relative to the rehabilitation and retraining programs). The recruitment program aims to provide for a direct and acute muscle response with a directly measurable effect for controlling the movement of the mandible during a stimulation session, but will typically not provide a persisting effect after the stimulation session (i.e., when the stimulator is turned off).

The exact parameters of the recruitment program are subject specific; they depend on the subject's physical stimulation response and perceived degree of discomfort. In an embodiment the current intensity of the recruiting program may be selected between 5 mA to 10 mA, preferably between 6 mA to 10 mA, for example 7 mA, 8 mA or 9 mA. In an embodiment the frequency of the recruiting program may be selected between 10 Hz to 50 Hz, preferably between 15 Hz to 50 Hz, or 20 Hz to 50 Hz, or 25 Hz to 45 Hz, or 25 Hz to 45 Hz, or 30 Hz to 40 Hz, for example 30 Hz. In an embodiment the pulse width of the recruitment program may be selected between 25 μs to 300 μs, preferably between 50 μs to 275 μs, 50 μs to 250 μs, or 75 μs to 275 μs, or 100 μs to 275 μs, 125 μs to 275 μs, 150 μs to 275 μs, 175 μs to 275 μs, 200 μs to 275 μs, or 200 μs to 250 μs; for example 210 μs, 220 μs, 230 μs, 240 μs, or 250 μs.

In an embodiment the stimulation for rehabilitating the muscle function, herein referred to as the "rehabilitation program", may comprise a transcutaneous electrical stimulation with a low current intensity at a low frequency with narrow pulse width (relative to the recruitment and retraining programs). The rehabilitation program may aim improve the muscle function of the stimulated muscles, e.g. improving the contractive force and/or reducing the perceived degree of discomfort. The rehabilitation program may provide for an improved muscle response to the stimulation, which may improve the beneficial effects of the stimulation across multiple, preferably successive sessions.

The exact parameters of the rehabilitation program are subject specific; they depend on the subject's physical stimulation response and perceived degree of discomfort, for example if the subject suffered from a muscle or respiratory disease. In an embodiment the current intensity of the rehabilitation program may be selected between 1 mA to 4 mA, preferably between 2 mA to 4 mA, for example 3 mA. In an embodiment the frequency of the rehabilitation program may be selected between 10 Hz to 50 Hz, preferably between 15 Hz to 50 Hz, or 20 Hz to 50 Hz, or 25 Hz to 45 Hz, or 25 Hz to 45 Hz, or 30 Hz to 40 Hz, for example 30 Hz. In an embodiment the pulse width of the rehabilitation program may be selected between 25 μs to 300 μs, preferably between 50 μs to 275 μs, 50 μs to 250 μs, or 75 μs to 275 μs, or 100 μs to 275 μs, 125 μs to 275 μs, 150 μs to 275 μs, 175 μs to 275 μs, 200 μs to 275 μs, or 200 μs to 250 μs; for example 210 μs, 220 μs, 230 μs, 240 μs, or 250 μs.

In an embodiment the stimulation for retraining the neuromuscular circuit, herein referred to as the "retraining program", may comprise a transcutaneous electrical stimulation with a low current intensity at a higher frequency with wide pulse width (relative to the recruitment and rehabilitation programs). The retraining program may aim to retrain the neuromuscular related circuit to alter the central effect of the stimulation on the central drive, i.e., it is directed on the central neural circuits involved in the breathing activity of the motor branch of the trigeminal nerve from the subject's brain. The retraining program may achieve a persisting response after the session is terminated or even discontinued, but may require multiple, preferably successive session.

The exact parameters of the recruitment program are subject specific; they depend on the subject's physical stimulation response and perceived degree of discomfort, for example if the subject suffered from a muscle or respiratory disease. In an embodiment the current intensity of the retraining program may be selected between 1 mA to 4 mA, preferably between 2 mA to 4 mA, for example 3 mA. In an embodiment the frequency of the retraining program may be selected between 50 Hz to 150 Hz, preferably between 60 Hz to 140 Hz, or 70 Hz to 130 Hz, or 80 Hz to 120 Hz, or 90 Hz to 110 Hz, for example 100 Hz. In an embodiment the pulse width of the retraining program may be selected between 500 μs to 1000 μs, preferably between 550 μs to 950 μs, more preferably between 600 μs to 900 μs, even more preferably 650 μs to 850 μs, even more preferably 700 μs to 800 μs; for example 750 μs.

The stimulator may be configured to set the intensity of the electrical stimulation according to a stimulation intensity parameter; wherein the stimulation intensity parameter is determined according to the stimulation perception threshold and stimulation discomfort threshold. The current intensity for transcutaneous electrical stimulation may be dependent on the subject's sensitivity threshold and habituation. The optimal stimulation intensity may provide for a user personalized program to accommodate for subject specific parameters, such as variances in skin conductivity, muscle thickness, fat or adipose tissue thickness, and the like. In an embodiment, the current intensity of the electrical stimulation is adjusted to a value between the stimulation perception threshold and stimulation discomfort threshold. For example, the current intensity may be set halfway between the stimulation perception threshold and the stimulation discomfort threshold, i.e., half (½) of the sum of the stimulation perception threshold (in mA) and the stimulation discomfort threshold (in mA). Alternatively, the current intensity parameter may be set to quarter (¼) or three quarters (¾) between the stimulation perception threshold and the stimulation discomfort threshold according to the treatment type.

The stimulation intensity parameter may be determined via user input. In an embodiment, the stimulator may be configured for connecting to an input device, such as a smartphone, and receiving subject specific input from said input device. The input device may prompt the user to enter a stimulation perception threshold, which corresponds to the lowest intensity of the electrical stimulation at which the subject still perceives the electrical stimulation to promote contraction of the targeted muscles, and a stimulation discomfort threshold, which corresponds to the highest intensity of the electrical stimulation at which the subject perceives a degree of discomfort due to the pulsed electrical current, such as muscle pain, which could potentially affect the sleep quality.

The stimulator may be provided with a stimulation intensity determination programme configured to automatically determine the optimal stimulation intensity parameter. For example, the stimulator may set a predefined intensity based on subject specific parameters, such as age or sex, then gradually increase the current until the subject reports the occurrence of a perceived discomfort event, and then gradually decrease the current until the subject reports the lack of perceived stimulation. The stimulator may then calculate an optimal stimulation intensity parameter based on the reported discomfort and perception thresholds. Alternatively, the stimulator may also be selectively operable by a user to apply a stimulation intensity according to the user input. This may allow the user to quickly set-up the device if the optimal intensity parameter is already known, for example from a previous session. The skilled person may appreciate that a detection programme may also be provided for other stimulation parameters, such as the pulse frequency or width.

The stimulator may be configured to selectively increase the electrical stimulation intensity according to device and/or user feedback. Repeated sessions of transcutaneous electrical stimulation may reduce the muscle response over time thereby increasing the stimulation perception threshold. Also, the subject may also become habituated to the electrical stimulation thereby increasing the stimulation discomfort threshold. To avoid the need for user recalibration, the stimulator may be configured to automatically adjust the stimulation intensity between at least two sleeping session. Preferably, the stimulation intensity the stimulation intensity is adjusted between each and every consecutive two sleeping sessions. Alternatively, the stimulation intensity may be adjusted when specific treatment goals are met, such as a % reduction in snoring intensity or % increase in muscle strength. In an embodiment, the stimulator may automatically increase the stimulation intensity by a fixed rate, for example an increase of 1% to 25% with each sleeping session. Alternatively, the user may be prompted to manually adjust the stimulation intensity.

The stimulator may be configured to apply a pre-stimulation electrical current to improve the stimulated muscle response to the transcutaneous electrical stimulation. In particular, the stimulator may be configured to apply a time-limited high frequency electrical current from the left and/or right electrode to the subject skin to reduce the skin impedance. Skin typically presents a certain resistivity to the passage of the current which may be expected to decrease after a certain time. However, the electrical skin impedance of certain subject groups having more resistive skin, such as elderly or coloured, may require substantially more time for the skin resistivity drop to occur. Moreover, high resistivity means that the current is primarily established on the skin surface and generates unpleasant sensations.

It is therefore beneficial to reduce the skin impedance by performing pre-stimulation protocol to reduce skin impedance and ensure proper response of the muscle to the electrical stimulation. The pre-stimulation protocol may, for example, be applied when the device is first activated and/or right before a subject enters a targeted sleep cycle. In an embodiment the pre-stimulation protocol may be a pre-stimulation current with a low pulse width and high frequency (according for the power supply capabilities and subjects perceived discomfort threshold) for a limited time, such as one to five minutes. For example, the pre-stimulation current may be current with a pulse width of 100 μs and a pulse frequency of 100 Hz for which is applied by the electrode for one to two minutes.

The stimulator may determine and adjust the stimulation parameters via pre-set programmes provided on a memory device of the stimulator. Adhering to a pre-set programme may be suitable for embodiments wherein continuous stimulation is desired across the entire sleep cycle. Nonetheless, the stimulator may also be configured to provide stimulation based on data by a sensing unit.

The purpose of masseter, pterygoid and/or temporalis muscles stimulation is to position the jaw in such a way that normal breathing is realised and the respiratory effort is decreased. Hence, for optimal stimulation the electrode should advantageously be placed onto these muscles. Identification of these muscles can be difficult, especially for a non-medically trained subject for at home use of the wearable device. Nonetheless, a method for positioning of the electrodes on the superficial masseter and anterior temporalis muscles can be formulated based on the anatomical landmarks, specifically the zygomatic arch (Za) and gonial angle (Go). By using anatomical landmarks as references, a greater reproducibility can be ensured for positioning electrodes over the targeted muscles. Reproducibility of electrodes positioning may be advantageous for longitudinal stimulation to ensure the stimulation of a particular muscular portion location (spatial distribution of motor unit action potentials are not uniform through the whole extension of a muscle).

In an embodiment, a method for placement of electrodes on the masseter may comprise the steps of:

(i) identifying the gonial angle, preferably the corner angle of the mandible;

(ii) identifying the zygomatic arch, preferably the outer corner of the eye;

(iii) identifying the masseter muscle extending from said gonial angle towards said zygomatic arch;

(iv) identifying a target stimulation zone on said masseter muscle, preferably ranging from the gonial angle up to halfway the distance between the gonial angle and the zygomatic arch along the muscle fibre direction.

(v) optionally, placing an electrode according to the present disclosure on said target stimulation zone.

Figure 9:
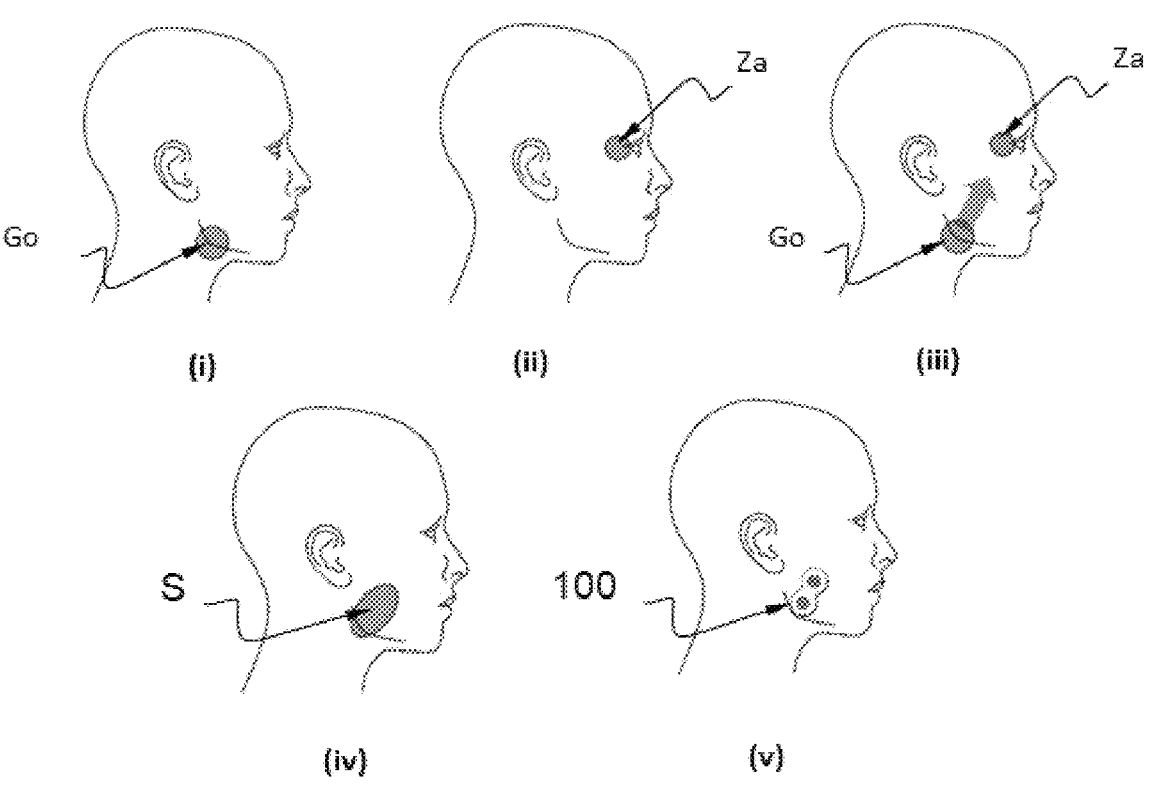
FIG. 9 is a placement guide illustrating a method for placement of the electrode (100) on the stimulation region (S) according to another preferred embodiment of the present invention.

In an embodiment the electrode the electrode is a bipolar electrode comprising two conductive surfaces, wherein the first electrically conductive element is mounted on the masseter muscle's motor point, preferably adjacent to the gonial angle, and the second electrically conductive element is mounted along the direction of the masseter muscle fibre, preferably halfway the distance between the gonial angle and the zygomatic arch along the muscle fibre direction. An example of the method for placement of an electrode on the masseter muscle is illustrated in FIG. 9.

Advantageously, the electrode can be placed on the muscle belly, the midpoint of a muscle or along the muscle fibres direction, as determined by palpation or visual observation. Nonetheless, different tissues between the electrodes-muscle interface present anisotropic characteristics, therefore it is desirable that electrodes are placed at the same direction as muscle fibres. This may allow a pair of electrodes to pick up a spread of action potentials from the same bundle of muscle fibres, and thus, of corresponding muscle volumes to promote stimulation efficiency.

Advantageously, the surface electrode can be placed along the muscle fibres, over the most prominent region at the moment of muscle contraction. Preferably, the electrode surface may be placed to be near the main motor neuron of the muscle (close to motor point of the muscle) such that the energy can dispatch along the length of the fibre, conducted by the axon of the motor neuron from the main motor point. By transferring the energy directly to the motor neuron, the electrode can reduce the dissipation of electric currents through the skin (the dermis) to other muscles of the head (e.g. orbicularis, labialis, etc.) that could contract and elevates the eyelid or the lip and others sensory endings causing discomfort such as paraesthesia.

It may be appreciated that the exact anatomy of the target muscles is unique and hence differs between subjects. Thus, any recommendation for surface electrodes positioning based on anatomical landmarks that are not closely related to the muscles of interest, or are not individualized, would not respect the precept that electrodes can advantageously be placed parallel to muscle fibres and over its largest volume. Surface electrodes, in a bipolar configuration, may advantageously be placed between the innervation zone and the tendinous insertion, depending directly on the anatomy of the muscle to be stimulated. The innervation zones of masseter, pterygoid and/or temporalis are typically widely dispersed, hampering electrodes placement over the recommended optimal anatomical region. Surface electrodes may be placed on one or two different locations that are based on easily palpable (use of palpation during muscle contraction) and specific anatomical references/landmarks (zygomatic arch and gonial angle) to guide the subject in their routine and guarantee the quality of the stimulation. This may further promote stimulation efficiency and reduce discomfort due to regional side effects.

The sensing unit or as used herein "sensor" may record data related to various activities of the subject, such as respiratory activity/effort and/or stimulation response. After recording, the sensing data may be processed by a processing unit, specifically a data analysis unit that is operatively connected to the stimulator, for example via a data link, or alternatively is part of the stimulator, such as the controller. This stimulator may for this purpose be adapted to receive feedback from the data analysis unit in the form of instructions to adjust the stimulation. The data link may be a wired or wireless connection.

Advantageously the sensor may be mounted on at least one electrode of the wearable device, such that the stimulation effects can be directly monitored. Nonetheless, the sensor may also be provided on another part the subject, such as the chin or chest, depending on which activity is to be measured and the degree of sensitivity. Below embodiments of sensors are contemplated that may be particularly suitable in combination with the present device for transcutaneous stimulation of the target muscles.

Advantageously, the sensing unit may be integrated into the wearable device for providing a transcutaneous electrical stimulation to muscles controlling the movement of the mandible of a subject to decrease the respiratory effort of said subject during sleep and/or prevent the occurrence of sleep respiratory disturbances. This has the advantage that data can be recorded during stimulation, reducing the chance for possible time delay or mismatching of stimulation programs. Also, the wearable device for monitoring and/or analysing respiratory activity of a sleeping subject may comprise an integrated sensing unit. Also, the wearable devices for monitoring and/or analysing sleeping activity of a sleeping subject may comprise an integrated sensing unit.

The wearable devices of the present disclosure may comprise a sensing unit configured for recording of mandibular and/or head movement of the subject and recording said movements as mandibular activity data that includes one or more mandibular features, such as a position, rotation or displacement of the subject's mandible and/or one or more head features, such as a position, rotation or displacement of the subject's head.

In an embodiment the mandibular activity data may also provide information on stimulation efficacy, specifically the muscle response of the subject to the applied stimulation, which may be determined from derived mandibular features such as displacement of the mandible and/or head during sleep or changes in respiratory effort and/or central drive.

In an embodiment the mandibular activity data may also provide information on muscle fatigue of the subject, which may be determined from derived mandibular features such as displacement of the mandible and/or head during sleep or changes in respiratory effort and/or central drive.

In an embodiment the mandibular activity data may also provide information on snoring or sleep related noises and/or the general sleeping quality of the subject, which may be linked to mandibular features such as displacement of the mandible and/or head during sleep.

In an embodiment the sensing unit may be configured for recording of mandibular movement and a processing unit operatively connected to said sensing unit; wherein the processing unit is configured to receive, from said sensing unit, mandibular activity data; and, determine, from the mandibular activity data one or more respiratory features which are indicative of respiratory activity of the subject and/or one or more sleeping features which are indicative of a sleeping activity of the subject. The inventors have determined that mandibular data may be linked to respiratory and/or sleeping parameters, for example directly through by threshold-based detection of specific derived mandibular activity features or indirectly by pattern recognition of mandibular activity data. Exemplary embodiments of such configurations may be found discussed further below.

The sensor may comprise at least one gyroscope configured for recording rotational movements of the subject's mandible. The recorded rotational movements data may be linked to various mandible movement classes comprising a set of rotational values, which may be indicative of at least one rate, rate change, frequency, and/or amplitude of mandibular rotations associated with the mandible movement class. The recorded rotational movements may be analysed to determine mandibular activity data, respiratory activity data and/or sleeping activity data as described above. Advantageously, the gyroscope is provided on the left and/or right electrode such that it can be placed together with the electrodes and reduce the complexity of the device.

The provision of a gyroscope in the sensing device was found to be particularly well suited for recording of mandibular movement in comparison to other sensing devices typically applied in the art, such as accelerometers, force/pressure sensors, or magnetic sensors. For instance, an accelerometer can only allow for measurement of linear acceleration and is thus unsuitable for measurement of rotational mandibular displacements. Moreover, the accelerometer can be affected by movement of the body or the head, such as the chest or trachea during breathing, and distinguishing between the origin of data is difficult and adds unnecessary noise and complexity to the system. This has a negative impact on a diagnosis that is based on the measured data streams. The inventors have found that the rotation of the mandible as recorded by a gyroscope carries the necessary information to arrive at an accurate assessment of mandibular activity data, respiratory activity data and/or sleeping activity data as described above.

In a preferred embodiment the sensing device may comprise at least one gyroscope, at least one accelerometer and optionally also at least one magnetometer. The inventors have found that accelerometers are particularly well-suited for measuring movements and positions of the head. The addition of an accelerometer to the present system may allow to discern head movement from jaw movement and thereby more accurately assess the behaviour of the mandible during sleep. Further, the provision of a magnetometer may allow assessing the orientation of the sensing unit like a compass to determine the direction of the movements recorded by the gyroscope and/or accelerometer. Accordingly, the preferred embodiment may be particularly well suited for recording of mandibular movement.

In some embodiments the sensor may also comprise devices selected from the list including an oxygen sensor (e.g. oximeter), a temperature sensor (e.g. thermometer), a sound sensor (e.g. microphone), a muscle activity sensor (e.g. electromyography unit), a brain activity sensor, a heart activity sensor, a blood sensor (e.g. pulse photoplethysmography). The provision of additional sensing devices may allow for the sensor to be customised to patient specific purposes, such as the detection of snoring.

Additionally, the wearable device as described herein may also be used in combination with other systems or methods. These systems may be therapeutic in nature, such as a breathing apparatus (CPAP, BiPAP, Adaptive Support Ventilation), a device for stimulating specific nerves and/or other muscles, whether transcutaneous or implanted, a device for correcting the posture and/or position of the body and/or head during sleeping. In some embodiments an alarm can be coupled to the system, and/or the system may be connected to or provided with a device having an alarm function.

The wearable devices of the present disclosure may comprise a processing unit, also referred to as data analysis unit, configured to receive, from said sensing unit, mandibular activity data; and, determine, from the mandibular activity data, one or more mandibular features, such as a position, rotation or displacement of the subject's mandible and/or one or more head features, such as a position, rotation or displacement of the subject's head.

In an embodiment the wearable device may comprise a sensing unit configured for recording of respiratory activity of the subject and a processing unit operatively connected to said sensing unit; wherein the processing unit is configured to receive, from said sensing unit, respiratory activity data; and, determine, from the respiratory activity data, one or more respiratory features, such as the frequency or intensity of the breathing, the occurrence of sleep disturbed breathing marked with increased respiratory effort and/or the occurrence of a respiratory disturbance, such as airway obstruction or collapse.

In some embodiments the respiratory activity data may also provide the device with feedback on the efficacy of the stimulation but may also trigger the device to initiate specific programmes to treat respiratory disturbances. In a particular embodiment the respiratory activity data may also provide information on snoring of the subject, which may be linked to respiratory features such as an increase in respiratory effort during sleep.

The wearable device may comprise a sensing unit configured for recording of sleeping activity of the subject and a processing unit operatively connected to said sensing unit; wherein the processing unit is configured to receive, from said sensing unit, sleeping activity data; and, determine, from the sleeping activity data, one or more sleeping features, such as sleeping state detection, determination of specific sleeping stages and/or assess the sleep quality. The sleep activity data may provide the device with feedback on the efficacy of the stimulation but may also trigger the device to target specific sleeping states or stages. The sleep quality parameters may include, e.g., total sleep time (TST), sleep onset latency (SOL), wake time after sleep onset (WASO), awakening or arousal index, sleep efficiency (SE), ratios of REM, non-REM sleep, REM sleep latency, and other sleep quality metrics.

The data analysis unit may be configured to derive a plurality of values from one or more sensing data as described above, such as the mandibular activity data, respiratory activity data and/or sleeping activity data, and for matching the derived values with predefined classes. Preferably, the sensing data is sampled with a specific sampling rate, which may for example range from 1.0 to 100.0 Hz, or from 2.0 to 50.0 Hz, or from 5.0 to 25.0 Hz, preferably 10.0 Hz. The values from the sampled or unsampled sensing data may comprise one or more of the following mathematical procedures: discretization, time-averaging, normalisation, (fast) Fourier transformation, and the like. Those skilled in the art may appreciate the numerous modifications and variations thereon.

The matching may be fully or partially automated by the provision of a machine learning model, such that the data analysis unit is configured to learn a number of statistical and/or physical metrics in order to capture the characteristics of the signal in frequency and time domains and identify patterns of rotation signal to specific events, such as sleep stages, respiratory effort, muscle fatigue, and the like. In an embodiment the machine learning model may be selected from the list of extreme gradient boosting, deep neural network, convolutional neural network, random forest. The inventors found that these models are particularly suited for classifying the recorded mandibular activity data, respiratory activity data and/or sleeping activity data into the corresponding classes. However, those skilled in the art may appreciate the numerous modifications and variations thereon. The provision of a machine learning model may thus provide for automatic interpretation of the relevant information and/or matching characteristic data with sleep disorder events.

In an embodiment the data analysis unit, preferably by means of recorded mandibular activity data, may be configured to determine efficacy of the stimulation without requiring subject feedback, specifically during subject sleep. High efficacy of the stimulation can be determined when irregular movement of the mandible decreases over time, preferably synchronises with the selected stimulation parameters of the applied electrical stimulation. On the other hand, a high occurrence of irregular mandibular movement may indicate that the muscles of the subject are not sufficiently responding to the applied electrical stimulation and as such one or more stimulation parameters may need to be adjusted, for example by increasing the current intensity.

In an embodiment the sensing unit, preferably by means of recorded mandibular activity data, may be configured to determine muscle fatigue without requiring subject feedback, specifically during subject sleep. Muscle fatigue can be determined when the elevation of the mandible decreases overtime, yet the stimulation parameters remained unchanged across a specific period of time or sleeping stage.

In an embodiment, muscle fatigue can be more accurately determined by tracking the displacement of the mandible, preferably by means of an accelerometer, and/or by tracking the central drive and/or respiratory effort, preferably by means of a gyroscope. An embodiment of a sensing unit comprising an accelerometer and gyroscope, preferably mounted on the same position, is therefore contemplated.

In an embodiment, the following parameters may allow for determining types of muscle fatigue:

Absence of muscle fatigue may be determined when distinct mouth closing can be observed (typically in the form of distinct mandible displacement in recorded accelerometer data) and/or the central drive/respiratory effort is decreasing (typically derived from the peak-to-peak amplitude of recorded gyroscope data).

Peripheric muscular and/or fibre fatigue may be determined when distinct mouth closing cannot be observed (typically reduced mandible displacement in the recorded accelerometer data) and/or the central drive/respiratory effort is increasing (typically indicated by increased peak-to-peak amplitude of the recorded gyroscope data).

Spinal or supraspinal fatigue may be determined when distinct mouth closing cannot be observed (typically reduced mandible displacement in the recorded accelerometer data) and/or the central drive/respiratory effort is decreasing (typically indicated by decreased peak-to-peak amplitude of the recorded gyroscope data).

Analysis of the recorded data may be used to provide a feedback loop for the wearable device to improve control of the subject's mandible by adjusting one or more stimulation parameters and advantageously improve the device efficacy. In an embodiment the wearable device may comprise a processing unit which is operatively connected to the stimulator and configured to determine from the sensing data a stimulation response and compare said stimulation response with a desired response. Further, the processing unit may be configured to adjust at least one electrical stimulation parameter if a difference between the stimulation response and desired response is determined to effectuate the desired response or alternatively determine an adjustment to least one electrical stimulation parameter to effectuate the desired response and provide the stimulator with said adjustment as instructions. In an embodiment the stimulation intensity may be adjusted. Nonetheless, the pulse frequency, the pulse width and/or the stimulation duration may also be adjusted. Exemplary embodiments of respiratory feedback loops may be found discussed below.

In an embodiment the processing unit may be configured to determine from mandibular activity data the mandibular response to the stimulation and compare said mandibular stimulation response with a desired response, the desired response consisting of an elevation of the subject's mandible to open the upper airway. In an embodiment the processing unit may be configured to determine from respiratory activity data the stimulation response and compare said respiratory stimulation response with a desired response, the desired response consisting of a decrease in the respiratory effort of a sleeping subject. In an embodiment the processing unit may be configured to determine from sleeping activity data the sleeping response to the stimulation and compare said sleeping stimulation response with a desired response, the desired response consisting of an improvement in the sleeping quality of a sleeping subject. Additionally, the device may be configured for determination of other responses, such as reduction in snoring.

Analysis of mandibular activity data may be used to track muscle fatigue. The wearable device may be provided with a muscle fatigue detection module which is configured to determine muscle fatigue in the subject's mandibular activity data and preferably adjust one or more stimulation parameters of the electrical stimulation. There are different stimulation parameters that can be adjusted, individually or in combination, to adjust neuromuscular electrical stimulation for optimized benefits, specifically improve closure of the mouth and/or reduce or prevent muscle fatigue. These parameters may include the current intensity, the pulse width and frequency, the duty cycle, stimulation of different target muscles, sequential periods of stimulation as a function of the target, target of specific period of time or a sleeping stage, amplitude of the monitored accelerometer and drive responses. For example, if muscle fatigue is detected, it is possible to reduce the current intensity, preferably by 10%, 20%, 30%, 40%, 50% or more, and/or modify the duty cycle, specifically by increasing the rest period of the duty cycle, preferably by 10%, 20%, 30%, 40%, 50% or more; for example from 5 sec to 10 sec. Alternatively, upon detection of muscle fatigue the detection module may temporarily interrupt the electrical stimulation to allow the muscles to recover, for example by providing a break for 1 min or 2 min. Once the stimulation is restarted the muscle fatigue detection module may determine if the stimulation response has improved and if there is insufficient improvement provide another, preferably longer break.

In an embodiment the muscle fatigue detection module may be configured to change one or more stimulation programs when a specific sleeping stage is detected, specifically the recruitment program, the rehabilitation program and/or the retraining program. The session may be typically initiated with the recruitment program and/or the rehabilitation program. However, since these programs may fatigue the muscles (due to relatively narrow pulses and/or higher current intensity), the muscle fatigue module may be configured to switch the stimulator to the retraining program (with relatively wider pulses and/or lower current intensity) in order to reduce the muscle fatigue, for example when central fatigue is detected.

In an embodiment the muscle fatigue detection module may be configured to determine the type of muscle fatigue, specifically peripheric muscular and/or fibre fatigue, and/or spinal or supraspinal fatigue. The methodology of muscle fatigue detection is discussed earlier in the present disclosure. In an embodiment the muscle fatigue detection module, when detecting peripheric muscular and/or fibre fatigue, may reduce the current intensity and/or increase the pulse width of the simulation, preferably by activating a program defined by a lower current intensity and/or wider pulses than the present program. In an embodiment the muscle fatigue detection module, when detecting spinal or supraspinal fatigue, may increase the frequency and/or increase the pulse width of the simulation, preferably by activating a program defined by a higher frequency and/or wider pulses than the present program.

In a particular embodiment, the processing unit may be configured to detect poor muscle contraction and adjust the session to commence with the rehabilitation program. To clarify, in the presence of a mild disease with no severe episodes of apnea or hypopnea, there is time to rehabilitate the target muscles. Accordingly, instead of adjusting one or more stimulation parameters to increase the efficiency of the electrical stimulation (e.g. by increasing current intensity and/or frequency), it may be preferably to decrease the electrical stimulate such that the muscle fibre strength can built up to take the stronger stimulation. This may alleviate discomfort for subjects at risk of muscular fatigue or highly sensitive to higher current intensities to discontinue the session. Advantageously, this functionality may be included in the wearable device to be activated on demand, for example when a clinical physician diagnoses poor masseter contraction or some underling disease. Also, the rehabilitation program can be proposed to subject sensitive to current intensities above 2 mA, specifically when the stimulation prevents the subject from falling asleep and/or wakes up the subject after a ramp period.

The wearable device may be provided with a respiratory effort detection module which is configured to determine the level of respiratory effort in the subject's respiratory data. In an embodiment the respiratory effort detection module may be configured to detect an increased respiratory effort in the subject's respiratory data and adjust one or more stimulation parameters and/or stimulation programs to reduce respiratory effort. Stimulation can be adjusted based on recorded respiratory effort/central drive; preferably by increasing the efficiency of the stimulation when an increase in respiratory effort/central drive is detected, and/or by decreasing the efficiency of the stimulation when a decrease in respiratory effort/central drive is detected.

In an embodiment the respiratory disturbance detection module may be configured to detect a higher frequency and/or higher amplitude (peak-to-peak amplitude) indicative of increased respiratory effort, preferably compared to a baseline value, and adjust one or more stimulation parameters to promote stimulation; preferably by maintaining the same frequency and pulse width but increasing the current intensity; more preferably by increasing the current intensity by 10%, 20%, 30%, 40%, 50% or more, and/or decrease the rest period of the duty cycle by 10%, 20%, 30%, 40%, 50% or more. This may improve the stimulation's efficiency and/or reduce respiratory effort/central drive. The baseline value may be a standard value, for example based on an expected population average, but preferably is a personalised value based on the subject's respiratory profile. Advantageously the baseline value starts off as a standard value during the start of a session and is adapted based on recorded data.

In an embodiment the respiratory disturbance detection module may be configured to detect a lower frequency and/or lower amplitude (peak-to-peak amplitude) indicative of decreased respiratory effort, preferably compared to a baseline value and adjust one or more stimulation parameters to reduce stimulation; preferably by maintaining the same frequency and pulse width but decreasing the current intensity; more preferably by decreasing the current intensity by 10%, 20%, 30%, 40%, 50% or more, and/or increasing the rest period of the duty cycle by 10%, 20%, 30%, 40%, 50% or more. This may improve the subject's comfort and/or reduce the chance for muscle fatigue.

Analysis of respiratory activity data may be used to selectively focus a specific respiratory disturbance, such as airway obstruction or collapse. The wearable device may be provided with a respiratory disturbance detection module which is configured to determine the presence of a respiratory disturbance in the subject's respiratory data such that the electrical stimulation can be initiated or adjusted when a respiratory disturbance is detected. Stimulation can be adjusted based on the detection of a respiratory disturbance, such as airway obstruction or collapse; preferably by increasing the efficiency of the stimulation when an increased amplitude, frequency and/or duration of one or more respiratory disturbances is detected, and/or decreasing the efficiency of the stimulation when a decreased amplitude, frequency and/or duration of one or more respiratory disturbances is detected.

In an embodiment the respiratory disturbance detection module may be configured to detect a higher frequency, higher amplitude (peak-to-peak amplitude) and/or increased duration of respiratory disturbances compared to a baseline value and adjust one or more stimulation parameters to promote stimulation; preferably by maintaining the same frequency and pulse width but increasing the current intensity; more preferably by increasing the current intensity by 10%, 20%, 30%, 40%, 50% or more, and/or decrease the rest period of the duty cycle by 10%, 20%, 30%, 40%, 50% or more. This may improve the stimulation's efficiency and/or reduce, preferably prevent, the occurrence of further respiratory disturbances. The baseline value may be a standard value, for example based on an expected population average, but preferably is a personalised value based on the subject's respiratory profile. Advantageously the baseline value starts off as a standard value during the start of a session and is adapted based on recorded data.

In an embodiment the respiratory disturbance detection module may be configured to detect a lower frequency, lower severity and/or decreased duration of respiratory disturbances compared to a baseline value and adjust one or more stimulation parameters to reduce stimulation; preferably by maintaining the same frequency and pulse width but decreasing the current intensity; more preferably by decreasing the current intensity by 10%, 20%, 30%, 40%, 50% or more, and/or increasing the rest period of the duty cycle by 10%, 20%, 30%, 40%, 50% or more. This may improve the subject's comfort and/or reduce the chance for muscle fatigue.

Analysis of respiratory activity data may be used to selectively focus snoring and/or sleep related noises. The wearable device may be provided with a snoring detection module which is configured to determine the occurrence of snoring/sleep related noises such that the electrical stimulation can be initiated or adjusted when snoring/sleep related noises is detected. The snoring detection may optionally be threshold based, for example when exceeding a specific volume. Stimulation can be adjusted based on recorded snoring or sleep related noises; preferably by increasing the efficiency of the stimulation when an increase in snoring/sleep related noises is detected, and/or by decreasing the efficiency of the stimulation when a decrease in snoring/sleep related noises is detected; preferably by maintaining the same frequency and pulse width but increasing the current intensity; more preferably by increasing the current intensity by 10%, 20%, 30%, 40%, 50% or more, and/or decrease the rest period of the duty cycle by 10%, 20%, 30%, 40%, 50% or more. This may improve the stimulation's efficiency and/or reduce, preferably prevent, the occurrence of further snoring/sleep related noises.

The wearable device may be provided with a sleeping stage determination module which is configured to determine an awake and asleep state of the subject such that the electrical stimulation can be initiated when the subject falls asleep and terminated as the patient wakes up. The electrical stimulation may be perceived as distractive for falling asleep by certain subjects. The detection of at least an awake and asleep phase allows the subject to fall asleep more easily before the stimulation is initiated. Also, the electrical stimulation may be gradually initiated to avoid from awakening the subject due to activation of the device, for example by gradually increasing the stimulation intensity.

The wearable device may be provided with a sleeping stage determination module which is configured to determine one or more sleep stages of the subject such that the electrical stimulation can be initiated, adjusted and/or terminated when the subject enters a specific sleeping stage. Accurate sleeping state detection may improve the stimulation response and hence the efficiency of the sessions for therapeutic or non-therapeutic purposes. Further, accurate sleeping stage detection may increase the safety and comfort of the session, specifically by reducing or preventing stimulation during deep sleep (e.g. N3) and/or during awake states or awakenings. This allows the device to focus a specific sleeping stage of the subject for stimulation such that the subject can still fall easily asleep or does not wake during the deeper stages. Further still, accurate sleeping state detection may reduce or prevent the occurrence of muscle fatigue, specifically by reducing or preventing stimulation during specific deep sleep (e.g. N3) and/or providing a variable stimulation during lighter sleep, for example by progressively increasing/decreasing the current intensity.

The sleep detection module may be configured to detect a specific sleep stage according to the following classification (sorted by increasing level of computational complexity):

2 Class (i.e. binary) scoring for detecting the awake or sleeping state in a subject;

3 Class scoring for classifying the sleeping stage, including the awake state, the light sleeping (N1 and N2) stage and/or the non-light sleeping (N1 and N2) stage in a subject;

3 Class scoring for classifying the sleeping stage, including the awake state, the deep sleeping (N3) stage and/or the non-deep sleeping (N3) stage in a subject;

3 Class scoring for classifying the sleeping stage, including the awake state, the REM sleeping stage and/or the non-REM sleeping stage in a subject;

4 Class scoring for classifying the sleeping stage, including the awake state, the light sleeping (N1 and N2) stage, the deep sleeping (N3) stage and/or the REM sleeping stage in a subject;

5 Class scoring for classifying all sleeping stages, including the awake state, the N1 sleeping stage, the N2 sleeping stage, the N3 sleeping stage and/or the REM sleeping stage in a subject.

The skilled person may appreciate that, depending on the required data processing complexity, the data analysis may be performed by the processing unit provided on the wearable device or, if more complex calculation is required, the calculation may be performed on an external device that is connected to the wearable device, such as the subject's smartphone or a server. Nonetheless, for the sake of convenience in the present disclosure it will be assumed that all necessary calculations can be performed by the sleeping stage determination module as disclosed herein.

In an embodiment the sleeping stage determination module may be configured to determine the occurrence of a light sleeping (N1 and/or N2) stage and/or REM stage and initiate or adjust the applied electrical stimulation when the subject enters said light sleeping (N1 and/or N2) stage and/or REM stage. It was discovered that during the light sleeping (N1 and/or N2) stage, the muscles are more sensitivity for retraining purposes and as such may benefit for an adjustment to one or more stimulations parameters, such as an increased stimulation intensity. The light sleeping (N1 and/or N2) stage and/or REM stage may be associated with a specific mandibular condyle rotation and may therefore be determined from mandibular activity data. Moreover, during light sleeping (N1 and/or N2) stage and during REM sleep stage, the risk of apnea/hypopneas increases (in comparison to the deep N3 sleep stage), essentially because the compensatory drive directed to the pharyngeal musculature is reduced or highly variable and thus less efficient (REM sleep).

The N3 sleeping stage is typically characterized by stable mandibular movements. Accordingly, in an embodiment the sleeping stage determination module may be configured to determine N3 based on a stable peak-to-peak amplitude and/or breathing frequency. After detection of the N3 sleeping stage the sleeping stage determination module may be configured to switch to the rehabilitation program; preferably by maintaining the same frequency and pulse width but decreasing the current intensity; more preferably by decreasing the current intensity by 10%, 20%, 30%, 40%, 50% or more, and/or increasing the rest period of the duty cycle by 10%, 20%, 30%, 40%, 50% or more. Alternatively, after detection of the N3 sleeping stage the sleeping stage determination module may be configured to switch to the retraining program; preferably by increasing the frequency and pulse width and optionally decreasing the current intensity; preferably by increasing the frequency by 10%, 20%, 30%, 40%, 50% or more, increasing the pulse width by 10%, 20%, 30%, 40%, 50% or more, increasing the rest period of the duty cycle by 10%, 20%, 30%, 40%, 50% or more and/or decreasing the current intensity by 10%, 20%, 30%, 40%, 50% or more.

The REM sleeping stage is typically characterized by unstable mandibular movements. Accordingly, in an embodiment the sleeping stage determination module may be configured to determine REM based on an unstable peak-to-peak amplitude and/or breathing frequency. After detection of the REM sleeping stage the sleeping stage determination module may be configured to switch to the recruitment program; preferably by maintaining the same frequency and pulse width but increasing the current intensity; more preferably by increasing the current intensity by 10%, 20%, 30%, 40%, 50% or more, and/or decrease the rest period of the duty cycle by 10%, 20%, 30%, 40%, 50% or more. Alternatively, if the stimulator is already operating in the recruitment program, one or more parameters of said recruitment program may be adjusted to increase stimulation; preferably by increase the current intensity by 10%, 20%, 30%, 40%, 50% or more, and/or decrease the rest period of the duty cycle by 10%, 20%, 30%, 40%, 50% or more. In an embodiment the sleeping stage determination module may be configured to slowly ramp up during the during the N1 sleep stage in anticipation of the following sleep stages to prevent the occurrence of inappropriate arousals. In adults, the typical N1 sleeping stage is a relatively short and light; the sleep stage may be expected to deepen in a few minutes. Accordingly, the sleeping stage determination module may be configured according to a ramping algorithm that detects an amount of predefined amount of continuous sleep, preferably by means of the sleeping stage sensor as disclosed herein. Once a specific sleep stage has been detected, the ramping algorithm may adjust one or more stimulation parameters over a specific time length, for example by linearly increasing the current intensity from 0% to 100% over 20 minutes.

In an embodiment the sleeping stage determination module may be configured to determine the occurrence of a deep sleeping (N3) stage and terminate the applied electrical stimulation when the subject enters said deep sleeping (N3) stage. It was discovered that during the deep sleeping (N3) stage, the risk of incident and severe SDB decreases because the central motor control of the ventilation is stabilised at the lever of the upper airway muscles (stability of the chemo and baro drive) and the upper airway patency (through the premotor neurons of the V, XII and VII cranial nerves) is optimized by the neurons regulating breathing. Accordingly, the electrical stimulation can be reduced or alternatively terminated the during the deep sleeping (N3) stage, which may allow the stimulated muscles to relax in order to prevent muscle fatigue. The deep sleeping (N3) stage may also be associated with a specific mandibular condyle rotation and may therefore be determined from mandibular activity data.

In an embodiment the sleeping state or stage of the subject may be determined by the following programme:

dividing the sensing data into epochs of a specific time, for example 30 seconds, wherein the sensing data is preferably selected from mandibular activity data, respiratory activity data and/or sleep activity data, and applying a mathematical model to assign a sleeping state to each epoch;

wherein said mathematical model comprises the step of extracting at least one feature from the recorded sensing data for each epoch;

tracking the value of said extracted feature across every epoch;

setting a feature specific threshold value; and, adjusting the sleeping state of an epoch if the extracted feature value exceeds the feature specific threshold value.

Typical features extracted by the sleep detection model from the recorded sensing data may include the maximum and minimum values (e.g. mandibular activity data recorded by a gyroscope), the mean, the median, the standard deviation. Preferably the sleep detection model extracts a plurality of features to improve the sensitivity and reliability of the sleep detection module. The inventors found that the mandibular activity recorded by a gyroscope may provide for a particularly reliable awake state detection. In particular, the following feature specific threshold values were identified. The awake state may be determined when the standard deviation of the gyroscope norm exceeds threshold of at least 1.10 to at most 1.50, preferably 1.15 to 1.25, more preferably around 1.20, such as 1.17. The awake state may be determined when the maximum value of the gyroscope norm exceeds threshold of at least 14.0 to at most 15.0, preferably 14.1 to 14.9, or 14.2 to 14.8, more preferably 14.3 to 14.5, or 14.3 to 14.4.

The sleep respiratory disturbances related metrics may include the hourly occurring rate and cumulated duration of respiratory efforts during sleep. The analysis unit may be configured for reporting the interpreted subject specific parameters. The reporting may include providing an output to a device, such as a computer or smartphone. The reporting may also include providing a visual or textual report of the subject specific parameters, for example in the form of a hypnogram.

In an embodiment the sleep detection module may be configured to change one or more stimulation programs when a specific sleeping stage is detected, specifically the recruitment program, the rehabilitation program and/or the retraining program. The session may be typically initiated with the recruitment program and/or the rehabilitation program which will be applied during the initial sleeping stages (e.g. N1, N2). However, during deeper sleeping stages, specifically N3, the ventilation and the muscular pharyngeal walls (dedicated for the airway patency) are typically more stable and hence require less electrical stimulation to produce a beneficial response. Accordingly, the sleep detection module may be configured to switch the stimulator to the retraining program in order to prevent possible muscle fatigue and/or conserving battery of the wearable device.

Figure 4:
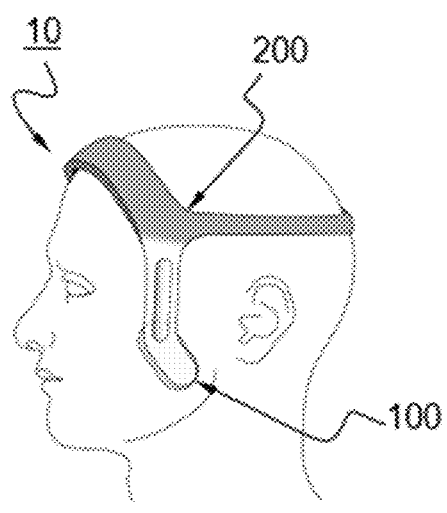
FIG. 4 is a perspective view of the wearable device (10) configured for stimulation of masseter muscles according to another preferred embodiment of the present invention.

The wearable device may comprise a garment, specifically a wearable garment, configured for holding at least part of the stimulator and/or supporting the electrode. In an embodiment the wearable device may comprise a collar, wherein said collar is configured for placement around at least a portion of the subject's neck. In one embodiment the collar may be rigid such that it can be placed onto the subject's shoulders. An example of such an embodiment is shown in FIG. 2. In another embodiment the collar may be flexible such that it can snap around the subject's neck, advantageously providing a compressive force on the subject's neck such that the collar is held in place around the neck during sleep. An example of such an embodiment is shown in FIG. 4. In an embodiment the wearable device may comprise a headband, wherein said headband is configured for placement around at least a portion of the subject's head. The headband may similarly be rigid, flexible or a combination of both. An example of such an embodiment is shown in FIG. 5.

The garment may have a rigid body which is curved so that it can be fit around the subject's body part, preferably the neck or head. Advantageously, the garment has a semi-circular or arched shape, which may improve the ergonomics of the design and prevent it from falling off during sleep. The garment may be provided with a gap to allow for easier fitting around the neck.

Preferably, the garment body may be sufficiently stiff to protect the electronics within, but flexible enough to ensure compliance with the movements of the subject. In an embodiment the garment has a rigid polymer core covered by a silicon shell. Silicon is particularly well-suited material to ensure pleasant skin contact. The components may for example be 3D-printed or moulded for larger production. The inside section of the garment may be provided with a texture adapted to improve the comfort for contact with the subject skin but also provide sufficient surface friction to prevent displacement of the garment, due to rotation of the body during sleep. In an embodiment the garment is covered with a textile such as polyester or a polyamide to allow the material to breathe since it may be in skin contact for extended time periods.

In an embodiment, the garment may be configured to (lightly) press onto the subject's body part, specifically the neck and/or head, to create a compressive force. This has the advantage that the garment can be more easily fixed in placed, for example during sleeping movements. Furthermore, the compressive force can be extended to the electrodes such that the electrodes press onto the target stimulation zone. Compression of the electrode may improve skin contact, decrease skin resistance, and/or enable stimulation closer to the motor nerve. As a result, this may increase the stimulation response and/or decrease regional side effects or discomfort.

The electrodes may be electrically connected to the garment with connective cables. In an embodiment the wearable device may be provided with a flexible cable the length of which may be adjusted for easier placement of the electrode onto the subject's skin and/or respond to movements of the subject, such as rotation of the head or body. The length adjustment of the flexible cable may prevent the electrode from dismounting from the subject skin. The garment may be provided with a cable housing adapted for tensioning the cable and/or retracting excess cable, for instance by rolling it up into said housing. Optionally, a locking mechanism may be provided on the garment to secure the cable at different lengths. Alternatively, the cable may be rigid, but this could reduce sleep quality. The cable may be provided with electrical cables to allow current to travel from the stimulator disposed in the garment to the electrodes. An example of such an embodiment is shown in FIG. 2. The electrodes may detachably attach to the cables to allow replacement of used or defective electrodes. In another embodiment the cables may be integrated into a housing, which may be part of the garment. An example of such an embodiment is shown in FIG. 5.

The garment may also be provided with a battery pack and optional plug to allow for electrical charging of said battery when the device is not in use, typically during daytime. Optionally, the garment may be provided with user interface buttons, such as a power button. Additionally, a display may be provided that informs the subject about one or more actions, such as selected programs, information about battery life or charging time, and so on.

The wearable device may be configured for connecting to an output device, such as a smartphone, and transmitting data to said output device. The output device may be provided with analytical software, such as an application, which is configured to analyse the received data and optionally determine various features from said data. The wearable device may comprise a storage means for storing stimulation data, such as an overview of the stimulation parameters generated by the stimulator, which stored data may be exported to said output device for analysis. In an embodiment wherein the wearable device is provided with a sensor, it may comprise a storage means for storing sensing data which may similarly be exported to said output device for analysis.

The output device may be configured to determine a subject specific profile which may be used to, for example, adjust one or more one pulse specific parameters of the pulsed electrical current or adjust one or more one feature specific threshold value of the sleep detection module. Also, the subject specific profile may be used to provide user feedback to promote the sleep quality improvements in the form of, for example, games or questionnaires investigating neurocognitive, quality of life, mood, and others biological/physiological measures.

Additionally, the output device may be configured to transmit the received data to a dedicated data analysis device, such as an external server, which is configured to determine from said received data more complicated features, for example, by means of machine learning model.

An aspect of the present disclosure relates to a method for decreasing the respiratory effort of a subject during sleep, the method comprising:

selecting a portion of the subject's skin ranging from a left, preferably masseter, pterygoid and/or temporalis, muscle motor point to the left posterior angle of the mandible and positioning a left electrode on the selected skin portion, and selecting a portion of the subject's skin ranging from a right, preferably masseter, pterygoid and/or temporalis, muscle motor point to a right posterior angle of the mandible and positioning a right electrode on the selected skin portion;

applying a transcutaneous electrical stimulation from the left electrode to at least one left, preferably masseter, pterygoid and/or temporalis, muscle and from the right electrode to at least one right, preferably masseter, pterygoid and/or temporalis, muscle;

wherein the applied electrical stimulation promotes the contraction of said left and right stimulated, preferably masseter, pterygoid and/or temporalis, muscles to controllably elevate the subject's mandible such that the upper airway is opened.

An aspect of the present disclosure relates to a method for decreasing the respiratory effort of a subject being provided with a sensor configured for detecting the movement of the subject's mandible during sleep, the method comprising:

outputting, by the sensor, a signal indicative of mandibular activity;

receiving, by a signal processing unit, said signal indicative of mandibular activity;

processing, by the signal processing unit, said signal indicative of mandibular activity to determine mandibular activity data;

actuating, by the signal processing unit, a stimulator by means of a control signal, the control signal being produced by the signal processing unit based on the determined mandibular activity data;

generating, by the stimulator, an electrical stimulation characterised by one more stimulation parameter suitable for promoting the contraction of a, preferably masseter, pterygoid and/or temporalis, muscle to controllably elevate the subject's mandible such that the upper airway can be opened.

An aspect of the present disclosure relates to a method for decreasing the respiratory effort of a subject being provided with a sensor configured for detecting the movement of the subject's mandible during sleep, the method comprising:

outputting, by the sensor, a signal indicative of mandibular activity;

receiving, by a signal processing unit, said signal indicative of mandibular activity;

processing, by the signal processing unit, said signal indicative of mandibular activity to determine respiratory activity data;

optionally, determining, by the signal processing unit, the occurrence of sleep disturbed breathing marked with increased respiratory effort;

optionally, determining, by the signal processing unit, the occurrence of a sleep respiratory disturbance;

actuating, by the signal processing unit, a stimulator by means of a control signal, the control signal being produced by the signal processing unit based on the determined respiratory activity data, optionally based on the determined sleep disturbed breathing and/or determined sleep respiratory disturbance;

generating, by the stimulator, an electrical stimulation characterised by one more stimulation parameter suitable for promoting the contraction of a, preferably masseter, pterygoid and/or temporalis, muscle to controllably elevate the subject's mandible such that the upper airway can be opened.

An aspect of the present disclosure relates to a method for decreasing the respiratory effort of a subject being provided with a sensor configured for detecting the movement of the subject's mandible during sleep, the method comprising:

outputting, by the sensor, a signal indicative of mandibular activity;

receiving, by a signal processing unit, said signal indicative of mandibular activity;

processing, by the signal processing unit, said signal indicative of mandibular activity to determine sleep activity data;

optionally, determining, by the signal processing unit, a sleeping state, said sleeping state including an awake state and an asleep state;

optionally, determining, by the signal processing unit, a sleeping stage, said sleeping stage including at least one stage selected from a light (N1) sleeping stage, a light (N2) sleeping stage, a deep (N3) sleeping stage N3 and/or REM sleeping;

actuating, by the signal processing unit, a stimulator by means of a control signal, the control signal being produced by the signal processing unit based on the determined sleep activity data, optionally based on a determined sleeping state and/or determined sleeping stage;

generating, by the stimulator, an electrical stimulation characterised by one more stimulation parameter suitable for promoting the contraction of a, preferably masseter, pterygoid and/or temporalis, muscle to controllably elevate the subject's mandible such that the upper airway can be opened.

In some preferred embodiments, the methods for decreasing the respiratory effort of a subject as described above may further comprise:

transmitting, by the stimulator, the generated electrical stimulation to a left electrode positioned a selected portion of the subject's skin ranging from a left, preferably masseter, pterygoid and/or temporalis, muscle motor point to the left posterior angle of the mandible;

transmitting, by the stimulator, the generated electrical stimulation to a right electrode positioned on a selected portion of the subject's skin ranging from a right, preferably masseter, pterygoid and/or temporalis, muscle motor point to the right posterior angle of the mandible;

applying, by the left electrode, a transcutaneous electrical stimulation to at least one left, preferably masseter, pterygoid and/or temporalis, muscle to promote contraction of said left, preferably masseter, pterygoid and/or temporalis, muscle, and applying, by the right electrode, a transcutaneous electrical stimulation to at least one right, preferably masseter, pterygoid and/or temporalis, muscle to promote contraction of said right, preferably masseter, pterygoid and/or temporalis, muscle; wherein the left and right stimulated, preferably masseter, pterygoid and/or temporalis, muscles controllably elevate the subject's mandible such that the upper airway is opened.

An aspect of the present disclosure relates to a method for decreasing the respiratory effort of a subject during said subject's sleep, the method comprising:

selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;

selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;

applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased; wherein said electrical stimulation is generated according to a duty cycle that has a stimulation period of 1 sec to 20 sec and/or a rest period of 1 sec to 20 sec.

An aspect of the present disclosure relates to a method for decreasing the respiratory effort of a subject during said subject's sleep, the method comprising:

selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;

selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;

applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased; wherein said electrical stimulation is generated according to a duty cycle that has a stimulation period of 1 sec to 20 sec and/or a rest period of 1 sec to 20 sec.

An aspect of the present disclosure relates to a method for recruiting of a target muscle to decrease the respiratory effort of a subject during said subject's sleep, the method comprising:

selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;

selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;

applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased;

wherein said electrical stimulation is generated according to the following stimulation parameters: a current intensity between 5 mA to 10 mA, preferably 6 mA to 10 mA; a frequency between 15 Hz to 50 Hz, preferably 25 Hz to 45 Hz, more preferably 30 Hz to 40 Hz; a pulse width between 50 µs to 300 µs, preferably 225 µs to 275 µs, more preferably 200 µs to 250 µs; and, a duty cycle with a stimulation period of 1 sec to 20 sec and/or a rest period of 1 sec to 20 sec.

An aspect of the present disclosure relates to a method for rehabilitating the muscle function of a target muscle to decrease the respiratory effort of a subject during said subject's sleep, the method comprising:

selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is mounted on the left target muscle's motor point and a second electrically conductive element is mounted along the direction of the left target muscle fibre;

selecting a portion of the subject's skin corresponding with the position of at least one right target muscle including a right masseter, a right pterygoid and/or a right temporalis muscle, and mounting at least one left bipolar electrode comprising at least two electrically conductive elements on said selected skin portion, wherein a first electrically conductive element is mounted on the right target muscle's motor point and a second electrically conductive element is mounted along the direction of the right target muscle fibre;

applying a biphasic transcutaneous electrical stimulation between the two electrically conductive elements of the left and right bipolar electrodes, which electrical stimulation promotes the contraction of the target muscles to controllably elevate the subject's mandible so that the respiratory effort can be decreased;

wherein said electrical stimulation is generated according to the following stimulation parameters: a current intensity between 1 mA to 4 mA, preferably 2 mA to 4 mA; a frequency between 15 Hz to 50 Hz, preferably 20 Hz to 45 Hz, more preferably 30 Hz to 40 Hz; a pulse width between 50 µs to 300 µs, preferably 225 µs to 275 µs, more preferably 200 µs to 250 µs; and, a duty cycle with a stimulation period of 1 sec to 20 sec and/or a rest period of 1 sec to 20 sec.

An aspect of the present disclosure relates to a method for retraining of a neuromuscular related circuit to decrease the respiratory effort of a subject during said subject's sleep, the method comprising:

selecting a portion of the subject's skin corresponding with the position of at least one left target muscle including a left masseter, a left pterygoid and/or a left temporalis muscle, and mounting at least one left bipolar electrode comprising at least two electrically conductive elements on said selected skin portion, wherein a first electrically conductive element is
mounted on the left target muscle's motor point and a
second electrically conductive element is mounted
along the direction of the left target muscle fibre;
selecting a portion of the subject's skin corresponding
with the position of at least one right target muscle
including a right masseter, a right pterygoid and/or a
right temporalis muscle, and mounting at least one left
bipolar electrode comprising at least two electrically
conductive elements on said selected skin portion,
wherein a first electrically conductive element is
mounted on the right target muscle's motor point and a
second electrically conductive element is mounted
along the direction of the right target muscle fibre;
applying a biphasic transcutaneous electrical stimulation
between the two electrically conductive elements of the
left and right bipolar electrodes, which electrical stimu-
lation promotes the contraction of the target muscles to
controllably elevate the subject's mandible so that the
respiratory effort can be decreased; wherein said elec-
trical stimulation is generated according to the follow-
ing stimulation parameters: a current intensity between
1 mA to 4 mA, between 2 mA to 4 mA; a frequency
between 50 Hz to 150 Hz, preferably between 70 Hz to
130 Hz, even more preferably 90 Hz to 110 Hz; a pulse
width between 500 μs to 1000 μs, preferably between
600 μs to 900 μs, more preferably 700 μs to 800 μs; and,
a duty cycle with a stimulation period of 1 sec to 20 sec
and/or a rest period of 1 sec to 20 sec.

An aspect of the present disclosure relates to treating the
snoring of a subject. The treating of snoring may be regarded
as a reduction in snoring intensity, for example half the
snoring intensity, or the altogether prevention of snoring, for
example a full reduction in snoring intensity. The prevention
of snoring may thus also be considered as a reduction in
snoring. In some preferred embodiments, the methods for
decreasing the respiratory effort of a subject as described
above may be a method for treating the snoring of a subject.
The inventors found that applying a transcutaneous electri-
cal stimulation to preferably the masseter, pterygoid and/or
temporalis muscles to controllably elevate t preferably the
he subject's mandible such that the upper airway is opened
may prevent the subject from snoring or at the very least
reduce the subject's snoring intensity.

In an embodiment the method for treating snoring may
comprise:
selecting a portion of the subject's skin ranging from a
left, preferably masseter, pterygoid and/or temporalis,
muscle motor point to a left posterior angle of the
mandible and positioning a left electrode on said
selected skin portion, and selecting a portion of the
subject's skin ranging from a right, preferably
masseter, pterygoid and/or temporalis, muscle motor
point to a right posterior angle of the mandible and
positioning a right electrode on said selected skin
portion;
applying a transcutaneous electrical stimulation from the
left electrode to at least one left, preferably masseter,
pterygoid and/or temporalis, muscle and from the right
electrode to at least one right, preferably masseter,
pterygoid and/or temporalis, muscle;

wherein the applied electrical stimulation promotes the
contraction of said left and right stimulated, preferably
masseter, pterygoid and/or temporalis, muscles to control-
lably elevate the subject's mandible such that the upper
airway is opened, and snoring is reduced and/or prevented.

The subject may be provided with a sensor configured for
detecting the snoring of the subject. The snoring signal may
be derived from mandibular activity data, as discussed
above, or by means of a dedicated snoring sensor, such as a
microphone provided on or near the subject.

In an embodiment the method for treating snoring may
comprise:
receiving, by a signal processing unit, said signal indica-
tive of snoring;
processing, by the signal processing unit, said signal
indicative of snoring;
actuating, by the signal processing unit, a stimulator by
means of a control signal, the control signal being
produced by the signal processing unit based on the
signal indicative of snoring;
generating, by the stimulator, an electrical stimulation
characterised by one more stimulation parameter suit-
able for promoting the contraction of a, preferably
masseter, pterygoid and/or temporalis, muscle to con-
trollably elevate the subject's mandible such that the
upper airway can be opened and snoring is reduced or
prevented.

An aspect of the present disclosure relates to a method for
treating snoring of a subject during said subject's sleep, the
method comprising:
selecting a portion of the subject's skin corresponding
with the position of at least one left target muscle
including a left masseter, a left pterygoid and/or a left
temporalis muscle, and mounting at least one left
bipolar electrode comprising at least two electrically
conductive elements on said selected skin portion,
wherein a first electrically conductive element is
mounted on the left target muscle's motor point and a
second electrically conductive element is mounted
along the direction of the left target muscle fibre;
selecting a portion of the subject's skin corresponding
with the position of at least one right target muscle
including a right masseter, a right pterygoid and/or a
right temporalis muscle, and mounting at least one left
bipolar electrode comprising at least two electrically
conductive elements on said selected skin portion,
wherein a first electrically conductive element is
mounted on the right target muscle's motor point and a
second electrically conductive element is mounted
along the direction of the right target muscle fibre;
applying a biphasic transcutaneous electrical stimulation
between the two electrically conductive elements of the
left and right bipolar electrodes, which electrical stimu-
lation promotes the contraction of the target muscles to
controllably elevate the subject's mandible so that the
snoring is reduced or prevented; wherein said electrical
stimulation is generated according to a duty cycle that
has a stimulation period of 1 sec to 20 sec and/or a rest
period of 1 sec to 20 sec.

An aspect of the present disclosure relates to a method for
assisting in the characterization of respiratory effort of a subject being provided with a sensor configured for detecting the movement of the subject's mandible during sleep, the method comprising the steps:

outputting, by the sensor, a signal indicative of mandibular activity;

receiving, by a data analysis unit, said signal indicative of mandibular activity;

storing, by means of a memory unit comprised in the data analysis unit, N mandibular activity classes, N being an integer larger than one; wherein at least one of the N mandibular activity classes is indicative of a sleep disturbed breathing;

wherein each $j^{th}$ ($1 \leq j \leq N$) mandible movement class consists of a $j^{th}$ set of rotational values, each $j^{th}$ set of rotational values being indicative of at least one rate of mandibular rotations;

associated with the $j^{th}$ class;

sampling, by means of a sampling element comprised in the data analysis unit, the mandibular activity data during a sampling period, thereby obtaining sampled mandibular activity data;

deriving, by means of the data analysis unit, a plurality of mandibular activity values from the sampled mandibular activity data; and, matching, by means of the data analysis unit, the mandibular activity values to the N mandibular activity classes of which at least one of the N mandibular activity class is indicative of a sleep disturbed breathing.

In some embodiments at least one of the N mandibular activity classes is indicative of a sleep disturbed breathing marked with increased respiratory effort.

In some embodiments at least one of the N mandibular activity classes is indicative of a sleep respiratory disturbance.

An aspect of the present disclosure relates to a method for assisting in the characterization of respiratory effort of a subject being provided with a sensor comprising a gyroscope configured for detecting the movement of the subject's mandible during sleep, the method comprising the steps:

outputting, by the sensor preferably the gyroscope, a signal indicative of mandibular activity;

receiving, by a data analysis unit, said signal indicative of mandibular activity;

storing, by means of a memory unit comprised in the data analysis unit, N mandibular activity classes, N being an integer larger than one; wherein at least one of the N mandibular activity classes is indicative of a sleep disturbed breathing;

wherein each $j^{th}$ ($1 \leq j \leq N$) mandible movement class consists of a $j^{th}$ set of rotational values, each $j^{th}$ set of rotational values being indicative of at least one rate of mandibular rotations;

associated with the $j^{th}$ class;

sampling, by means of a sampling element comprised in the data analysis unit, the mandibular activity data during a sampling period, thereby obtaining sampled mandibular activity data;

deriving, by means of the data analysis unit, a plurality of mandibular activity values from the sampled mandibular activity data; and, matching, by means of the data analysis unit, the mandibular activity values to the N mandibular activity classes of which at least one of the N mandibular activity class is indicative of a sleep disturbed breathing.

EXAMPLES

To better illustrate the properties, advantages and features of the present disclosure some preferred embodiments are disclosed as examples with reference to the enclosed figures. However, the scope of the present disclosure is by no means limited to the illustrative examples described below.

Example 1: Wearable Device Design

With reference to FIG. 2, a wearable (10) according to an embodiment of the present disclosure is shown. The wearable (10) comprises at least one left electrode (100) and at least one right electrode (not shown). Each electrode (100) is connected to a garment (200), specifically a collar by means of at least one connective cable (150). The collar may house the stimulator and any ancillary devices, such as a power source e.g. battery pack configured for powering the stimulator, and a controller for controlling the stimulation generated by the power source. The connective cable (150) then provides for an electrical connection between the electrodes (100) and the stimulator.

Figure 3:
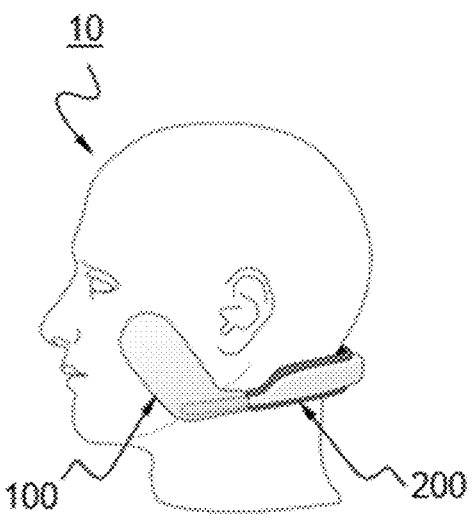
FIG. 3 is a perspective view of the wearable device (10) configured for stimulation of masseter muscles according to another preferred embodiment of the present invention.

With reference to FIG. 3, a wearable (10) according to another embodiment of the present disclosure is shown. The wearable (10) also comprises at least one left electrode (100) and at least one right electrode (not shown), which are connected to a garment (200), specifically a collar, by means of a rigid housing extending sideways from said collar. The connective housing allows the integration of one or more cables within. The collar may be configured to (lightly) press onto the subject's neck such that it remains fixed in place. Moreover, the collar can be configured to create a compression on the electrode, which may increase the stimulation response and/or decrease discomfort.

With reference to FIG. 5, a wearable (10) according to another embodiment of the present disclosure is shown. The wearable (10) also comprises at least one left electrode (100) and at least one right electrode (not shown), which are connected to a garment (200), specifically a headband, by means of a rigid housing extending downwards from said headband. The collar may be configured to (lightly) press onto the subject's head such that it remains fixed in place.

Example 2: Stimulation Zone

To achieve an optimal stimulation response and/or reduced stimulation discomfort, each electrode (100) of the wearable may be positioned into electrical contact with a selected portion of the subject's skin. The preferred skin portion is illustrated in FIG. 1 and ranges from a subject's masseter muscle motor point to a posterior angle of the subject's mandible.

Figure 7:
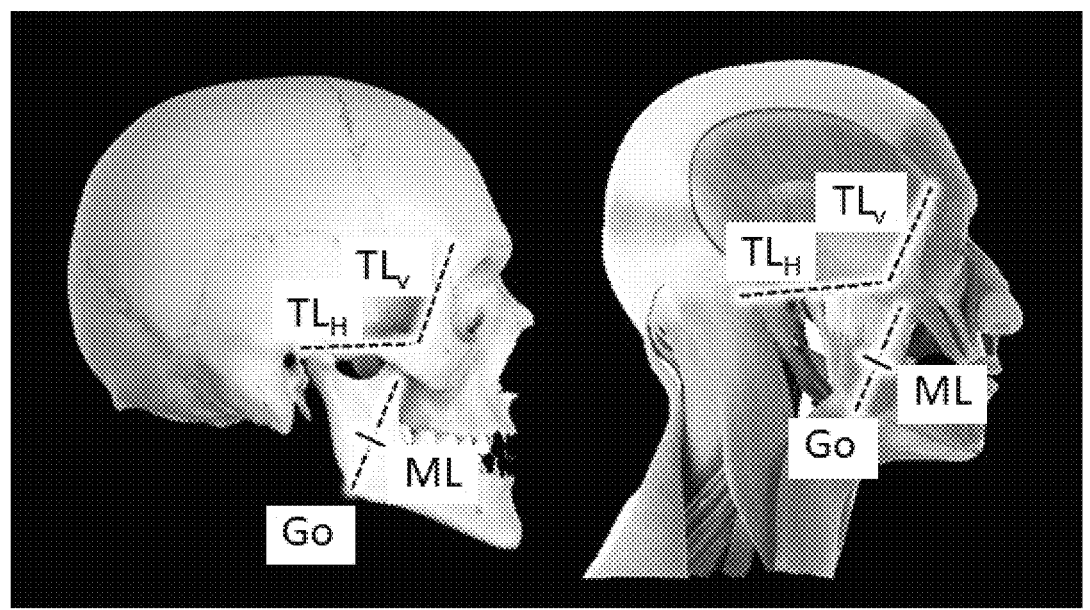
FIG. 7 is a lateral view of a skull with reference landmarks and lines for identifying the stimulation region (S) according to another preferred embodiment of the present invention.
Figure 8:
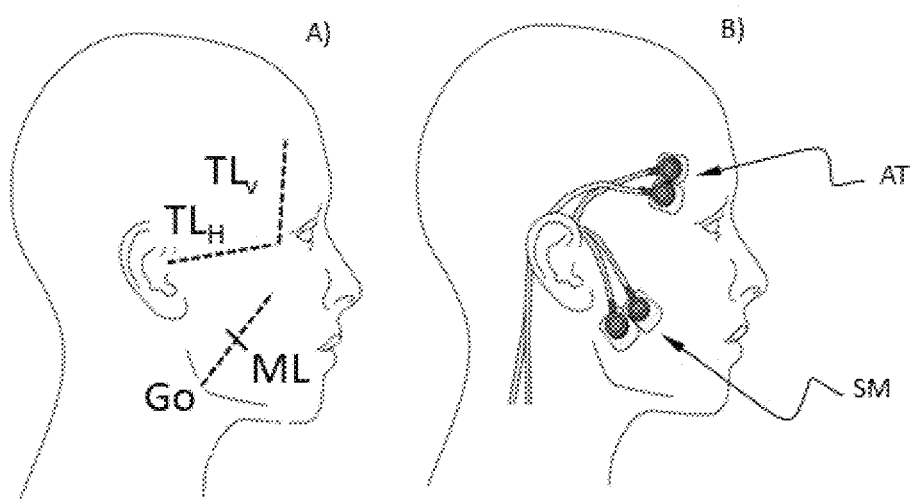
FIG. 8 is a lateral view of a head with reference landmarks and lines for identifying the stimulation region (S) according to another preferred embodiment of the present invention.

In order to locate the areas of interest over the superficial masseter (SM) muscle, one straight line can be determined from easily palpable anatomical landmarks. With reference to FIG. 7 these landmarks can be identified. Specifically, FIG. 7A shows the lateral view of a skulls with the reference lines, $TL_V$, $TL_H$ and ML. The small thick line represents an intersection about 40% length of the masseter muscle line (ML) from Gonion (Go). FIG. 7B further shows a lateral view of deep facial planes, evidencing the anterior temporalis (AT) and superficial masseter (SM) muscles and their relationship with anatomical landmarks and reference lines adopted. With further reference to FIG. 8 the same landmarks are drawn on the face of a human subject. Specifically, FIG. 8A shows the lateral view of a subject's head with the same reference lines, $TL_V$, $TL_H$ and ML. Further, FIG. 8B shows the placement of electrodes over the AT and SM muscles. In a clinical setting, optimal placement of electrodes over the superficial masseter (SM) muscle, gonion—located at the angle of the mandible (gonial angle)—and the body of zygomatic bone can be performed through palpation to identify anatomical reference landmarks. The superficial masseter muscle line is drawn from these reference landmarks, joining gonion, spotted on the soft tissue, to the mid-point between the lower posterior border of the zygomatic bone and the zygomatic arch, both also identified by palpation.

The line is adjusted to fibres direction of superficial masseter muscle, which is congruent with its origin and insertion. The superficial masseter muscle is covered by a tendinous layer that extends from the zygomatic bone to ⅓ to ½ of its length. It is not recommended to place electrodes over tendinous areas, so a reference point is identified at 40% of the length of line from the gonion or gonial angle (Go). The electrodes are placed along this reference line, with their location of placement on the mark corresponding to 40% of the line.

After setting out all the reference points and lines, the subject may be asked to clench the teeth so as to confirm whether the suggested anatomical landmarks needed any adjustments.

The surface electrodes are advantageously placed along the muscle fibres, over the most prominent region at the moment of muscle contraction to improve stimulation response. While palpating the muscle during contraction, it can be possible to verify electrodes positioning to perform any need of correction. In a home setting, optimal placement of electrodes onto the preferred stimulation zone (S) can be achieved by following the steps of an easier user guide. With reference to FIG. 9, this placement guide will be discussed as a method comprising the following steps:

FIG. 9 (i) identifying the gonial angle (Go); preferably at the outer corner of the mandible;

FIG. 9 (ii) identifying the zygomatic arch (Za); preferably at the outer corner of the eye;

FIG. 9 (iii) identifying a muscle extending from Go towards Za; preferably by gritting the teeth to contract this muscle;

FIG. 9 (iv) identifying a target stimulation zone (S) ranging from the Go towards the centre of the identified muscle determined along the direction of the muscle fibres;

FIG. 9 (v) placing of at least one electrode over the stimulation zone (S), preferably a bipolar electrode wherein one electrode is placed adjacent to the gonial angle (Go) and the other electrode is placed adjacent to the centre of the identified muscle determined along the direction of the muscle fibres. An example of a bipolar electrode is shown in FIG. 9.

It is understood that variations on the above-discussed method may be developed to identify the same target stimulation by identifying different anatomical landmarks. Nonetheless, this method presents a particularly easy to follow guide for at-home and/or clinical applications of the wearable device and accordingly forms a preferred embodiment of the present disclosure.

Example 3: Stimulation Effects

In order to assess the viability of an electrical stimulation on the target stimulation zone (as defined in Example 2) a number of research protocols has been set up on different subjects with various stimulation parameters. The recorded data is discussed below.

Short-Term Effect

The efficacy of a transcutaneous electrical stimulation with a high current intensity at a low frequency with narrow pulse width was verified to determine if recruiting the muscular fibres may provide for a direct and acute response to prevent the occurrence of a sleep disturbance.

One subject was selected for overnight stimulation. The subject was 53 years old female volunteer with BMI of 26.2 $kg/m^2$. The sleeping stage was monitored using laboratory polysomnography. Airflow was measured by means of a pressure transducer and thermistor.

The electrical stimulation was applied to the masseter muscles through two electrodes placed above the motor point of the muscles and on the posterior angle of the mandible, respectively. The electrode consisted of a bipolar surface electrode with an inter electrode distance of 20 mm, 14 mm diameter for conductive area, adhesive wet gel and foam backing backed. The stimulation consisted of a biphasic pulse current at a frequency of 40 Hz with a current intensity of 7 mA, a pulse width of 250 μs and activation periods of five seconds of stimulation and five seconds of rest.

The results indicated that the electrical stimulation caused a direct muscle response that results in an elevation of the mandible sufficient to maintain good air flow throughout the any sleeping stage, specifically the N2 stage. Accordingly, the occurrence of sleep disturbances could be prevented by means of the applied electrical stimulation.

Long-Term Effect Two subjects were selected for overnight stimulation. The first subject was 61 years old male volunteer with BMI of 24.8 $kg/m^2$. The second subject was 38 years old male volunteer with BMI of 29.8 $kg/m^2$. The respiratory event index (OAHI—obstructive apnea hypopnea index) and the sleep fragmentation index (ArI—arousal index) were measured during laboratory polysomnography for both patients at baseline (week 0), after one week of stimulation (week 1) and one week after the stimulation was switched off (week 2).

The electrical stimulation was applied to the masseter muscles through two electrodes placed above the motor point of the muscles and on the posterior angle of the mandible, respectively. The electrode consisted of a bipolar surface electrode with an inter electrode distance of 20 mm, 14 mm diameter for conductive area, adhesive wet gel and foam backing backed. The stimulation consisted of a biphasic pulse current at a frequency of 40 Hz, with a pulse width of 250 µs, activation periods of five seconds of stimulation and five seconds of rest, and a current with a current intensity of 6 and 8 mA, respectively.

The results of the first subject are presented in the table below:

| Condition | OAHI (events/h) | Arl (events/h) |
| --- | --- | --- |
| Week 0 | 31.7 | 39.8 |
| Week 1 | 12.6 | 23.2 |
| Week 2 | 22.4 | 32.1 |

Respiratory Events

Six subjects were selected for overnight stimulation. The reduction of the respiratory event index (OAHI—obstructive apnea hypopnea index) and of the sleep fragmentation index (ArI—arousal index) were measured during laboratory polysomnography after two weeks of stimulation compared to baseline values.

Electrical stimulation was applied to the masseter muscles through two electrodes placed above the motor point of the muscles and on the posterior angle of the mandible, respectively. Bipolar surface electrode with inter electrode distance of 20 mm, 14 mm diameter for conductive area, adhesive wet gel, foam backing backed was mounted on the face of a volunteer individual with normal occlusion, awake. The participants were allocated to one of two stimulation protocols, varying the rest-duration period of the night stimulation (protocol A: 5 sec ON/5 sec OFF without pause throughout the night; protocol B: 5 sec ON/5 sec OFF with 1 minute pause every minute of stimulation throughout the night). The results are presented below in Table 1.

TABLE 1

| electrical stimulation parameters and stimulation response | | | | | | |
| --- | --- | --- | --- | --- | --- | --- |
| Stimulation parameters | Mean age (years) | Gender | Mean BMI (kg/m²) | Mean current intensity after 2 weeks (mA) | OAHI* (events/h) | Arl** (events/h) |
| 40 Hz 250 µs 5s on 5s off | 43.3 | 1 female + 2 males | 27.6 | 5.6 | −66% | −32% |
| 40 Hz 250 µs 5s on 5s off - 1 min rest for every 1 min stim | 48.3 | 1 female + 2 males | 27.9 | 5.5 | −45% | −21% |

*Obstructive apnea hypopnea (OAHI) index indicates the mean reduction of the respiratory events
**arousal index (Arl) indicates the mean reduction of the sleep fragmentation The data of the first subject demonstrate that after one week (week 1) of stimulation a decrease of 60.3% for OHAI can be observed. After the following week (week 2) without stimulation still a decrease of 29.3% for OAHI persists compared to the baseline (week 0).

The results of the second subject are presented in the table below:

| Condition | OAHI (events/h) | Arl (events/h) |
| --- | --- | --- |
| Week 0 | 15.6 | 38.3 |
| Week 1 | 3.4 | 23.6 |
| Week 2 | 11.4 | 30.2 |

The data of the second subject demonstrate that after one week (week 1) of stimulation a decrease of 78.2% for OHAI can be observed. After the following week (week 2) without stimulation still a decrease of 26.9% for OAHI persists compared to the baseline (week 0).

The results indicated that the electrical stimulation caused a retraining of the muscles with a delayed response effect that improved the beneficial effects of the stimulation across successive stimulation sessions and provided persisting effects even after the stimulation was terminated.

The results presented above in Table 1 indicate that transcutaneous electrical stimulation applied to the masseter muscles are effective in reducing the occurrence of respiratory events and arousal index by a substantial amount. The reduction of the occurrence of respiratory events and arousal index was more important for the group without the 1 minute pause every minute of stimulation.

Example 4: Stimulation Parameters

The implementation of an electrical stimulation on a target stimulation zone was assessed on different subjects using various stimulation parameters and electrode set-ups. The results are discussed throughout present Example 4.

Electrode Type

Bipolar surface electrode was mounted on the face of a volunteer individual with normal occlusion, awake. The electrical stimulation was applied as a biphasic pulse current at a frequency of 40 Hz, with a width of 250 µs and activation periods of five seconds of stimulation and five seconds of rest. The closing force of the jaw was evaluated using a pressure sensor implemented in a bite (FUTEK Advanced Sensor Technology, Inc., Irvine, California, USA). Electrodes are positioned on the masseter and the temporalis muscles according to the preferred method described in Example 2. The results are presented below in Table 2.

TABLE 2

| | | | | | Reported comfort | |
| Electrode type and position* | Type of gel** and backing*** | Diameter of conductive area (mm) | Inter electrode distance (mm) | Maximum tolerated current (mA) | (visual scale 0 to 10) | Closing force of the jaw (Nm) |
|---|---|---|---|---|---|---|
| Type 1a (SM) | awg, fbb | 14 | 20 | 10 | 9 | 42 |
| Type 1b (SM) | awg, fbb | 14 | 30 | 5.5 | 4 | 25 |
| Type 2 (SM) | awg, fbb | 25 | 20 | 6 | 6 | 30 |
| Type 3 (SM) | awg, tb | 14 | 30 | 5.5 | 4 | 25 |
| Type 4 (SM) | awf, fbb | 14 | 20 | 6.5 | 6 | 30 |
| Type 1a (SM + AT) | awg, fbb | 14 | 20 | 10 mA SM 2 mA AT | 9 | 45 |
| Type 1b (SM + AT) | awg, fbb | 14 | 30 | 5.5 mA SM 4 mA AT | 4 | 27 |
| Type 2 (SM + AT) | awg, fbb | 25 | 20 | 6 mA SM 1.5 mA AT | 6 | 32 |
| Type 3 (SM + AT) | awg, tb | 14 | 30 | 5.5 mA SM 4 mA AT | 4 | 27 |
| Type 4 (SM + AT) | awf, fbb | 14 | 20 | 6.5 mA SM 2.5 mA AT | 6 | 32 |

*Anterior temporalis (AT) and/or superficial masseter (SM) muscles

**Adhesive wet gel (awg); Adhesive wet foam (awf)

**Foam backing backed (fbb); Tissue backed (tb)

The results presented above in Table 2 indicate that a bipolar surface electrode mounted on the masseter muscles with an inter electrode distance of 20 mm, 14 mm diameter for conductive area, adhesive wet gel and foam backing backed provides for the highest reported comfort level (9 out of 10 on a visual scale) while also stimulates a strong closing force of the jaw (42 Nm). Similar results are obtained for the same bipolar surface electrode mounted on the masseter and temporalis muscles.

Electrode Positioning

Bipolar surface electrode with inter electrode distance of 20 mm, 14 mm diameter for conductive area, adhesive wet gel, foam backing backed was mounted on the face of a volunteer individual with normal occlusion, awake. The electrical stimulation was applied as a biphasic pulse current at a frequency of 40 Hz, with a width of 250 μs and activation periods of five seconds of stimulation and five seconds of rest. The closing force of the jaw was evaluated using a pressure sensor implemented in a bite (FUTEK Advanced Sensor Technology, Inc., Irvine, California, USA). The results are presented below in Table 3.

TABLE 3

| Electrode position* | Description of the position of the electrodes | Maximum tolerated current (mA) | Reported comfort (visual scale 0 to 10) | Closing force of the jaw (Nm) |
|---|---|---|---|---|
| Position 1 (SM) | Positioned on the SM as described in Example 2 | 10 | 9 | 42 |
| Position 2 (SM) | 90° rotation of the electrodes | 8 | 4 | 24 |

TABLE 3-continued electrical stimulation parameters and stimulation response

| Electrode position* | Description of the position of the electrodes | Maximum tolerated current (mA) | Reported comfort (visual scale 0 to 10) | Closing force of the jaw (Nm) |
|---|---|---|---|---|
| Position 3 (SM) | Upper part of the SM | 5 | 3 | 4 |
| Position 1 (AT) | Positioned on the AT as described in Example 2 | 2 | 4 | 4 |
| Position 2 (AT) | 90° rotation of the electrodes | 2 | 3 | 2 |
| Position 3 (AT) | Lower part of the temporalis - 30° rotation | 1.5 | 2 | 2 |
| Position 1 (SM + AT) | Positioned on the SM and the AT as described in Example 2 | 10 mA SM 2 mA AT | 9 | 45 |
| Position 2 (SM + AT) | 90° rotation of the electrodes | 8 mA SM 2 mA AT | 4 | 25 |

*Anterior temporalis (AT) and/or superficial masseter (SM) muscles he results presented above in Table 3 indicate that a bipolar surface electrode mounted on the target stimulation zone on the masseter muscles and optionally on the temporalis muscles according to the method as described in Example 2 provides for the highest reported comfort level (9 out of 10 on a visual scale) while also stimulate a strong closing force of the jaw (42 Nm).

Stimulation Parameters

Bipolar surface electrode with inter electrode distance of 20 mm, 14 mm diameter for conductive area, adhesive wet gel, foam backing backed was mounted on the face of a volunteer individual with normal occlusion, awake. The bipolar surface electrode mounted on the target stimulation zone on the masseter muscles according to the method as described in Example 2. The electrical stimulation was applied as a biphasic pulse current with activation periods of five seconds of stimulation and five seconds of rest. The closing force of the jaw was evaluated using a pressure sensor implemented in a bite (FUTEK Advanced Sensor Technology, Inc., Irvine, California, USA). Electrodes are positioned on the masseter and the temporalis muscles according to the preferred method described in Example 2. The results are presented below in Table 4.

TABLE 4 electrical stimulation parameters and stimulation response

| Stimulation parameters | Maximum tolerated current (mA) | Reported comfort (visual scale 0 to 10) | Closing force of the jaw (Nm) |
|---|---|---|---|
| 40 Hz 250 μs | 10 | 9 | 42 |
| 60 Hz 250 μs | 6.5 | 5 | 28 |
| 20 Hz 250 μs | 12.5 | 6 | 33 |
| 40 Hz 150 μs | 14.5 | 7 | 40 |
| 40 Hz 350 μs | 8.5 | 6 | 31 |

The results presented above in Table 4 indicate that an electrical stimulation with a frequency of 40 Hz and a pulse width of 250 μs provide for the highest reported comfort level (9 out of 10 on a visual scale) while also stimulate a strong closing force of the jaw (42 Nm).

It is understood that the embodiments presented in Tables 2-4 of present Example 3 form preferred embodiments of the wearable device of the present disclosure.

Example 5: Sensing Unit Feedback

The wearable (10) of the present disclosure may be provided with a sensing unit configured for recording of mandibular movement of the subject's mandible. For example, the sensing unit may comprise a gyroscope and/or accelerometer mounted on at least one electrode (100), preferably both a gyroscope and/or accelerometer mounted on at least one electrode (100). The mandibular movement may refer to any changes in the position of the subject's mandible or any rotations or displacements of the subject's mandible. The mandibular movement may be recorded by sensing unit as mandibular activity data.

Additionally, the sensing unit may also be configured to record data related to the subject's respiration activity or sleeping activity. The respiration activity data may refer to any data related to the subject's respiration, such as breathing rate or intensity. respiration activity data may also be derived from the mandibular activity data or combined with the mandibular activity data. Similarly, the sleeping activity data may refer to any data related to the subject's sleeping, such as sleep related movements. Sleeping activity data may also be derived from the mandibular activity data or combined with the mandibular activity data. espiration activity data may also be combined with the sleeping activity data.

Figure 11:
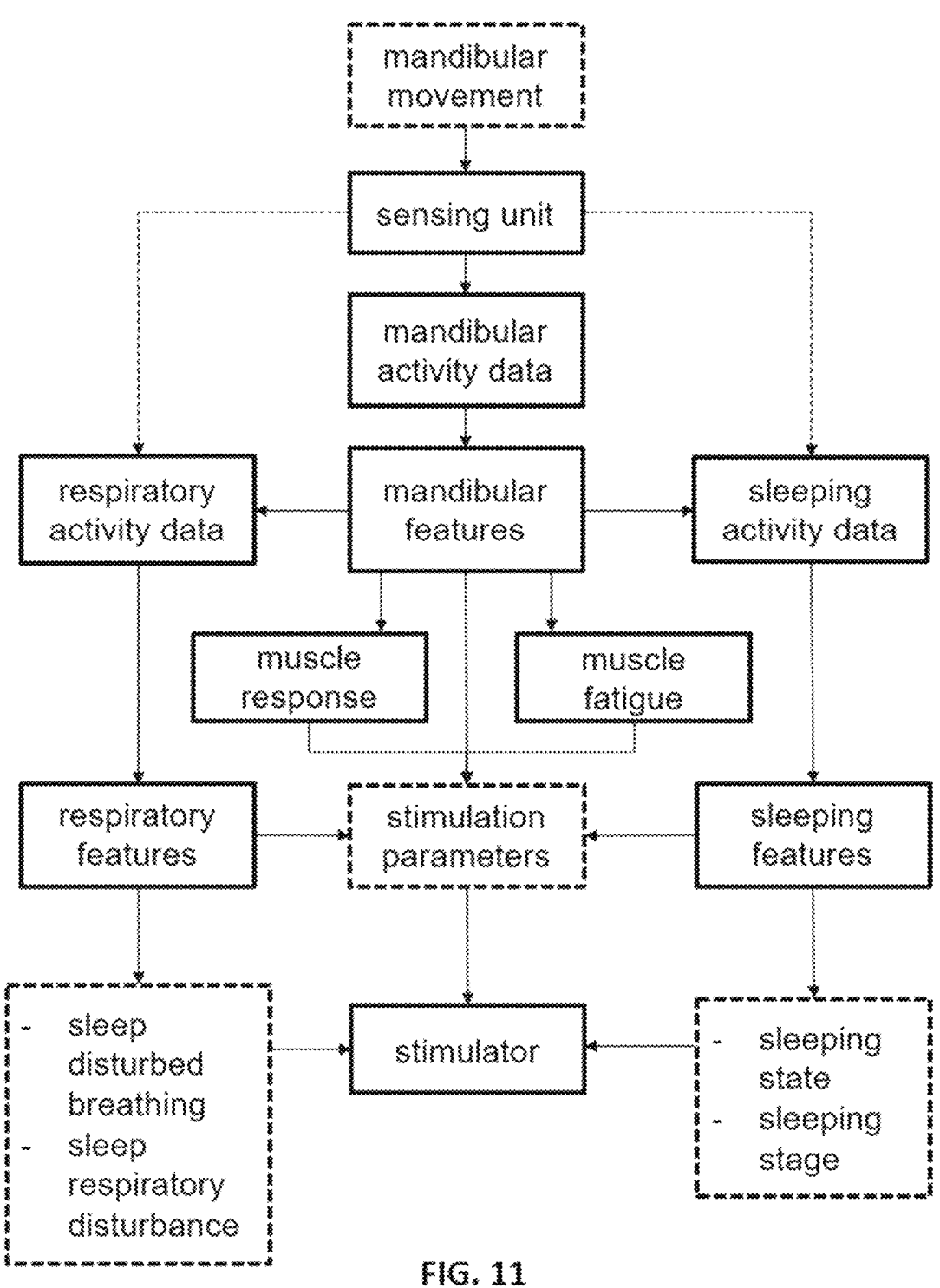
FIG. 11 is a schematic of the working principle of the wearable device (10) according to a preferred embodiment of the present invention.

The mandibular activity data, respiration activity data and sleeping activity data may be analysed to provide a feedback loop to the stimulator to improve the stimulation efficacy and reduce the occurrence of drawbacks. An exemplary working principle of feedback loop according to a preferred embodiment of the present disclosure is presented in FIG. 11. Below some exemplary embodiments are presented which were found to be particularly well-suited for the present invention. It is, however, understood that the various embodiments described in the present disclosure may be combined in any suitable manner, as would be apparent to a person skilled in the art from this disclosure.

In a particular embodiment the mandibular activity data may be analysed to determine a stimulation response, which may include the elevation and stabilisation of the subject's mandible and instruct the stimulator to adjust one or more stimulation parameters to control the elevation and stabilisation of the subject's mandible. It may also be used to determine the occurrence of muscle fatigue.

In a particular embodiment the respiration activity data may be analysed to determine sleep disturbed breathing marked with increased respiratory effort and instruct the stimulator to adjust one or more stimulation parameters to decrease the respiratory effort.

In a particular embodiment the respiration activity data may be analysed to determine a sleep respiratory disturbance and instruct the stimulator to adjust one or more stimulation parameters to reduce the intensity of the sleep respiratory disturbance or prevent the occurrence of a further sleep respiratory disturbance.

In a particular embodiment the sleep activity data may be analysed to determine sleeping states, such as an awake state and an asleep state. The stimulator may be instructed to initiate the electrical stimulation when the subject falls asleep and terminate the electrical stimulation when the subject awakes.

In a particular embodiment the sleep activity data may be analysed to determine sleeping stages, which may include a light sleeping (N1) stage, a light sleeping (N2) stage, a REM stage, and/or a deep sleeping (N3) stage. The stimulator may be instructed to initiate the electrical stimulation when the subject enters the light sleeping (N1) stage, the light sleeping (N2) stage and/or the REM stage and terminate the electrical stimulation when the subject enters the deep sleeping (N3) stage.

Example 6: Sleeping Stage Detection

In order to assess the viability of a sleeping stage determination module a research protocol has been set up according to the following parameters. Mandibular movement data (MM) was collected from 30 participants, each participant was provided with a "chin sensor" and a "cheek sensor". The check sensor was located at the preferred target stimulation zone discussed in Example 2 of the present disclosure, i.e., at the same location as the electrode. The research aimed to identify differences in sleep analysis quality based on MM data obtained from the chin sensor and the cheek sensor. The feasibility of implementing an accurate sleeping stage determination module in the wearable device as disclosed herein can be assessed based on these results.

Primary Objectives

Detection of sleep/wake states from cheek-derived MM with enough performances.

Determination of sleep/wake detection rules for cheek MM data that can efficiently approximate sleep/wake algorithm analysis from the chin sensor.

Hypothesis

Total sleeping time (TST) differences between the cheek and the chin MM sensor are no greater than what is expected from interscorer variability (~85%).

Application of simple detection rules to cheek-derived MM features should allow for detection of sleep and wake states with >75% accuracy.

Methods

Prospective study of consenting adult patients referred for a single overnight in-laboratory polysomnography (PSG), complemented by simultaneous mandibular movements (MM) recording using two devices. Data samples from 30 participants were obtained by enrolling subjects from routine practice in a sleep laboratory during a 3-month period.

The study apparatus consisted of 2 coin-sized devices attached by the sleep technician on the chin (between the inferior labial sulcus and the pogonion) and the cheek (on the surface of the masseter muscle) of the participants, respectively.

Results and Processing

Figures 12, 13:
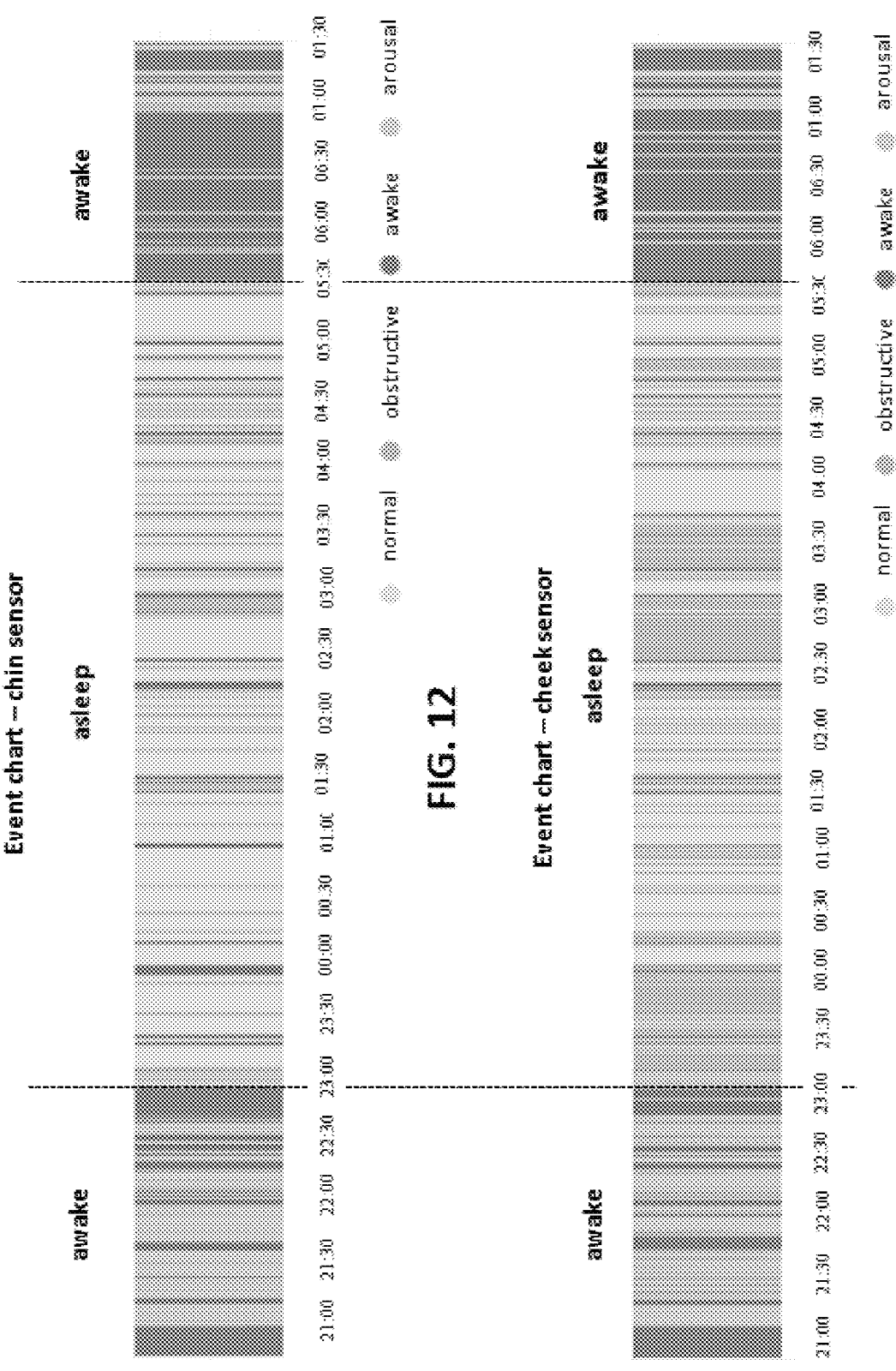
FIG. 12 shows the mandibular movement (MM data) recorded by a chin sensor for the sleeping stage study discussed in Example 6.
FIG. 13 shows the mandibular movement (MM data) recorded by a cheek sensor for the sleeping stage study discussed in Example 6.

The MM data of a single selected participant recorded with the chin sensor is shown in FIG. 12 and the corresponding MM data recorded with the cheek sensor is shown in FIG. 13. The figures indicate the occurrence of sleeping states and obstructive respiratory events with respect to the time of night (x-axis). The MM data is divided into 3 parts based on the awake and asleep states as recorded by the sensors. The occurrence of obstructive respiratory events is indicated on the MM data—differences may be attributed to algorithm calibration.

The collected MM data were automatically transferred to a cloud-based infrastructure at the end of the night, and data analysis was conducted with a dedicated machine-learning algorithm. The algorithm analysed the time series data from the cheek device in order to precisely identify sequential 30 seconds epochs of MM raw signals as wake or sleep, based on relevant and non-redundant features. Each 30 seconds epoch was summarized by 11 features extracted from the gyroscope norm:

a. Standard deviation
b. Minimum values and differences in minimum values in adjacent 30 sec windows
c. Maximum values and differences in maximum values in adjacent 30 sec windows
d. Median value and differences in median values in adjacent 30 sec windows
e. 1st quartile and differences in Q1 values in adjacent 30 sec windows
f. 3rd quartile and differences in Q3 values in adjacent 30 sec windows For the purposes of this study gyroscope data was selected as it is more sensitive to sleep/wake variations; accelerometer data was not considered. Normalized histograms were produced to investigate the distribution of these features in both sleep and wake.

Algorithm-derived sleep/wake labels were extracted from the chin sensor. The relevant features were extracted from the corresponding MM raw signal sequences and were used as input data for the algorithm to determine whether they pertained to wake or sleep states.

Figure 14:
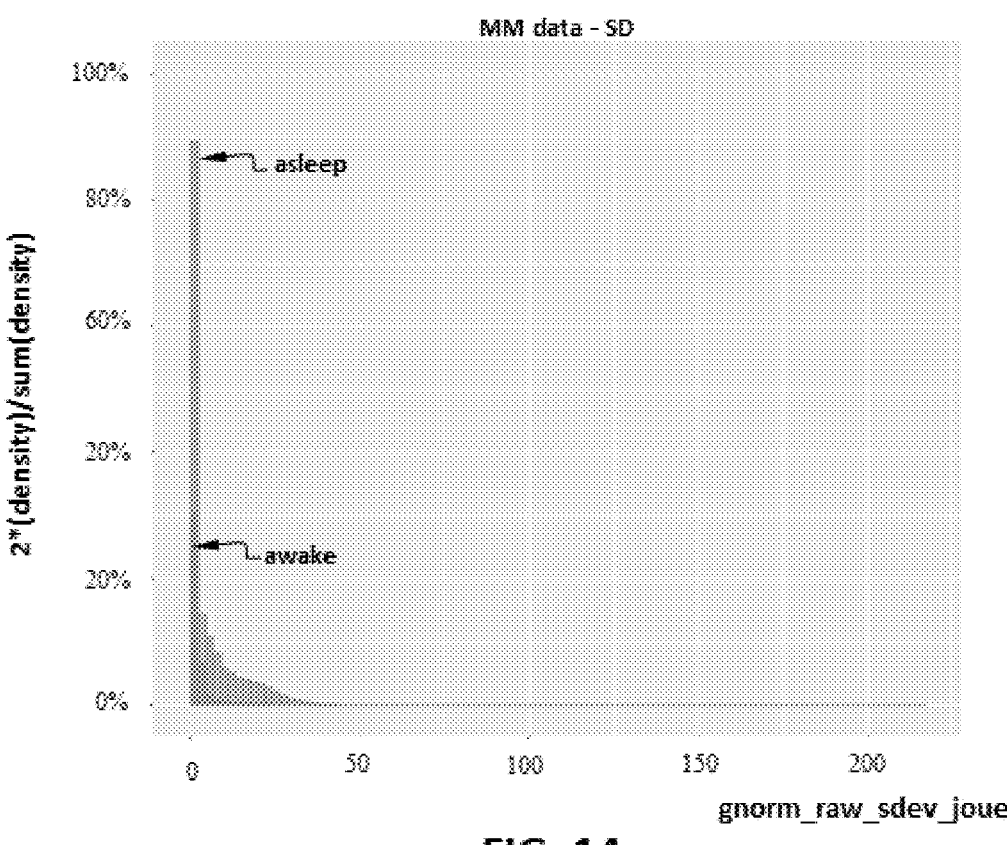
FIG. 14 shows the frequency distribution of standard deviation (SD) values for both sleep (light) and wake (dark) states as discussed in Example 6.
Figure 15:
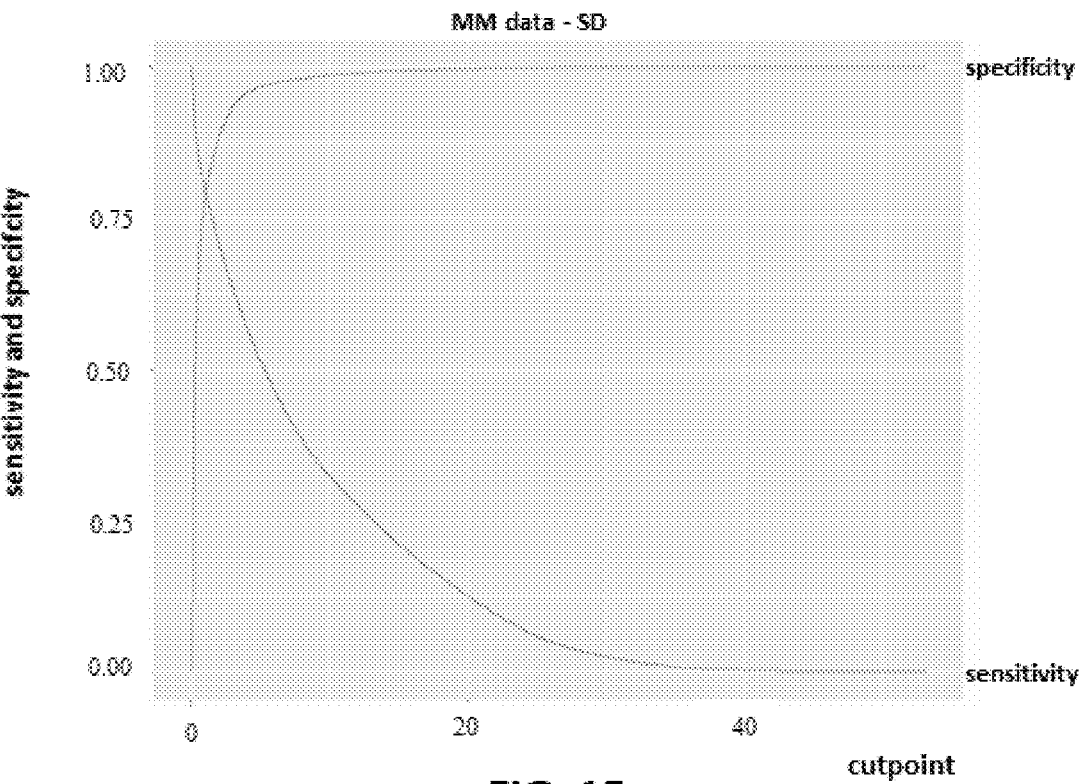
FIG. 15 shows the sensitivity/specificity across all possible SD values for detection of sleep and wake state for the sleeping stage study as discussed in Example 6.
Figure 16:
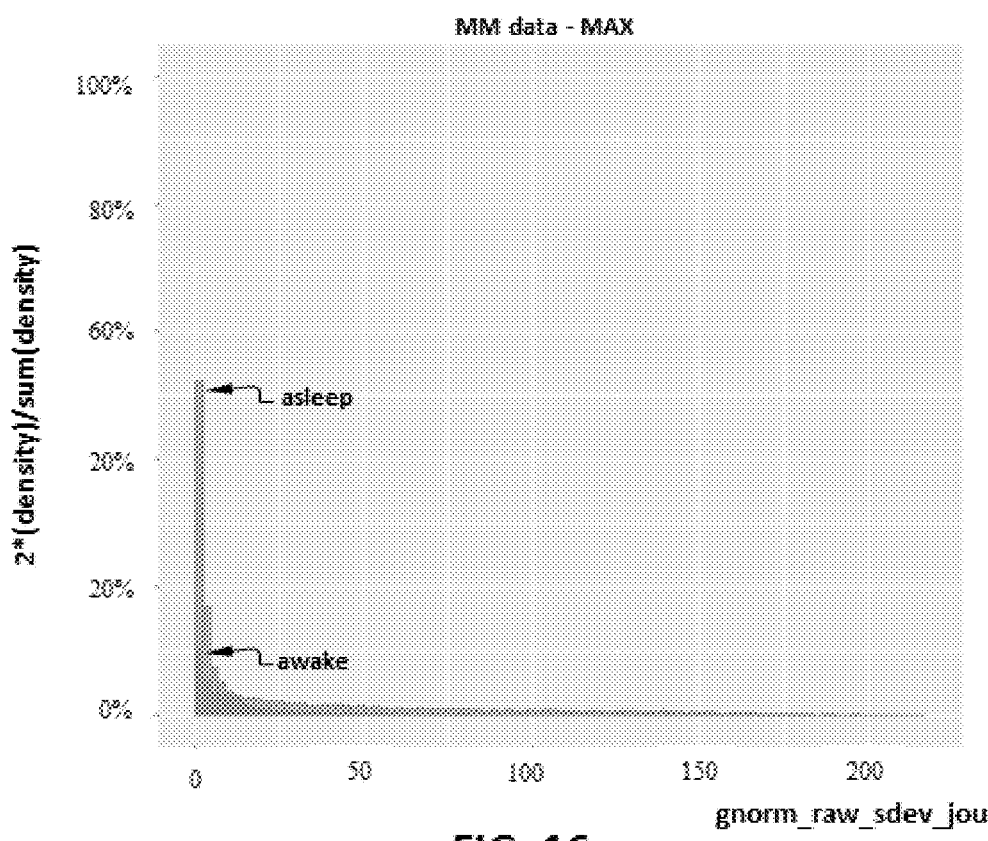
FIG. 16 shows the frequency distribution of maximum (MAX) values for both sleep (light) and wake (dark) states as discussed in Example 6.
Figure 17:
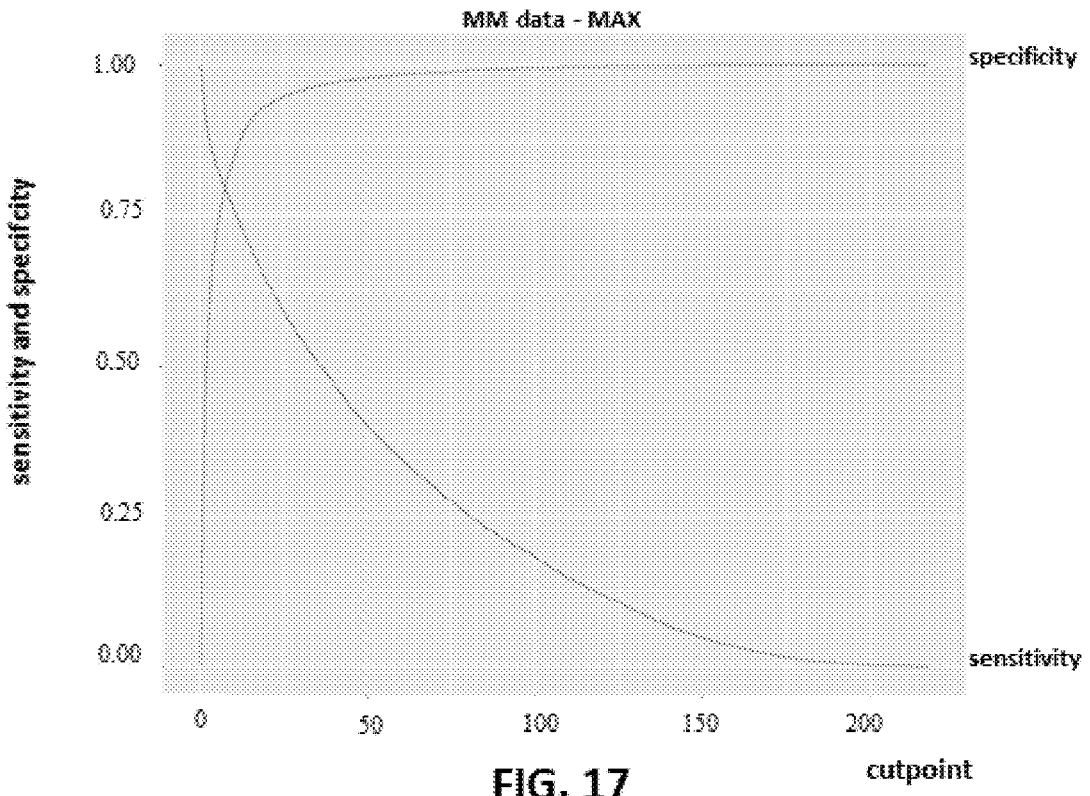
FIG. 17 shows the sensitivity/specificity across all possible MAX values for detection of sleep and wake state as discussed in Example 6.

The cheek-derived MM features were then used to best classify the chin-derived sleep/wake labels. This investigation led to the selection of 2 features with the most discriminative power: standard deviation (SD) and maximum value (MAX) of the MM data recorded by the gyroscope. The processed data is shown with reference to FIG. 14-17. Specifically, FIG. 14 shows the frequency distribution of SD values for both sleep (light) and wake (dark) states. FIG. 15 shows the sensitivity/specificity across all possible SD values for detection of sleep and wake state. FIG. 16 shows the frequency distribution of MAX values for both sleep (light) and wake (dark) states. Finally, FIG. 17 shows the sensitivity/specificity across all possible MAX values for detection of sleep and wake state.

Data Analysis

The data analysis algorithm can be configured for automated detection of sleep and wake states by considering the sensitivity/specificity values and the processed cheek-derived MM features. Additionally, the cut-offs for optimizing the detection of sleep/wake states can be kept generic (i.e., cut-offs are kept the same across all individuals—FIG. 18) or personalised (i.e., cut-offs are adjusted to an individual's sleeping profile—FIG. 22). The cut-off values will have an impact on the total sleep time (TST), i.e., the amount of time that the individual spends actually sleeping during a planned sleep episode. The following parameters can be determined by comparing the chin TST data values to the cheek TST data, cheek SD and cheek MAX values: Diff_TST refers to the % difference between "Chin—data" and "Cheek—data"; Diff_TST1 refers to the % difference between "Chin—data" and "Cheek—SD"; and Diff_TST2 refers to the % difference between "Chin—data" and "Cheek—MAX". This data analysis algorithm may be implemented as a configuration of the sleep detection module of the present disclosure.

Three different implementations can be considered for the data analysis algorithm:

Wake state detection: The data analysis algorithm can be configured for optimal detection of the wake state by constraining the sensitivity to 0.9 and maximizing specificity. This configuration may for example maximize patients' comfort by preventing stimulation during the wake state and/or light sleep stages. However, the occurrence of episodes during the sleep state may be erroneously classified as awakening and terminate stimulation (thereby reducing stimulation efficiency).

Balanced wake/sleeping state detection: The data analysis algorithm can be configured for balanced detection of the awake and sleeping states by implementing a balance between specificity and sensitivity. This configuration is intended to accommodate sufficient subject comfort but still provide adequate stimulation length.

Sleeping state detection: The data analysis algorithm can be configured for optimal detection of the sleeping state by constraining the specificity to 0.9 and maximizing sensitivity. This configuration may for example maximize stimulation efficiency by preventing the occurrence of respiratory episodes. However, awaking episodes may be erroneously classified as asleep and continue stimulation (thereby reducing subject comfort).

Model 1—Fixed Cut-Offs

In a first model, the cut-offs for optimizing the detection of sleep/wake states have been selected irrespective of interindividual differences. A single optimal cut-off has been applied across patients. The cut-off configuration parameters are shown in FIG. 18.

The cut-off data selection is discussed with reference to FIG. 19-21. Specifically, FIG. 19 shows a Table with the data analysis algorithm configured for wake state detection, which results in a difference in total sleep time (TST) of 45% and a stimulation duration<4 h in 50% of subjects. FIG. 20 shows a Table with the data analysis algorithm configured for balanced wake/sleeping state detection, which results in a difference in TST of ~15% and a stimulation duration<4 h in 6.5% of subjects. FIG. 21 shows a Table with the data analysis algorithm configured for sleeping state detection, which results in a difference in TST of ~7% and a stimulation duration<4 h in 0% of subjects.

Model 2—Personalised Cut-Offs

In a second model, the cut-offs for optimizing the detection of sleep/wake states have been selected individually for each subject, hence personalizing the sleep/wake detection to their own sleeping profile. A different optimal cut-off has been applied to every subject. The cut-off configuration parameters are shown in FIG. 22.

Figure 23:
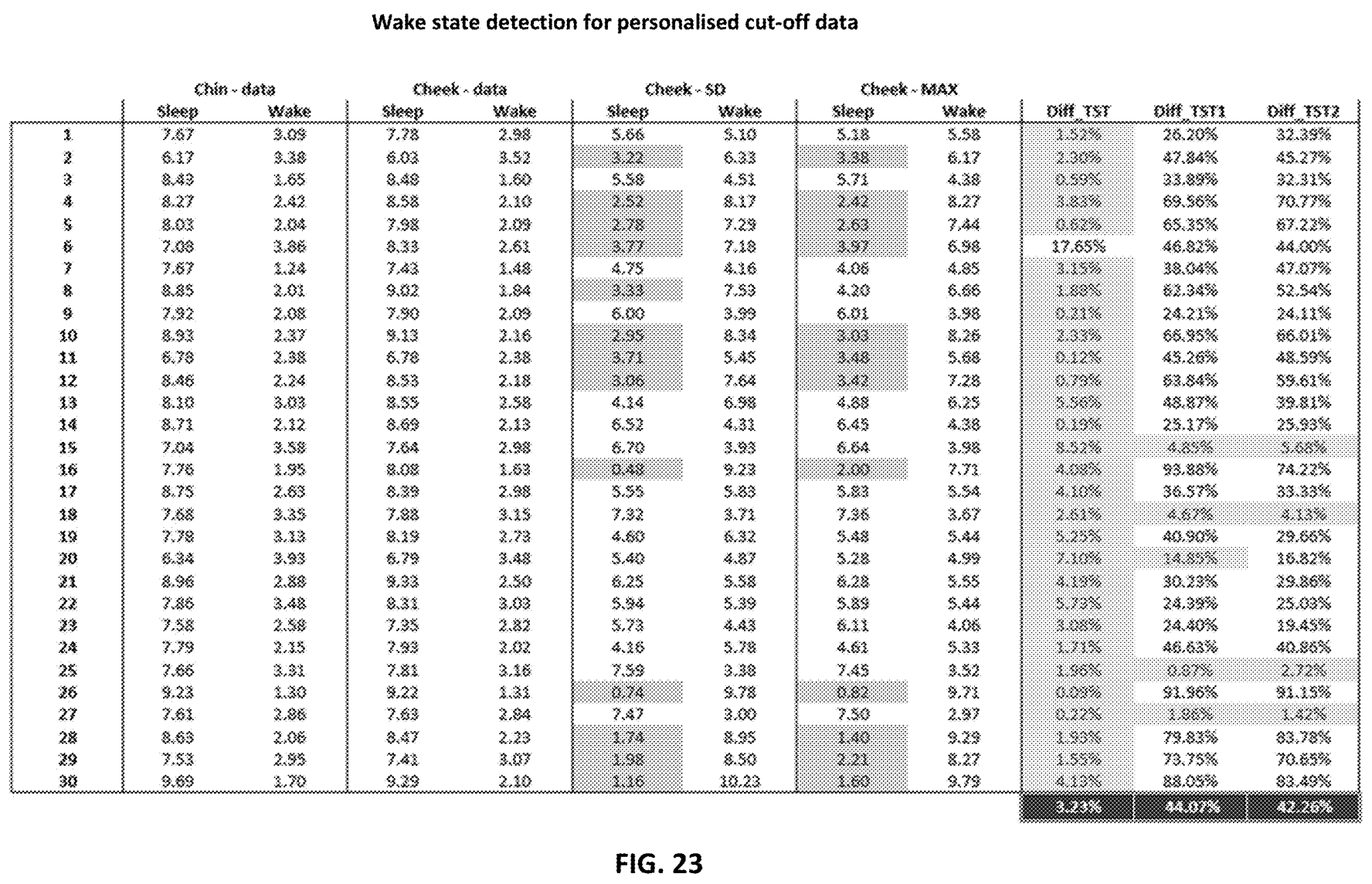
Figure 25:
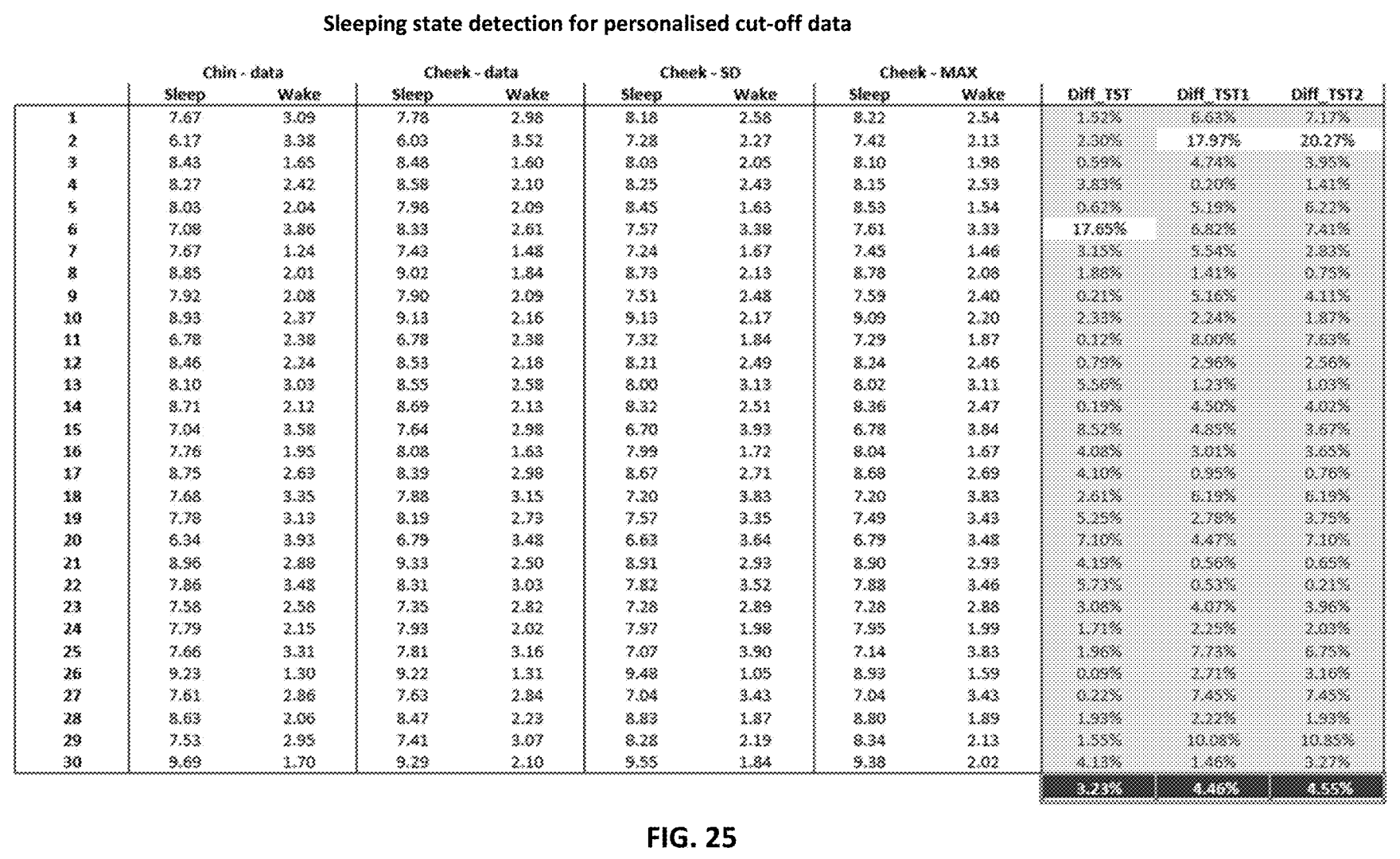

The cut-off data selection is discussed with reference to FIG. 23-25. Specifically, FIG. 23 shows a Table with the data analysis algorithm configured for wake state detection, which results in a difference in total sleep time (TST) of ~44% and a stimulation duration<4 h in 43.5% of subjects. FIG. 24 shows a Table with the data analysis algorithm configured for balanced wake/sleeping state detection, which results in a difference in TST of ~15% and a stimulation duration<4 h in 0% of subjects. FIG. 25 shows a Table with the data analysis algorithm configured for sleeping state detection, which results in a difference in TST of ~4.5% and a stimulation duration<4 h in 0% of subjects.

Conclusions

Based on the above presented results, it appears that a personalized optimization of sleep/wake detection cut-offs for the detection of sleep may provide better results both in terms of sleep and wake identification. This procedure leads to a variability in total sleep time (TST) that is inferior to 4.5% of the TST from the reference chin sensor. Bland-Altman analysis revealed a relatively tight distribution of the differences, with a systematic bias that is close to 0.

Figure 26:
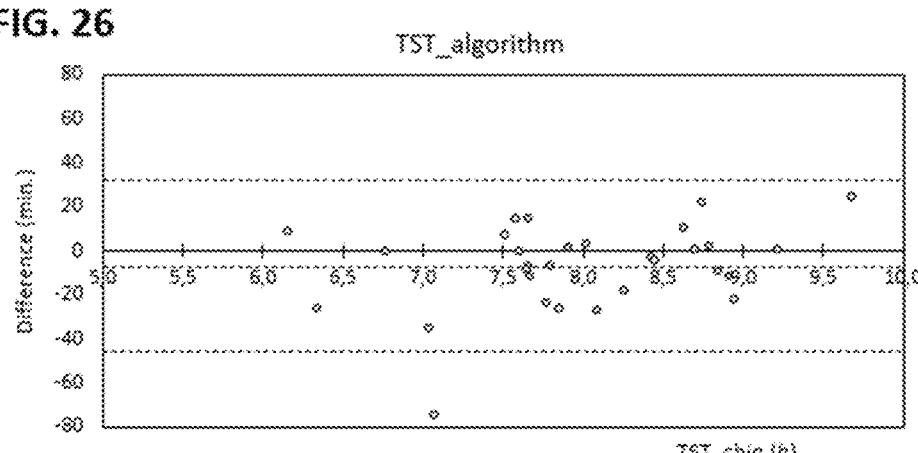
FIG. 26 shows a Bland-Altman graph of the comparison of chin sensor data with the algorithm data analysis of the cheek sensor data.

For comparison purposes, the analysis presents 3 Bland-Altman graphs of the following paired variables:

FIG. 26 shows a comparison of chin sensor data with the cheek sensor data.

Figure 27:
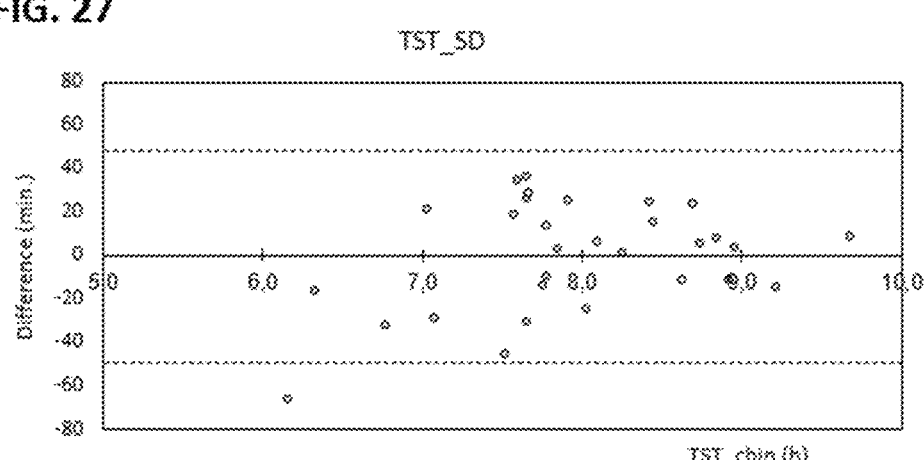
FIG. 27 shows a Bland-Altman graph of the comparison of the chin sensor data with the sleep/wake detection rule based on standard deviations (SD) of the cheek sensor data.

FIG. 27 shows a comparison of the chin sensor data with the sleep/wake detection rule based on standard deviations (SD) of the cheek sensor data.

Figure 28:
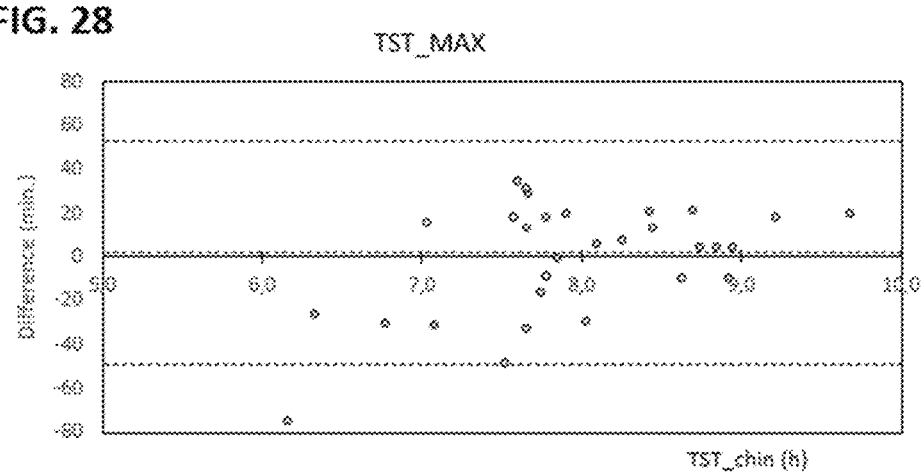
FIG. 28 shows a Bland-Altman graph of the comparison of the chin sensor data with the sleep/wake detection rule based on maximum values (MAX) of the cheek sensor data.

FIG. 28 shows a comparison of the chin sensor data with the sleep/wake detection rule based on maximum values (MAX) of the cheek sensor data.

Altogether, these data suggest that it is possible to detect sleep/wake phases with a MM recording device incorporated in the wearable device and mounted near the stimulation zone. The primary objective of the device would be to detect sleep and wake phases in order to actively pilot the stimulator so that the stimulation is initiated when the patient falls asleep, and the stimulation is terminated when the patient wakes up.

Discussion

To reduce the computational complexity for the algorithmic analysis, it was envisaged to extract simple features from MM signals (standard deviation, maximum values, minimum values, mean, median, etc.) for each 30 seconds epoch of the signal and apply simple formulas to best classify cheek-derived MM signal into wake and sleep labels as defined by the reference chin-derived MM signal.

It appeared that standard deviation and maximum values were the most discriminative for detecting sleep/wake labels. To optimise the detection thresholds 3 different scenarios can be contemplated:

1. Maximization of wake detection and erroneous detection some sleep episodes as quiet wake (the stimulation will only start when the patient is obviously asleep, hence restraining the time window when the treatment is active). This scenario favours comfort by minimizing stimulation time while awake.

2. Balanced detection of wake and sleep, ensuring that most stimulation is restricted to true sleep and that stimulation lasts for the most part of the sleep period.

3. Maximization of sleep detection and erroneous detection of quiet wake as sleep (the stimulation could start when the patient is quietly awake, potentially disrupting the transition from wake to sleep). This scenario favours treatment efficacy by maximizing stimulation time.

In view of the reviewed data, it would appear the $3^{rd}$ scenario (sleep optimization) is preferred for the following reasons:

TST differences between the cheek and the chin MM sensor are no greater than what is expected from interscorer variability (~85%).

Application of simple detection rules to cheek-derived MM features allowed for detection of sleep and wake states with >75% accuracy, as initially hypothesized.

Scenario 3 leads to difference in TST of ~4.5% and a stimulation duration shorter than 4 h in 0% of subjects (4 h of daily treatment for OSA being recommended in clinical practice).

Implementation

Given these data, the following recommendations may be formulated for implementation in the wearable device's functionality:

1. The stimulators can have 2 different modes for being activated: a manual mode where users can decide when the stimulation starts and an intelligent mode where stimulation starts depending on users' MM.

2. The manual mode shall be programmable entirely:

a. Users shall be able to decide to start the stimulation directly.

b. Users shall be able to decide to start the stimulation with a delay (e.g., the stimulation will start 20 minutes after initiation).

c. Users shall be able to decide to start the stimulation with a progressive ramp to reach optimal current intensity.

3. The intelligent mode functions as follows:

a. The MM signals will be processed by 30-seconds epochs in a first intention. This time window shall be programmable.

b. Different features shall be extracted from the 30-seconds epochs. The features shall be programmable. Standard deviation and maximum values shall be extracted in a first intention.

c. The 30-seconds epochs shall be overlapping with a programmable interval and not successive to ensure that users do not have to wait 30 seconds for the stimulation to stop when it is supposed to. The 30-seconds epochs shall be refreshed every second as a first intention.

d. The intelligent stimulation mode will be implemented with the fixed standard deviation and maximum value thresholds that have the most sleep/wake discrimination value in the above-described report for the selected scenario (i.e., optimal sleep detection).

The selected thresholds are the following:

Wake is detected if standard deviation of gyroscope norm>1.17.

Wake is detected if maximum value of the gyroscope norm>14.35.

e. The pre-defined sleep/wake thresholds implemented in intelligent stimulation mode shall be programmable and personalized per patient. These thresholds shall be modified based on a first stimulation night to optimize sleep or wake detection in any given user. It shall be possible to use a first night with fixed parameters to distinguish sleep/wake to extract cut-off points adapted to each patient.

4. The intelligent mode shall also be programmable:
   a. Users shall be able to decide to start the intelligent stimulation directly (i.e., sleep/wake detection with the detection rules will start directly after initiation).
   b. Users shall be able to decide to start the intelligent stimulation with a delay (i.e., sleep/wake detection with the detection rules will start 20 minutes after initiation).
   c. Users shall be able to decide to start the intelligent stimulation with a progressive ramp to reach optimal current intensity (i.e., sleep/wake detection with the detection rules will start after a programmable delay (in minutes) after initiation and current will progressively increase to optimal intensity).

5. Following awakenings in both activation modes, stimulation will resume after a programmable delay (in minutes) and the absence of wake detection.

It is understood that the embodiments presented in present Example 6 form preferred embodiments of the wearable device of the present disclosure.

Figure 29:
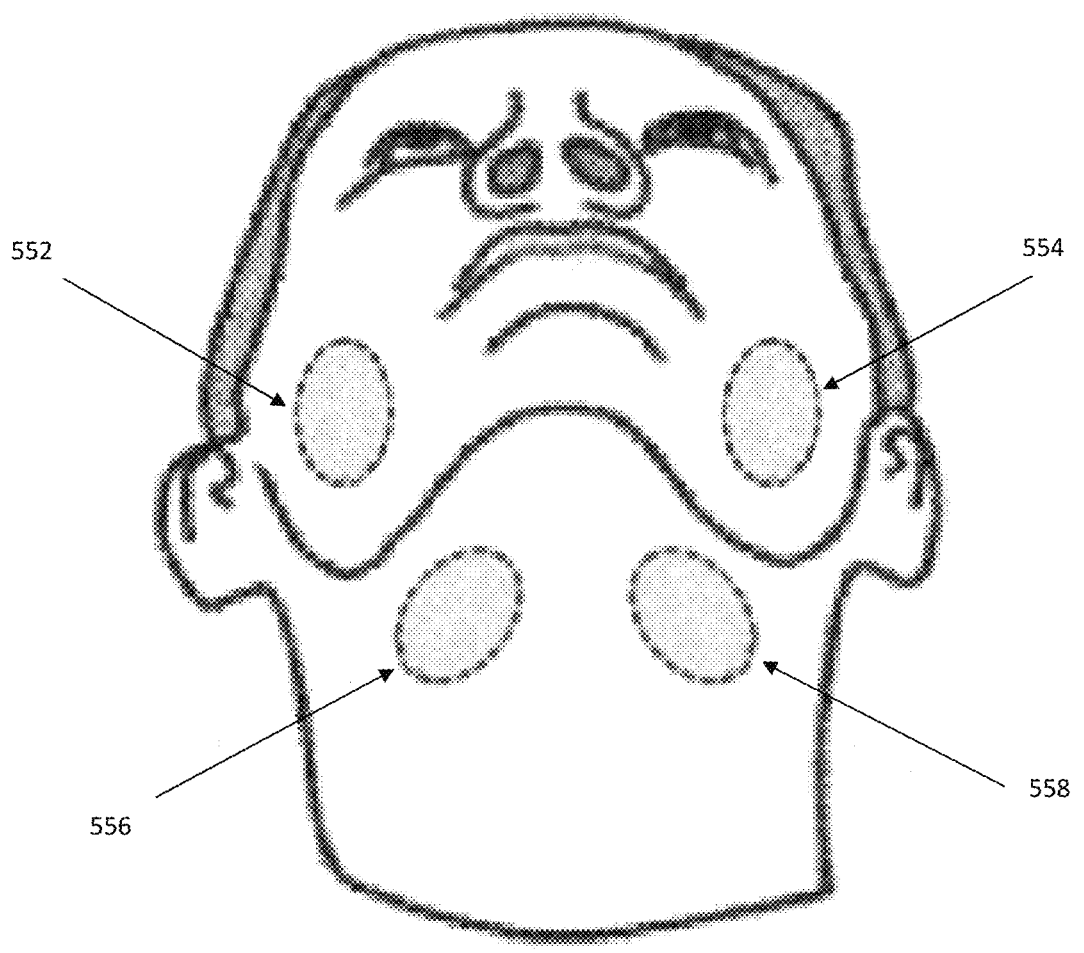
FIG. 29 is an illustration of the stimulation regions on a subject's skin for stimulating a patient's masseter and pterygoid muscles.

Referring now to FIG. 29, an illustration of stimulation regions on a subject's skin for positioning of electrodes is illustrated. For example, stimulation regions 552 and 554 may be adjacent to or otherwise positioned near the masseter muscles of the patient such that transcutaneous stimulation of stimulation regions 552 and 554 stimulates the masseter muscles. For example, stimulation region 552 may be a portion of the subject's skin that is adjacent to the right superficial masseter (SM) muscle of the subject and stimulation region 554 may be adjacent to the left superficial masseter (SM) muscle of the subject. Additionally, stimulation regions 556 and 558 may be adjacent to or otherwise positioned near the pterygoid muscles (e.g., medial pterygoid muscles) such that transcutaneous stimulation of stimulation regions 556 and 558 stimulates the pterygoid muscles. For example, stimulation region 556 may be a portion of the subject's skin that is adjacent to the right pterygoid muscle of the subject and stimulation region 558 may be adjacent to the left pterygoid muscle of the subject.

As explained above with respect to FIG. 1, to achieve an optimal stimulation response and/or reduced stimulation discomfort, each electrode of the wearable may be positioned into electrical contact with a selected portion of the subject's skin (e.g., stimulation regions 552-558). An exemplary skin portion for stimulating the masseter muscles is illustrated in FIG. 1 and ranges from a subject's masseter muscle motor point to a posterior angle of the subject's mandible. In one example, as explained above with respect to FIG. 1, placement of electrodes over the superficial masseter (SM) muscle may be guided by the gonion— located at the angle of the mandible (gonial angle)—and the body of zygomatic bone can be performed through palpation to identify anatomical reference landmarks. The superficial masseter muscle line is drawn from these reference landmarks, joining gonion, spotted on the soft tissue, to the mid-point between the lower posterior border of the zygomatic bone and the zygomatic arch, both also identified by palpation. The line may be adjusted to the fibres direction of superficial masseter muscle, which may be congruent with its origin and insertion. For example, the electrodes may be placed along this reference line, with their location of placement on the mark corresponding to 40% of the line. However, it is understood that electrodes may otherwise be positioned in the stimulation area in any suitable fashion such that the electrodes stimulate the masseter muscle.

In another example, the muscles may be contracted and surface electrodes may be placed along the muscle fibres over the most prominent region of muscle contraction to improve stimulation response. While palpating the muscle during contraction, it can be possible to verify electrodes positioning to perform any need of correction. In yet another example, the placement of electrodes may follow any approach set forth above, including via the user guide set forth above with respect to FIG. 9. It is understood that stimulation regions 552-554 and stimulation regions 556-558 may be larger or smaller or may be in a different location, provided that stimulating regions 552-554 stimulates the masseter muscles and stimulating regions 556-558 stimulates the pterygoid muscles.

Figures 30A, 30B:
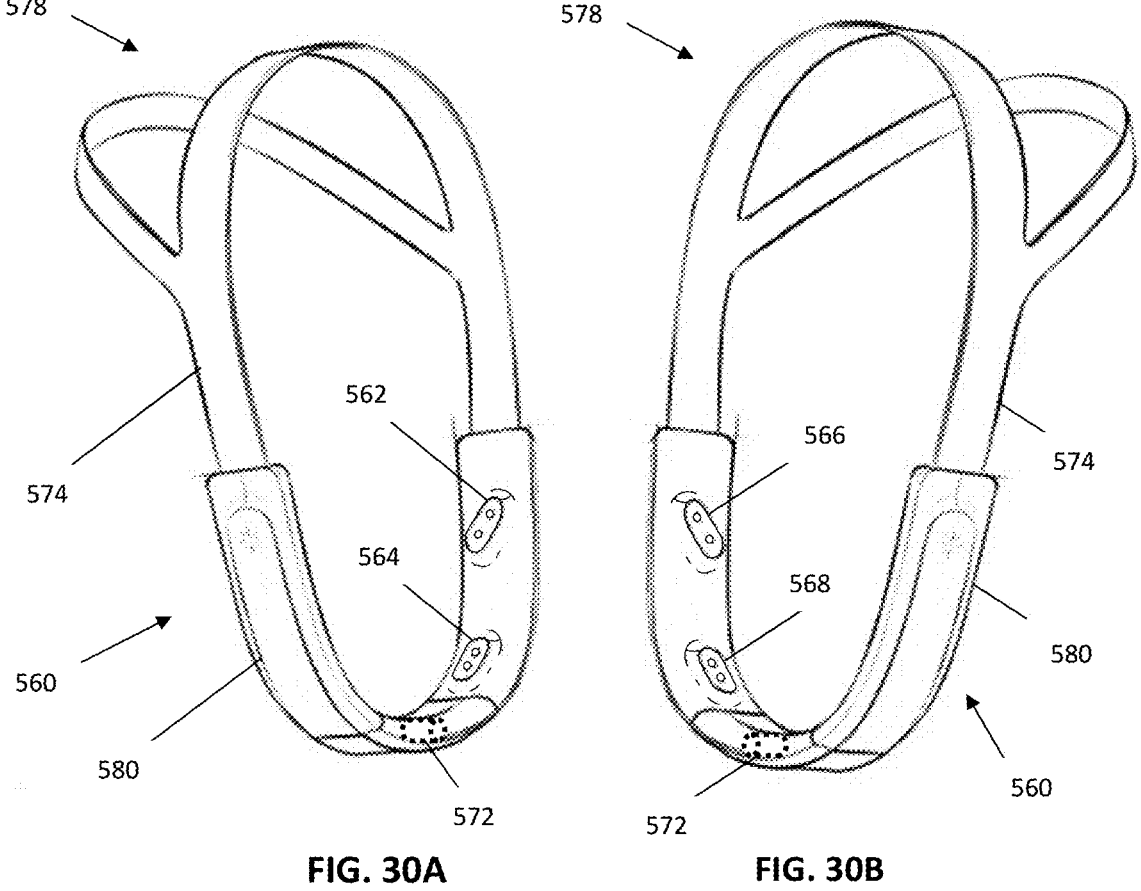
FIGS. 30A-30B are illustrations of a wearable device for positioning of electrodes for stimulating a patient's masseter and pterygoid muscles.

Referring now to FIGS. 30A-30B, wearable device 560 is illustrated. Wearable device is intended to be worn by a subject during sleep to transcutaneously stimulate the subject's masseter and pterygoid muscles. Wearable device 560 includes strap 580 which may be padded for comfort and may include electrodes for transcutaneously stimulating the subject's masseter and pterygoid muscles. For example, wearable device 560 may include left upper electrode 562, left lower electrode 564, right upper electrode 566 and/or right lower electrode 568. Left upper electrode 562, left lower electrode 564, right upper electrode 566 and/or right lower electrode 568 may be a monopolar electrode, a bipolar electrode and/or any other suitable electrode. In one example, left upper electrode 562, left lower electrode 564, right upper electrode 566 and/or right lower electrode 568 may be the same as or similar to bipolar electrode (100) illustrated in FIG. 10.

Wearable device 560 may include head support 574 which may include straps 578 that rest on the subject's head and may be two separated straps that converge. Head support 574 together with strap 580 may cause, when worn by the subject, left upper electrode 562 to be positioned over, on, or adjacent to the subject's left masseter muscle, left lower electrode 564 to be positioned over, on, or adjacent to the subject's left pterygoid muscle, right upper electrode 566 to be positioned over, on, or adjacent to the subject's right masseter muscle, and/or right lower electrode 568 to be positioned over, on, or adjacent to the subject's right pterygoid muscle. Head support 574 and strap 580 may be sized and/or adjusted such that left upper electrode 562, left lower electrode 564, right upper electrode 566 and/or right lower electrode 568 may be compressed against the skin of the subject at the stimulation regions illustrated in FIG. 29. The electrodes may be caused to stimulate simultaneously. Alternatively, left upper electrode 562 and right upper electrode 566 may stimulate the masseter muscles at a different time and/or according to different stimulation parameters than left lower electrode 564 and right lower electrode 568 stimulate the pterygoid muscles.

As shown in FIGS. 30A-30B, left upper electrode 562, left lower electrode 564, right upper electrode 566 and/or right lower electrode 568 may be protruded from strap 580 towards the subject to increase the pressure applied by the electrodes against the skin of the subject. It is understood that increased pressure of the electrodes against the skin of the subject may increase the efficacy of the stimulation. Such protrusions may be padded or compressible to improve comfort for the subject.

Wearable device 560 may further include sensor unit 572 in strap 580. While sensor unit 572 is illustrated in the middle of strap 580, it is understood that sensor unit 572 may be located anywhere on strap 580. Sensor unit 572 may include a gyroscope and/or an accelerometer. Additional sensor units may also be included on strap 580 (e.g., one sensor unit on a left side of strap 580 and another sensor unit on a right side of strap 580).

Sensor unit 572 may be used to detect mandible and/or head movement. For example, left upper electrode 562 and right upper electrode 566 may transcutaneously stimulate the masseter muscle to cause the masseter muscle to contract and left lower electrode 564 and right lower electrode 568 may transcutaneously stimulate the pterygoid muscle to cause the pterygoid muscle to contract, causing the subject's mandible to elevate to decrease respiratory effort during sleep. Sensor unit 572 may detect movement's in the mandible and/or discern between mandible movement and head movement. For example, a gyroscope may be used to determine rotation of the subject's mandible and the accelerometer may be used to detect movement of the head and together with the gyroscope may be used to discern movement of the subject's head from movement of the subject's mandible.

Based on mandible movement detected by sensor unit 572, the stimulation parameters used for causing left upper electrode 562 and right upper electrode 566 to transcutaneously stimulate the masseter muscles and/or left lower electrode 564 and right lower electrode 568 to transcutaneously stimulate the pterygoid muscles may be adjusted (e.g., using a mobile phone or computing device in wired or wireless communication with wearable device 560). The feedback loop described above with respect to FIG. 11 may be used to stimulate the masseter muscles and pterygoid muscles using wearable device 560. For example, sensor data generated by sensor unit 572 (e.g., mandibular activity data) may be analyzed to determine a stimulation response, which may include the elevation and/or stabilization of the subject's mandible and instruct the stimulator to adjust one or more stimulation parameters to control the elevation and stabilization of the subject's mandible. The mandible activity data may also be used to determine the occurrence of muscle fatigue.

Sensor unit 572 may also detect, determine and/or record data related to the subject's respiration activity or sleeping activity. Sensor unit 572 may optionally include a microphone, temperature sensor and/or any other sensor suitable for detecting the subject's respiration and/or sleeping activity (e.g., sleep activity data). The respiration activity data may refer to any data relating to the subject's respiration, such as breathing rate or intensity. espiration activity data may also be derived from the mandibular activity data or combined with the mandibular activity data. Similarly, sleeping activity data may refer to any data relating to the subject's sleeping, such as sleep related movements (e.g., head movement rhythms indicative of sleep and/or sleep cycles). Sleeping activity data may also be derived from the mandibular activity data or combined with the mandibular activity data and/or the respiration activity data. The mandibular activity data, respiration activity data, and sleeping activity data may be analyzed to provide a feedback loop to the stimulator to improve the stimulation efficacy, improve comfort, and/or improve the user experience generally.

Based on the mandibular activity data, respiration activity data, and/or sleeping activity data, one or more stimulation parameters may be adjusted (e.g., using a mobile device or computing device in wired or wireless communication with the wearable device) to reduce the intensity of the sleep respiratory disturbance or prevent the occurrence of a further sleep respiratory disturbance and/or may be adjusted to initiate the electrical stimulation when the subject falls asleep and terminate the electrical stimulation when the subject awakes, as detected using the sensor unit. In another example, sleep activity data determining by sensor unit 572 may be analyzed to determine sleeping stages, which may include a light sleeping (N1) stage, a light sleeping (N2) stage, a REM stage, and/or a deep sleeping (N3) stage. The stimulator may initiate the electrical stimulation when the subject enters the light sleeping (N1) stage, the light sleeping (N2) stage, and/or the REM stage and terminate the electrical stimulation when the subject enters the deep sleeping (N3) stage.

Figures 31A, 31B:
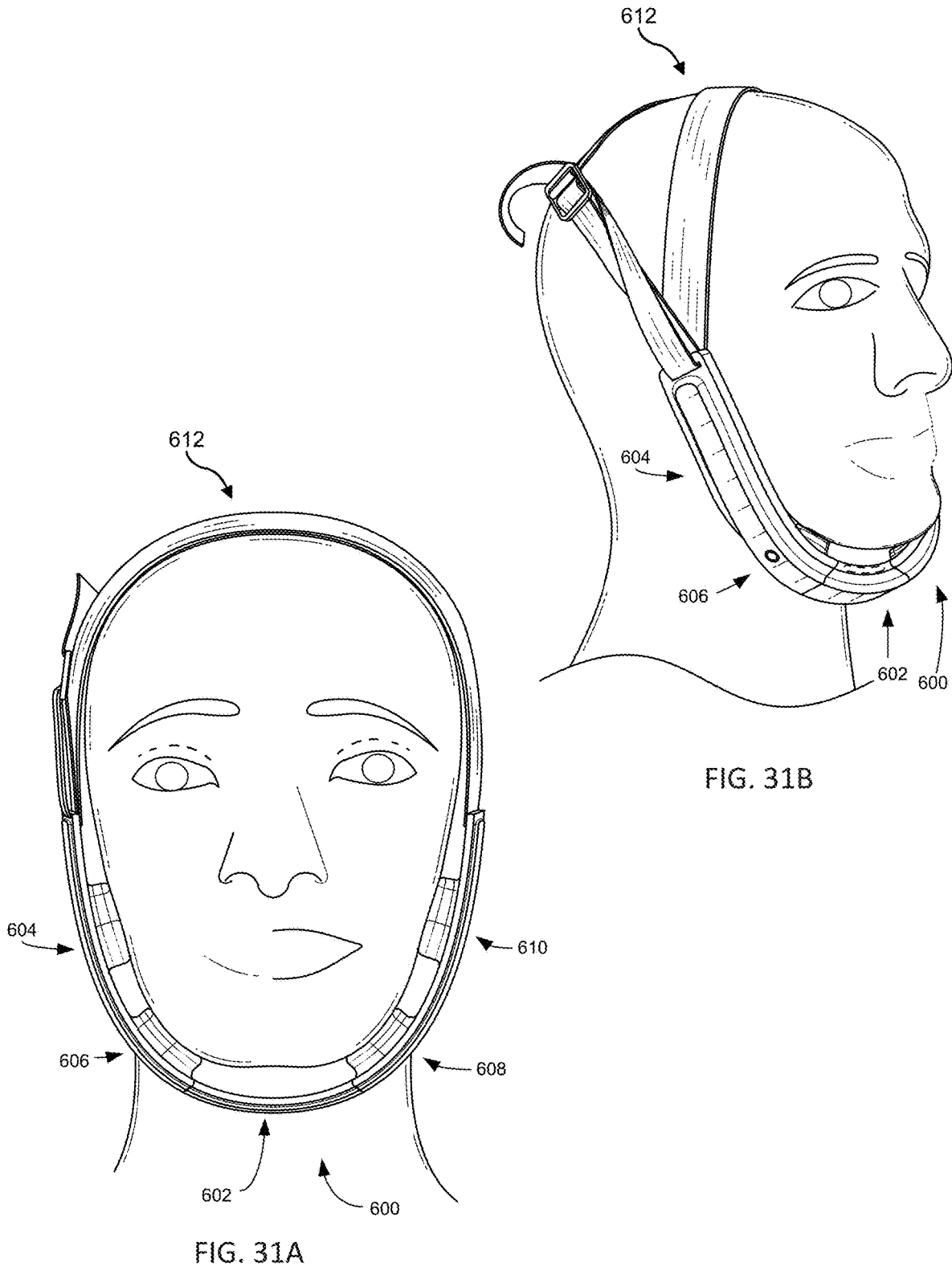
FIGS. 31A-31B are illustrations of a wearable device with an adjustable strap for positioning of electrodes for stimulating a patient's masseter and pterygoid muscles.
Figure 32:
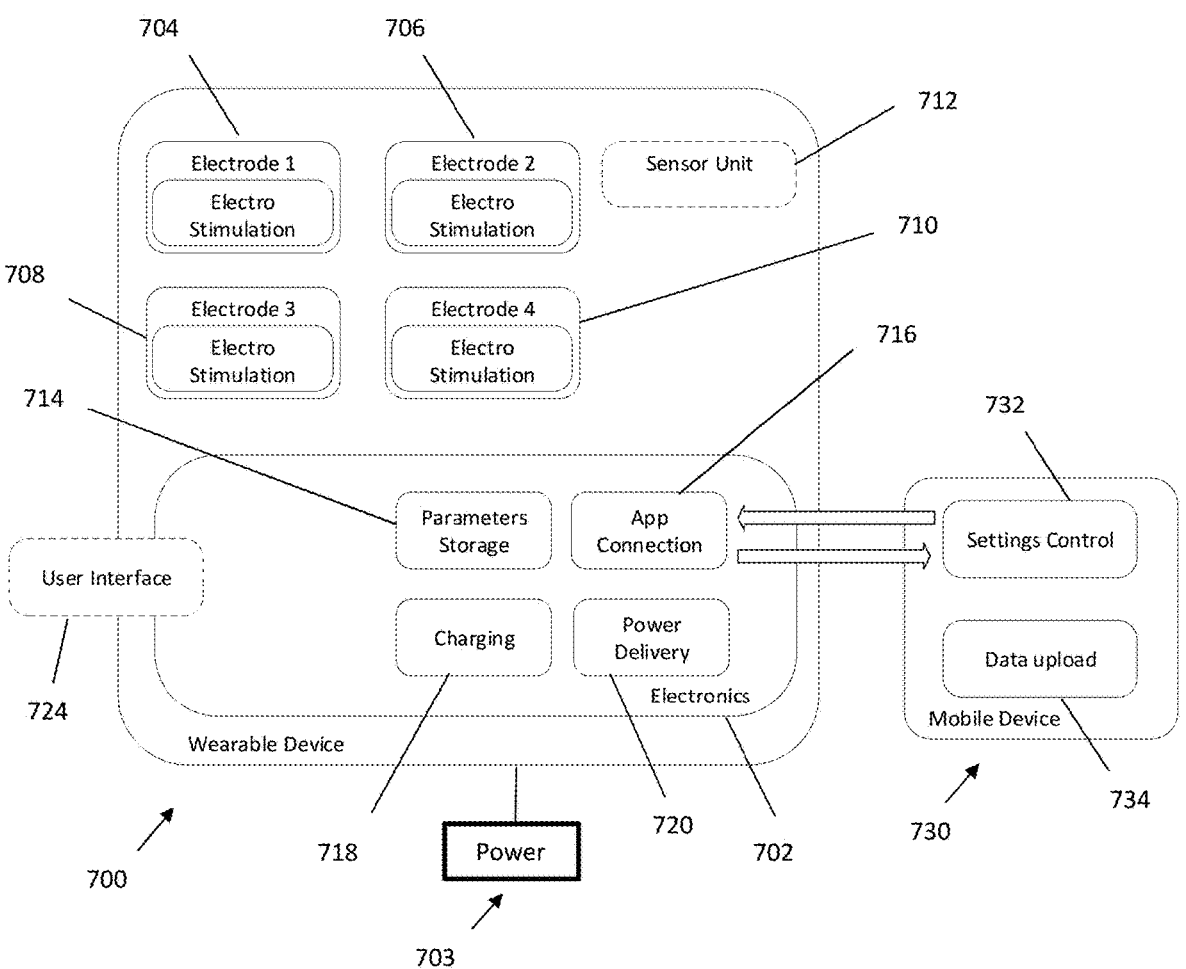
FIG. 32 is an illustration of a schematic of the wearable device and a mobile device in communication with the wearable device.

Referring now to FIGS. 31A-31B, wearable device 600 is illustrated. Wearable device 600 may be similar to wearable device 560 of FIGS. 30A-30B, and may be intended to be worn by a subject during sleep to transcutaneously stimulate the subject's masseter and pterygoid muscles. Wearable device 600 may include strap 602 which may be similar to strap 580 of FIGS. 30A-30B and right upper electrode 604, right lower electrode 606, left lower electrode 608 and left upper electrode 610, which may be the same as or similar to right upper electrode 556, right lower electrode 568, left lower electrode 564 and left upper electrode 562 of FIGS. 30A-30B, respectively. Strap 602 may optionally include a sensor unit (not shown). Head support 612 may be the same as or similar to head support 574 of FIGS. 30A-30B and may connect to strap 602. Head support 612 may include two straps that each may conform to the shape of the subject's head. The two straps may help stabilize wearable device 600 and may facilitate uniform compression on right upper electrode 604, right lower electrode 606, left lower electrode 608, and left upper electrode 610 on the subject's skin. Head support 612 may further include one or more buckles or other adjustment features for adjusting the length of either or both straps of head support 612. Strap 602 may also optionally include a buckle or adjustment feature for adjusting the length of strap 602. Referring now to FIG. 32, a schematic view of the wearable device and a mobile device in communication with the wearable device is illustrated. As shown in FIG. 32, wearable device 700 may communicate via a wireless connection with mobile device 730. Wearable device 700 may be the same as or similar to wearable device 560 of FIGS. 30A-30B. Mobile device 730, may be any suitable mobile or computing device having a processor and memory (e.g., smartphone, smart device, tablet, laptop, wearable device, desktop, and the like).

Wearable device 700 may include electrode 704, electrode 706, electrode 708, and electrode 710, which may be the same as or similar to left upper electrode 562, left lower electrode 564, right upper electrode 566 and/or right lower electrode 568 of FIGS. 30A-30B and may each provide electro stimulation to the subject for transcutaneous stimulation. Wearable device 700 may optionally include sensor unit 712 which may be the same as or similar to sensor unit 572 of FIGS. 30A-30B. Sensor unit 712 may alternatively, or additionally, be a part of or otherwise may be incorporated into or may incorporate one of electrode 704, electrode 706, electrode 708, or electrode 710. Sensor unit 712 may be used to detect obstructive sleep apnea.

Wearable device 700 may further include electronics 702, which may include hardware and software for operating wearable device 700. For example, app connection 716 may facilitate communication and data transfer between wearable device 700 and mobile device 730. Parameters storage 714 may store and/or save stimulation parameters which may include stimulation patterns, durations, intensities and the like. Charging 718 may oversee charging of a battery of wearable device 700. Power delivery 720 may oversee delivery of electrical power to each of electrodes 704-710 based on certain stimulation parameters. For example, wearable device 700 may include or may be connected to power 703 which may be any suitable power source such as a battery. Electronics 702 may optionally include user interface 724 which may be any component for providing or otherwise presenting information to a user and/or receiving user input. For example, user interface may be a display screen, a touchscreen, a button, a microphone, a speaker, and/or the like.

Mobile device 730 may include settings control 732 for communicating with app connection 716 of wearable device 700 and for sending certain settings and/or parameters to wearable device 700 for controlling wearable device 700. Data upload 734 may oversee the upload of data or other information from other computing devices such as from a remote sever and/or wearable device. Such information may include user settings, software updates, user information (e.g., sleep or health related information such as sleep cycle or duration data and/or heart rate information), and/or any other information that would be helpful for operating wearable device 700.

The invention claimed is:

1. A wearable device for decreasing respiratory effort of a subject during sleep, the wearable device comprising:
a housing configured to be worn on the subject's head and/or neck during sleep and comprising a first housing portion and a second housing portion;
a first bipolar electrode comprising first and second electrode portions disposed within the first housing portion such that the first housing portion is mounted on the subject's skin over a masseter muscle so that the first bipolar electrode is configured to transcutaneously stimulate the masseter muscle of the subject when the wearable device is worn by the subject during sleep;
a second bipolar electrode comprising third and fourth electrode portions disposed within the second housing portion such that the second housing portion is mounted on the subject's skin over a pterygoid muscle so that the second bipolar electrode is configured to transcutaneously stimulate the pterygoid muscle of the subject when the wearable device is worn by the subject during sleep; and
a stimulator coupled to the first bipolar electrode and the second bipolar electrode, the stimulator configured to cause the first bipolar electrode to transcutaneously stimulate the masseter muscle to cause the masseter muscle to contract and configured to cause the second bipolar electrode to transcutaneously stimulate the pterygoid muscle to cause the pterygoid muscle to contract, thereby elevating the subject's mandible to decrease respiratory effort during sleep.

2. The wearable device of claim 1, further comprising:
a third electrode coupled to the housing and positioned with respect to the housing such that the third electrode is mounted on the subject's skin and configured to transcutaneously stimulate a second masseter muscle of the subject when the wearable device is worn by the subject; and
a fourth electrode coupled to the housing and positioned with respect to the housing such that the fourth electrode is mounted on the subject's skin and configured to transcutaneously stimulate a second pterygoid muscle of the subject when the wearable device is worn by the subject.

3. The wearable device of claim 2, wherein the third and fourth electrodes are each bipolar electrodes each comprising first and second electrode portions, and wherein the first and second electrode portions of the third electrode are each configured to be positioned on the subject's skin at the left masseter muscle and the first and second electrode portions of the fourth electrode are each configured to be positioned on the subject's skin at the left pterygoid muscle.

4. The wearable device of claim 1, wherein the first and second electrodes each comprise adhesive surfaces configured to be adhered to the subject's skin.

5. The wearable device of claim 1, wherein the housing comprises a collar configured to be worn on the subject's neck during sleep.

6. The wearable device of claim 1, wherein the stimulator is configured to cause the first electrode and the second electrode to transcutaneously stimulate simultaneously.

7. The wearable device of claim 1, wherein the stimulator is configured to cause the first electrode and the second electrode to transcutaneously stimulate sequentially.

8. The wearable device of claim 1, wherein the stimulator is programmed with a stimulation regime wherein the stimulator causes transcutaneous stimulation to the first electrode and the second electrode for a stimulation period followed by no stimulation for a rest period, wherein the stimulation period followed by the rest period is repeated throughout a sleep period of the subject.

9. The wearable device of claim 1, further comprising a sensing unit comprising one or more of an accelerometer or a gyroscope configured to sense movement of the subject's mandible, wherein the stimulator is configured to cause the first electrode to transcutaneously stimulate the masseter muscle and the second electrode to transcutaneously stimulate the pterygoid muscle responsive to movement of the subject's mandible sensed by the sensing unit.

10. The wearable device of claim 1, wherein the housing comprises an adjustable strap configured to be adjusted to the subject's head and/or neck.

11. The wearable device of claim 10, wherein the housing wraps around a top of subject's head and beneath the subject's mandible.

12. A method for decreasing respiratory effort of a subject during sleep using a wearable device, the method comprising:
providing the wearable device, the wearable device comprising a housing comprising a first housing portion and a second housing portion and adapted to be worn on the subject's head and/or neck during sleep, first and second bipolar electrodes each comprising first and second electrode portions disposed within the first housing portion and the second housing portion, respectively, and a stimulator coupled the first and second electrodes, the first housing portion is mounted on the subject's skin over a masseter muscle so that the first bipolar electrode is configured to transcutaneously stimulate the masseter muscle of the subject when the wearable device is worn by the subject during sleep, and the second housing portion is mounted on the subject's skin over a pterygoid muscle so that the second bipolar electrode is configured to transcutaneously stimulate the pterygoid muscle of the subject when the wearable device is worn by the subject during sleep;
causing the stimulator to transcutaneously stimulate the masseter muscle via the first bipolar electrode to cause the masseter muscle to contract; and
causing the stimulator to transcutaneously stimulate the pterygoid muscle via the second bipolar electrode to cause the pterygoid muscle to contract;

wherein transcutaneously stimulating the masseter muscle and the pterygoid muscle elevates a mandible of the subject to decrease respiratory effort during sleep.

13. The method of claim 12, wherein the wearable device further comprises a third electrode coupled to the housing and positioned with respect to the housing such that the third electrode is mounted on the subject's skin and adapted to transcutaneously stimulate a second masseter muscle of the subject when the wearable device is worn by the subject and a fourth electrode coupled to the housing and positioned with respect to the housing such that the fourth electrode is mounted on the subject's skin and adapted to transcutaneously stimulate a second pterygoid muscle of the subject when the wearable device is worn by the subject.

14. The method of claim 12, wherein the third and fourth electrodes are each bipolar electrodes each comprising first and second electrode portions, and wherein the first and second electrode portions of the third electrode are each adapted to be positioned on the subject's skin at the left masseter muscle, and the first and second electrode portions of the fourth electrode are each adapted to be positioned on the subject's skin at the left pterygoid muscle.

15. The method of claim 12, wherein the first and second electrodes each comprise adhesive surfaces configured to be adhered to the subject's skin.

16. The method of claim 12, wherein the housing comprises a collar configured to be worn on the subject's neck during sleep.

17. The method of claim 12, wherein the stimulator causes the first electrode and the second electrode to transcutaneously stimulate simultaneously.

18. The method of claim 12, wherein the stimulator is configured to cause the first electrode and the second electrode to transcutaneously stimulate sequentially.

19. The method of claim 12, wherein the stimulator causes the first electrode and the second electrode to stimulate for a stimulation period followed by no stimulation for a rest period, wherein the stimulation period followed by the rest period is repeated throughout a sleep period of the subject.

20. The method of claim 12, wherein the wearable device further comprises a sensing unit having one or more of an accelerometer or a gyroscope adapted to sense movement of the subject's mandible, wherein the first electrode is caused to transcutaneously stimulate the masseter muscle and the second electrode is caused to transcutaneously stimulate the pterygoid muscle responsive to movement of the subject's mandible sensed by the sensing unit.

* * * * *